US 8,431,381 B2
Apr. 30, 2013

(12) United States Patent
Ochiai

(54) ATP:CITRATE LYASE GENES

(75) Inventor: Misa Ochiai, Osaka (JP)

(73) Assignee: Suntory Holdings Limited, Osaka (JP)

( * ) Notice: Subject to any disclaimer, the term of this patent is extended or adjusted under 35 U.S.C. 154(b) by 212 days.

(21) Appl. No.: 12/738,108

(22) PCT Filed: Oct. 24, 2008

(86) PCT No.: PCT/JP2008/069372
§ 371 (c)(1),
(2), (4) Date: Apr. 15, 2010

(87) PCT Pub. No.: WO2009/054511
PCT Pub. Date: Apr. 30, 2009

(65) Prior Publication Data
US 2011/0009655 A1 Jan. 13, 2011

(30) Foreign Application Priority Data
Oct. 26, 2007 (JP) ................................. 2007-278612

(51) Int. Cl.
C12N 9/88 (2006.01)
C12N 1/20 (2006.01)
C12N 15/00 (2006.01)
C12Q 1/00 (2006.01)
C12Q 1/68 (2006.01)
C12P 21/06 (2006.01)
C12P 21/04 (2006.01)
C12P 7/64 (2006.01)
C07H 21/04 (2006.01)
C07H 21/02 (2006.01)

(52) U.S. Cl.
USPC ............... 435/232; 435/4; 435/6.1; 435/69.1; 435/71.1; 435/252.3; 435/320.1; 435/440; 435/134; 536/23.2; 536/23.1

(58) Field of Classification Search .................. None
See application file for complete search history.

(56) References Cited

U.S. PATENT DOCUMENTS
2006/0051847 A1  3/2006  Gunnarsson et al.

FOREIGN PATENT DOCUMENTS
WO  WO2005/118814   12/2005
WO  2006/102342 A2   9/2006

OTHER PUBLICATIONS

Branden et al. Introduction to Protein Structure, Garland Publishing Inc., New York, p. 247, 1991.*
Wynn et al., "Evidence that the Rate-Limiting Step for the Biosynthesis of Arachidonic Acid in *Mortierella alpina* is at the Level of the 18:3 to 20:3 elongase," *Microbiology*, vol. 146, No. 9, pp. 2325-2331, 2000.
Nowrousian et al., "Cell Differentiation during Sexual Development of the Fungus *Sordaria macrospora* Requires ATP Citrate Lyase Activity," *Molecular and Cellular Biology*, vol. 19, No. 1, pp. 450-460, 1999.
Database GenBank Accession No. AJ243817 <http//www.ncbi.nlm.nih.gov/entrez/viewer.fcgi?db=nucleotide&val=7160183>, Nov. 14, 2006.
Elshourbagy et al., "Rat ATP Citrate-Lyase: Molecular Cloning and Sequence Analysis of a Full-Length cDNA and mRNA Abundance as a Function of Diet, Organ, and Age," *J. Biol. Chem.*, vol. 265, No. 3, pp. 1430-1435, 1990.
Database GenBank Accession No. U18197, http://www.ncbi.nlm.nih.gov/entrez/viewer.fcgi?db=nuccore&id=603073, Dec. 18, 1994.
Database GenBank Accession No. AY971952, http://www.ncbi.nlm.nih.gov/entrez/viewer.fcgi?db=nuccore&id=63364937, Jan. 1, 2006.
Nowrousian et al., "The Fungal *acl1* and *acl2* Genes Encode Two Polypeptides with Homology to the N-and C-Terminal Parts of the Animal ATP Citrate Lyase Polypeptide," *Curr. Genet.*, vol. 37, No. 3, pp. 189-193, 2000.
Calder, "n-3 Fatty Acids, Inflammation, and Immunity-Relevance to Postsurgical and Critically Ill Patients," *Lipids*, vol. 39, No. 12, pp. 1147-1161, 2004.
Ratledge et al., "The Biochemistry and Molecular Biology of Lipid Accumulation in Oleaginous Microorganisms," *Adv. Appl. Microbiol.*, vol. 51, pp. 1-51, 2002.
Elshourbagy et al., "Cloning and Expression of a Human ATP-Citrate Lyase cDNA," *Eur. J. Biochem.*, vol. 204, pp. 491-499, 1992.
Fatland et al., "Molecular Characterization of a Heteromeric ATP-Citrate Lyase That Generates Cytosolic Acetyl-Coenzyme A in Arabidopsis," *Plant Physiology*, vol. 130, pp. 740-756, 2002.
Rangasamy et al., "Genetic Enhancement of Fatty Acid Synthesis by Targeting Rat Liver ATP:Citrate Lyase into Plastids of Tobacco," *Plant Physiology*, vol. 122, pp. 1231-1238, 2000.
International Search Report for PCT/JP2008/069372, mailed Nov. 18, 2008.
Wynn et al., "Short communication: Widespread occurrence of ATP: Citrate lyase and carnitine acetyltransferase in filamentous fungi," World Journal of Microbiology and Biotechnology, vol. 14, No. 1, Jan. 1998, pp. 145-147, XP002605401, ISSN: 0959-3993, Jan. 1998.
Park et al., "Cloning and characterization of the 5' flanking region of human ATP-citrate lyase gene," Biochimica et Biophysica Acta, vol. 1353, No. 2, 1997, pp. 236-240, XP9140085, ISSN: 0006-3002, 1997. Adachi et al., "Oryza sativa Japonica Group cDNA clone: 002-160-D10, full insert sequence," Database EMBL [Online], Jul. 19, 2003, XP002605403, retrieved from EBI, Database accession No. AK110061,—Jul. 19, 2003.
Birren et al., "SubName: Full=ATP citrate lyase isoform 2," Database UniProt [Online], Jan. 15, 2008, XP002605404, retrieved from EBI, Database accession No. A8P9E0, Jan. 15, 2008.
Extended European Search Report dated Dec. 8, 2010 that issued with respect to European Patent Application No. 08841099.8.

(Continued)

Primary Examiner — Yong Pak
(74) Attorney, Agent, or Firm — Greenblum & Bernstein, P.L.C.

(57) ABSTRACT

The present invention provides novel genes for ATP:citrate lyase.
A nucleic acid comprising the nucleotide sequence shown in SEQ ID NO: 5, 6, 9 or 10 or a fragment thereof.

10 Claims, 10 Drawing Sheets

OTHER PUBLICATIONS

Database GenBank Accession No. XM_001839699, http://www.ncbi.nlm.nih.gov/nuccore/XM_001839699, retrieved Sep. 26, 2012.
Database GenBank Accession No. XM_001211553, http://www.ncbi.nlm.nih.gov/nuccore/XM_001211553, retrieved Sep. 26, 2012.
Database GenBank Accession No. XM_001258189, http://www.ncbi.nlm.nih.gov/nuccore/XM_001258189, retrieved Sep. 26, 2012.
Database GenBank Accession No. AL110804, http://www.ncbi.nlm.nih.gov/nuccore/AL110804, retrieved Sep. 26, 2012.
Database GenBank Accession No. EIE89486, http://www.ncbi.nlm.nih.gov/protein/EIE89486, retrieved Sep. 26, 2012.
English language translation of Russian Office Action issued with respect to Russian Application No. 2010121153 issued Jul. 16, 2012.

* cited by examiner

Figure 1-1

```
   1   TTGCCTGTCCCTCCTGGCGCCCCTTCTCTCACTACTCACTAGACTCGTCCTCCTCCTCTACATTGTATACCTAGCCTTCTCTTCCTACGGTCTCCTTCCG

101   CTCCTGGTGCTTTCTATACTCATCCTCTTTGCATAGCATTTTCTCCCCTTCTATAATATACATACACACACAACAAGATGTCTGCTAAAGCCGTTCGCCA
                                                                                 M  S  A  K  A  V  R  E ·

201   ATACGATGGAAAGCTGCTCTTGGCCCACTGGCTTCACCGTGTTGCCGTGCCCGAATCAGAGACCGCAGGATCAGCAACAACGGGATCCAAGTTCGTCCAG
       · Y  D  G  K  L  L  L  A  H  W  L  H  R  V  A  V  P  E  S  E  T  A  G  S  A  T  T  G  S  K  F  V  Q

301   CCCACCACCCGCCTTGCCCACATCTCCATCGACACCTCGCTCTTGCAGGACAAGACCCAGTTCGATCAGCACGTCCGCTCGACCTTGGATCAGCTCGAGG
         P  T  T  R  L  A  H  I  S  I  D  T  S  L  L  Q  D  K  T  Q  F  D  Q  H  V  R  S  T  L  D  Q  L  E  V ·

401   TCTCGCACCCTTGGCTGTTGACCAACAAGCTGGTCGCCAAGCCTGACCAGTTGATCAAGCGTCGTGGAAAGAGCGGCTTGCTGCTCTTGAACGCCGAATG
       · S  H  P  W  L  L  T  N  K  L  V  A  K  P  D  Q  L  I  K  R  R  G  K  S  G  L  L  L  L  N  A  E  W ·

501   GGCTGAGGCTAGAGCCTGGATCGAGAAGCACGCGGCCAAGGACGTCCTTGTGGACTCGGTTCCCGGTGTTCTCAAGACCTTCCTCGTCGAGCCCTTCATT
       · A  E  A  R  A  W  I  E  K  H  A  A  K  D  V  L  V  D  S  V  P  G  V  L  K  T  F  L  V  E  P  F  I

601   CCCCACCCTTCTAACACTGAGTACTACATCTGCATCAACTCAGATCGTGATGGTGACAACATCCTCTTCACGCACGAGGGAGGTATCGAGGTCGGAGATG
         P  H  P  S  N  T  E  Y  Y  I  C  I  N  S  D  R  D  G  D  N  I  L  F  T  H  E  G  G  I  E  V  G  D  V ·

701   TTGATGCCAAGGCATTGAAGCTCCAGGTGAAGGTTCAGGACGCCTTCCCCACCGCAGAGGCCATTCGCTCGGCTCTCCTGGTCCATGTCCCTGAGGCCAA
       · D  A  K  A  L  K  L  Q  V  K  V  Q  D  A  F  P  T  A  E  A  I  R  S  A  L  L  V  H  V  P  E  A  K ·

801   GCACGATGTTCTTGTTGACTTTATCACTCGCCTCTATGCTGTTTACATCGACCTCCACTTCACCTACCTTGAGATCAACCCCTTGGTCGTCTTGGATCCC
       · H  D  V  L  V  D  F  I  T  R  L  Y  A  V  Y  I  D  L  H  F  T  Y  L  E  I  N  P  L  V  V  L  D  P

901   ACAGAGGACGAGCCTGCTCGTGTCTACTACCTCGACCTGGCTGCTAAGCTCGATCAGACTGCAGAGTTCGAGGCTGGTCCCAAGTGGGCCATCGCCAGAG
         T  E  D  E  P  A  R  V  Y  Y  L  D  L  A  A  K  L  D  Q  T  A  E  F  E  A  G  P  K  W  A  I  A  R  A ·

1001   CTCCTCAGAACATTGGAATTGCTGGCGTCATCCCCACCACTGTTGGCGCTGATGCTGGCCCTGGCATGGATTTCCCCGCACCTTTCGGTCGTGAATTGAC
       · P  Q  N  I  G  I  A  G  V  I  P  T  T  V  G  A  D  A  G  P  G  M  D  F  P  A  P  F  G  R  E  L  T ·

1101   CAAGGAGGAGGCCTATGTTCAGGAGCTGGACTCTAAGACCGGTGCTTCGCTCAAGCTCACCATCCTGAACAAGGATGGACGCATCTGGACCATGGTTGCT
       · K  E  E  A  Y  V  Q  E  L  D  S  K  T  G  A  S  L  K  L  T  I  L  N  K  D  G  R  I  W  T  M  V  A

1201   GGAGGCGGTGCCTCTGTCGTTTACAGTGATGCCATCGCTGCCCTTGGCCAGGCTGACGAGCTCGCCAACTACGGAGAGTACTCTGGTGCCCCCACCGAGA
         G  G  A  S  V  V  Y  S  D  A  I  A  A  L  G  Q  A  D  E  L  A  N  Y  G  E  Y  S  G  A  P  T  E  T ·

1301   CCCAGACCTATGAATACGCCAAGACCATCCTTGACCTTATGACCCGCTCTGCCACCCCTCACCCCGAGGGCAAGGTCCTGATCATTGGAGGAGGTATCGC
       · Q  T  Y  E  Y  A  K  T  I  L  D  L  M  T  R  S  A  T  P  H  P  E  G  K  V  L  I  I  G  G  G  I  A ·

1401   CAACTTCACTAACGTCGCCTCGACCTTCAAGGGAATTGTCCGCGCTCTTACCGAGTTTAAACAGCCCTTGATCGCCCACAAGGTCCGCATCTTTGTCCGT
       · N  F  T  N  V  A  S  T  F  K  G  I  V  R  A  L  T  E  F  K  Q  P  L  I  A  H  K  V  R  I  F  V  R

1501   CGTGGTGGTCCCAACTACCAGGAGGGTCTTCGCTCCATGCGTCAACTCGGCGAGTCCTTGGGAGTTGAGATCCAGGTCTTTGGACCCGAGACCCACATCA
         R  G  G  P  N  Y  Q  E  G  L  R  S  M  R  Q  L  G  E  S  L  G  V  E  I  Q  V  F  G  P  E  T  H  I  T ·

1601   CCGAGATTGTTCCTCTGGCCTTGACTGGACGCTCTTCCGACAACTTGGCTGCCACCAACGCCAACAACGGCAGCGCCTCGTCCGGAAACCTCCTTCAGGA
       · E  I  V  P  L  A  L  T  G  R  S  S  D  N  L  A  A  T  N  A  N  N  G  S  A  S  S  G  N  L  L  Q  D ·

1701   TCAGCTCTTGGGCACCAACAGCAACCTCAACACCCCTGTTCCCACTGCCCCCGTCTCCCGTGCTGGCACTCCTCCCGCCAGCGAGAGGATGACTTACTTC
       · Q  L  L  G  T  N  S  N  L  N  T  P  V  P  T  A  P  V  S  R  A  G  T  P  P  A  S  E  R  M  T  Y  F

1801   ACGGACGCAGACGCAAAGAAGGTCGGCCACGATTCCAACGTTCCCTTCACTGCCCAGACTCGCTCGTTCATCTACGGAATGCAGCCCCGTGCTGTTCAGG
         T  D  A  D  A  K  K  V  G  H  D  S  N  V  P  F  T  A  Q  T  R  S  F  I  Y  G  M  Q  P  R  A  V  Q  G ·
```

*Figure 1-2*

```
1901   GAATGCTCGACTTTGATTTCATCTGCAAGCGTGAGGTCCCCTCGGTCGCAGCCATGATCTACCCCTTTGGCGGTGCTCACGTTCAGAAGTTCTACTGGGG
        · M  L  D  F  D  F  I  C  K  R  E  V  P  S  V  A  A  M  I  Y  P  F  G  G  A  H  V  Q  K  F  Y  W  G ·

2001   CACCAAGGAGACTCTCTTGCCCGTTTACACTACTCTGGAGGAGGCCACTGCCAAGTTCCCCGAGGTTGATACCGTCGTCAACTTTGCCTCGTGCCGCTCT
        · T  K  E  T  L  L  P  V  Y  T  T  L  E  E  A  T  A  K  F  P  E  V  D  T  V  V  N  F  A  S  C  R  S

2101   GTTTACCAGTCCACGGTTGATATCCTCAGTCACTCTGACCAGATCAAGACGATCTCGATCATTGCCGAGGGTGTCCCCGAGCGTCGTGCTCGCCAGATCC
          V  Y  Q  S  T  V  D  I  L  S  H  S  D  Q  I  K  T  I  S  I  I  A  E  G  V  P  E  R  R  A  R  Q  I  L ·

2201   TCTGGGAGGCCAAGGCCAAGAACGTGCTCGTGATCGGACCAGCCACTGTCGGAGGCATCAAGCCCGGCTGCTTCAAGATCGGAAACACTGGAGGTATGAT
        · W  E  A  K  A  K  N  V  L  V  I  G  P  A  T  V  G  G  I  K  P  G  C  F  K  I  G  N  T  G  G  M  M ·

2301   GGACAACATTGTCTCGTCCAAGTTGTACCGCGCCGGTTCTGTTGCCTACGTCTCCAAGTCTGGCGGTATGTCCAACGAGCTGAACAACATCATCTCGCGC
        · D  N  I  V  S  S  K  L  Y  R  A  G  S  V  A  Y  V  S  K  S  G  G  M  S  N  E  L  N  N  I  I  S  R

2401   ACCACTGACGGTGTCTACGAGGGAGTCGCCATCGGAGGAGACCGTTACCCTGGATCGACCTTCATCGACCACTTGCTTCGCTATGAGCGGGACCCCAACT
          T  T  D  G  V  Y  E  G  V  A  I  G  G  D  R  Y  P  G  S  T  F  I  D  H  L  L  R  Y  E  R  D  P  N  C ·

2501   GCAAGATGTTGGTCTTGCTCGGAGAGGTCGGAGGTGTCGAGGAGTACAAGGTCTGTGAGGCGATCAAGAACGGGACCATCCGCAAGCCCGTGATTGCCTG
        · K  M  L  V  L  L  G  E  V  G  G  V  E  E  Y  K  V  C  E  A  I  K  N  G  T  I  R  K  P  V  I  A  W ·

2601   GTGCATCGGTACCTGCGCCAAGATGTTTGCCACCGAGGTCCAGTTCGGACACGCCGGTGCCTTGGCCCAGTCCGATCTCGAGACTGCCGATGCCAAGAAC
        · C  I  G  T  C  A  K  M  F  A  T  E  V  Q  F  G  H  A  G  A  L  A  Q  S  D  L  E  T  A  D  A  K  N

2701   AAGGCTCTCCGCGCCGCTGGTGTGGTCGTTCCCGAGACCTTTGAGAAGTTGCCCTTGGTCTTGAGCCAGACCTTCCAGACCTTGGTCAAGAACGGAACCA
          K  A  L  R  A  A  G  V  V  V  P  E  T  F  E  K  L  P  L  V  L  S  Q  T  F  Q  T  L  V  K  N  G  T  I ·

2801   TCCAGCTCAAGCCCGAGCCCGAGACTCCCAAGATCCCCATCGATTACTCCTGGGCCCAGGAGCTCGGACTTGTCCGTAAGCCTGCCTCGTTCGTGTCGAC
        · Q  L  K  P  E  P  E  T  P  K  I  P  I  D  Y  S  W  A  Q  E  L  G  L  V  R  K  P  A  S  F  V  S  T ·

2901   CATTTGCGATGACCGTGGTCAGGAGTTGCTCTATGCCGGTATGCGTATCTCGGACGTCTTCAAGGAGGACATTGGTATCGGAGGTGTTCTGTCCTTGCTC
        · I  C  D  D  R  G  Q  E  L  L  Y  A  G  M  R  I  S  D  V  F  K  E  D  I  G  I  G  G  V  L  S  L  L

3001   TGGTTCAAGCGCCGTCTGCCCGACTACGCCTGCAAGTTTATCGAGATGGTTCTCATGCTCACTGCTGATCACGGTCCCGCCGTCTCAGGTGCACACAACA
          W  F  K  R  R  L  P  D  Y  A  C  K  F  I  E  M  V  L  M  L  T  A  D  H  G  P  A  V  S  G  A  H  N  T ·

3101   CCATCGTCACTGCCCGTGCCGGCAAGGATTTGGTTTCGTCGTTGTGCGCAGGTCTTTTGACGATTGGTGACCGCTTCGGAGGTGCCTTGGATGGTGCCGC
        · I  V  T  A  R  A  G  K  D  L  V  S  S  L  C  A  G  L  L  T  I  G  D  R  F  G  G  A  L  D  G  A  A ·

3201   CGAGCAGTTCTCGTCTGCATACGACAAGTCGCTCACGCCCCGTGAGTTTGTCTCTGTGATGCGTAAGCAGAACAAGTTGATTCTCGGTATCGGCCACAAG
        · E  Q  F  S  S  A  Y  D  K  S  L  T  P  R  E  F  V  S  V  M  R  K  Q  N  K  L  I  L  G  I  G  H  K

3301   ATCAAGTCGCGCACGAACCCCGATCTGCGTGTCGAGATCATCAAGGAGTACGCCAAGAAGCACTTCCCCTCGACCCCTGTTCTGGACTATGCCCTTCAGG
          I  K  S  R  T  N  P  D  L  R  V  E  I  I  K  E  Y  A  K  K  H  F  P  S  T  P  V  L  D  Y  A  L  Q  V ·

3401   TGGAGAACATCACGACGTCCAAGAAGGACAACTTGATCTTGAACGTCGATGGAGCGATCGGAATCTTGTTTGTGGATCTGTTGAGAAACTCGGGCGCGTT
        · E  N  I  T  T  S  K  K  D  N  L  I  L  N  V  D  G  A  I  G  I  L  F  V  D  L  L  R  N  S  G  A  F ·

3501   CACGCGTGAGGAGGCTGAGGAGTACATCAAGATTGGAACGTTGAACGGTCTGTTTGTATTGGGTCGCTCGATCGGATTCATTGGACATTACTTGGACCAG
        · T  R  E  E  A  E  E  Y  I  K  I  G  T  L  N  G  L  F  V  L  G  R  S  I  G  F  I  G  H  Y  L  D  Q

3601   AAGAGGCTGAAGCAGGGCTTGTACAGACATCCTTGGGATGATATCTCGTACCTGACCCCCGGCAATGAGCTCGGACGGACGGTTGCCTCGCTGGATTCGA
          K  R  L  K  Q  G  L  Y  R  H  P  W  D  D  I  S  Y  L  T  P  G  N  E  L  G  R  T  V  A  S  L  D  S  I ·

3701   TCAACAAGAAGGCCTAAAGAGGGGACGTTGGAGAAACTGAACGAACTTAGAGAAGAAAAAACAAACACTCATCATCTATCGTTGTACATATTAAATATTA
        · N  K  K  A

3801   AATAACTTTGTGAAGCCCAAAAAAAAAAAAAAAAAAAAAA
```

Figure 2-1

```
1      CTGCAGGCTCGCCCTTCACCATGTCTGCCAAAGCTGTTCGTGAGTATGATGGAAAGCTGCTGTTGGCACACTGGCTCCTGCGCACGCCTATCCCTGCCAC
                       M  S  A  K  A  V  R  E  Y  D  G  K  L  L  L  A  H  W  L  L  R  T  P  I  P  A  T  ·

101    CAGCATCTCTGCCACAGGGTCCAAGTTTGTCCAGCCAGCAACGCGCCTGGCTCACATCGGCATTGACACTGCAGTGTTGAACACGGACAAGACCGTCTTC      ·
        S  I  S  A  T  G  S  K  F  V  Q  P  A  T  R  L  A  H  I  G  I  D  T  A  V  L  N  T  D  K  T  V  F

201    AACCAGCATGTCCAGACCTTGCTTGATAACCTGGAGCAGACCCATCCCTGGCTCTTGACCTCCAAGCTTGTGGCCAAACCAGATCAATTGATCAAGCGCC
        N  Q  H  V  Q  T  L  L  D  N  L  E  Q  T  H  P  W  L  L  T  S  K  L  V  A  K  P  D  Q  L  I  K  R  R  ·

301    GTGGCAAGAGTGGCCTGCTGCTCTTGAACGCGGACTGGGCAGAGGTCAGGACCTGGATCACAGCGCATGCGGGCAAGGATGTTGTTGTTGACTCTGTCGC
        ·  G  K  S  G  L  L  L  L  N  A  D  W  A  E  V  R  T  W  I  T  A  H  A  G  K  D  V  V  V  D  S  V  A  ·

401    GGGTGTGCTCAAGACGTTCTTGGTCGAGCCCTTCATTCCCCACCCAGCCAACACGGAATACTACATCTGCATCAACTCGGACCGCGATGGCGACAACATT
        ·  G  V  L  K  T  F  L  V  E  P  F  I  P  H  P  A  N  T  E  Y  Y  I  C  I  N  S  D  R  D  G  D  N  I

501    CTCTTCACACATGAGGGAGGCATTGAGGTTGGCGACGTCGATGCCAAGGCTTTGAAGCTCCAGGTCAAGGTCGGCGACACTTTCCCCACCACTGCCGCCA
        L  F  T  H  E  G  G  I  E  V  G  D  V  D  A  K  A  L  K  L  Q  V  K  V  G  D  T  F  P  T  T  A  A  I  ·

601    TACAGTCGGCACTGCTCACACACGTCCCTGCCACGAAGCACGACGTCCTCATCGATTTCATCACCCGTCTCTACGCCGTTTACGTCGATCTCCACTTCAC
        ·  Q  S  A  L  L  T  H  V  P  A  T  K  H  D  V  L  I  D  F  I  T  R  L  Y  A  V  Y  V  D  L  H  F  T  ·

701    CTACCTCGAGATCAATCCCTTGGTCGTCCTCGACCCTACCCCCGAACACCCAGCCCAGGTCTACTACTTGGATCTCGCCGCCAAGGTCGATCAGACTGCA
        ·  Y  L  E  I  N  P  L  V  V  L  D  P  T  P  E  H  P  A  Q  V  Y  Y  L  D  L  A  A  K  V  D  Q  T  A

801    GAGTTCGAGGCTGGCCCCAAGTGGGCCTTTGCCAGGGCTCCTCAGAACATTGGACTGGTTGCTGCCGGTTCCCAAGGCGTTGATGCTGGACCACCTATGG
        E  F  E  A  G  P  K  W  A  F  A  R  A  P  Q  N  I  G  L  V  A  A  G  S  Q  G  V  D  A  G  P  P  M  D  ·

901    ATTTCCCTGCTCCTTTCGGTCGTGAGTTGACCAAGGAGGAAGCGTATGTTCAGGAACTGGATTCCAAGACCGGCGCCTCGCTCAAGCTGACGATTCTGAA
        ·  F  P  A  P  F  G  R  E  L  T  K  E  E  A  Y  V  Q  E  L  D  S  K  T  G  A  S  L  K  L  T  I  L  N  ·

1001   CAAGGACGGTCGCATCTGGACTATGGTCGCTGGCGGTGGAGCTTCCGTCGTGTACAGTGATGCCATTGCTGCCTTGGGACAGGCGAACGAGCTTGCTAAC
        ·  K  D  G  R  I  W  T  M  V  A  G  G  G  A  S  V  V  Y  S  D  A  I  A  A  L  G  Q  A  N  E  L  A  N

1101   TATGGAGAGTACTCTGGAGCACCCACCGAGACCCAGACTTATGAATATGCCAAGACGATCCTCGACTTGATGACTCGATCAGCCATCCCCCACCCTCTTG
        Y  G  E  Y  S  G  A  P  T  E  T  Q  T  Y  E  Y  A  K  T  I  L  D  L  M  T  R  S  A  I  P  H  P  L  G  ·

1201   GCAAGGTTCTGATTATTGGAGGTGGTATCGCCAACTTTACAAATGTGGCCTCGACCTTCAAGGGTATCGTCCGTGCCCTGACTGAGTTCAAGCAGCCTTT
        ·  K  V  L  I  I  G  G  G  I  A  N  F  T  N  V  A  S  T  F  K  G  I  V  R  A  L  T  E  F  K  Q  P  L  ·

1301   GATTGCCCACAAGGTTCGCATTTTCGTCCGCCGCGGTGGCCCCAACTATCAGGAGGGTCTTCGCTCGATGCGCCAGCTGGGTGAGACGTTGGGGGTTGAG
        ·  I  A  H  K  V  R  I  F  V  R  R  G  G  P  N  Y  Q  E  G  L  R  S  M  R  Q  L  G  E  T  L  G  V  E

1401   ATCCAGGTCTTTGGTCCTGAGACCCACATTACAGAGATCGTGCCCTTGGCCTTGACTGGAAAACTTTCTGGACTAAACCAGTCTGGGACTGCCACGCCCA
        I  Q  V  F  G  P  E  T  H  I  T  E  I  V  P  L  A  L  T  G  K  L  S  G  L  N  Q  S  G  T  A  T  P  S  ·

1501   GCGCCCATTTGTCCTCTGGAAATCTTCTGCAGGATCAGCTCCTGGGCAACAACACTCCCCTGAACGCTGGATCGCGCGCTTCGTCACCACCACCATTGGA
        ·  A  H  L  S  S  G  N  L  L  Q  D  Q  L  L  G  N  N  T  P  L  N  A  G  S  R  A  S  S  P  P  P  L  E  ·

1601   GGACAGGATGACTTACTTCCAGGACCAGAATGCGGAGTCCTCAGAGTCTAGCCACGACGAGAACACGCCCTTCACGGCCCACACGCGCTCTTTTATTTAC      ·
        D  R  M  T  Y  F  Q  D  Q  N  A  E  S  S  E  S  S  H  D  E  N  T  P  F  T  A  H  T  R  S  F  I  Y

1701   GGCATGCAGCCTCGCGCCGTCCAGGGAATGCTTGATTTTGATTTCATTTGCAAGCGCGAGGTGCCCTCAGTTGCTGCCATGGTCTACCCCTTTGGAGGTG
        G  M  Q  P  R  A  V  Q  G  M  L  D  F  D  F  I  C  K  R  E  V  P  S  V  A  A  M  V  Y  P  F  G  G  A  ·

1801   CCCATGTCCAAAAGTTCTACTGGGGCACTAAGGAGACCCTCCTGCCTGTCTTCACGTCCTTGGATGAGGCTGTTGCCAAATACCCCGAGGTTGACACCGT
        ·  H  V  Q  K  F  Y  W  G  T  K  E  T  L  L  P  V  F  T  S  L  D  E  A  V  A  K  Y  P  E  V  D  T  V  ·
```

Figure 2-2

```
1901  GGTGAACTTTGCCTCTTGCCGTTCCGTTTATGACTCGACCCGCGAGATTTTCAAGCACTCGAAGCAAATCCGCACCATCTCCATCATCGCCGAGGGTGTG
       ·V  N  F  A  S  C  R  S  V  Y  D  S  T  R  E  I  F  K  H  S  K  Q  I  R  T  I  S  I  I  A  E  G  V

2001  CCAGAGCGCCGCGCTCGTCAAATTTTGTGGGAGGCCAAAGAGCGTAATGTCTTGGTCATTGGACCTGCCACTGTCGGAGGCATCAAGCCCGGCTGCTTCA
       P  E  R  R  A  R  Q  I  L  W  E  A  K  E  R  N  V  L  V  I  G  P  A  T  V  G  G  I  K  P  G  C  F  K·

2101  AGATTGGAAACACTGGAGGAATGATGGATAATATTGTATCCTCAAAGCTCTACCGCGCAGGATCCGTGGCTTATGTGTCCAAGTCTGGAGGCATGTCCAA
       ·I  G  N  T  G  G  M  M  D  N  I  V  S  S  K  L  Y  R  A  G  S  V  A  Y  V  S  K  S  G  G  M  S  N·

2201  CGAGTTGAACAACATTATCTCTCGCACCACCGATGGTGTCTACGAGGGAGTTGCCATTGGAGGGGACCGCTACCCTGGTTCGACTTTTATTGACCACTTG
       ·E  L  N  N  I  I  S  R  T  T  D  G  V  Y  E  G  V  A  I  G  G  D  R  Y  P  G  S  T  F  I  D  H  L

2301  CTTCGCTACGAGAAGGATCCCGGGTGCAAGATGCTTGTCTTGTTGGGCGAGGTCGGAGGTGTTGAAGAATACAAAGTCTGTGAGGCGATCAAGAACGGAG
       L  R  Y  E  K  D  P  G  C  K  M  L  V  L  L  G  E  V  G  G  V  E  E  Y  K  V  C  E  A  I  K  N  G  A·

2401  CCATCCGCAAGCCCGTGATTGCCTGGTGCATTGGTACCTGCGCCAAGATGTTTGCCACCGAGGTCCAGTTTGGACATGCTGGTGCCCTTGCCCAGTCAGA
       I  R  K  P  V  I  A  W  C  I  G  T  C  A  K  M  F  A  T  E  V  Q  F  G  H  A  G  A  L  A  Q  S  D·

2501  TCTTGAGACAGCTGATGCCAAGAACCGTGCCCTTCGTGCCGCTGGCGTGATCGTCCCAGAGACGTTTGAAATGCTCCCCTTGGTTTTGAGTCAGACCTAC
       L  E  T  A  D  A  K  N  R  A  L  R  A  A  G  V  I  V  P  E  T  F  E  M  L  P  L  V  L  S  Q  T  Y

2601  CAGGCTCTCGTCAAGAAGGGCGTCGTCATTGTCCGCTCTGAGCCCGAGACACCCAAGATCCCTATTGACTACTCCTGGGCCCAGGAGTTGGGTCTTGTCC
       Q  A  L  V  K  K  G  V  V  I  V  R  S  E  P  E  T  P  K  I  P  I  D  Y  S  W  A  Q  E  L  G  L  V  R·

2701  GCAAGCCAGCCTCGTTTGTGTCGACTATTTGTGATGACCGTGGCCAGGAACTGCTCTATGCTGGCATGCGCATCTCGGATGTGTTCAAGGAGGACATCGG
       ·K  P  A  S  F  V  S  T  I  C  D  D  R  G  Q  E  L  L  Y  A  G  M  R  I  S  D  V  F  K  E  D  I  G·

2801  TATCGGTGGTGTTCTCTCCCTGCTCTGGTTCAAGCGCCGTCTCCCCGACTATGCCTGCAAGTTTATCGAGATGGTCCTCATGCTCACAGCTGATCATGGT
       I  G  G  V  L  S  L  L  W  F  K  R  R  L  P  D  Y  A  C  K  F  I  E  M  V  L  M  L  T  A  D  H  G

2901  CCTGCTGTTTCGGGTGCTCATAACACGATTGTGACCGCTCGTGCAGGCAAGGATCTTGTTTCGTCTCTGTGCGCGGGTCTGTTGACGATTGGAGACCGTT
       P  A  V  S  G  A  H  N  T  I  V  T  A  R  A  G  K  D  L  V  S  S  L  C  A  G  L  L  T  I  G  D  R  F·

3001  TTGGAGGCGCATTGGACGGAGCCGCTGAGCAGTTCTCGTCTGCATACGACAAGTCGCTCTCGCCCCGCGAGTTTGTGTCGTCGATGAGAAAGCAGAACAA
       ·G  G  A  L  D  G  A  A  E  Q  F  S  S  A  Y  D  K  S  L  S  P  R  E  F  V  S  S  M  R  K  Q  N  K·

3101  GCTGATTTTTGGGTATTGGCCACAAGATCAAGTCGCGCACGAACCCTGATTTGCGTGTGGAGATTATTAAGAACTACGCCAAGGCGCACTTCCCTGCCACG
       ·L  I  L  G  I  G  H  K  I  K  S  R  T  N  P  D  L  R  V  E  I  I  K  N  Y  A  K  A  H  F  P  A  T

3201  CCTGTGCTGGATTATGCCCTGGCTGTGGAGACCATCACCACCTCCAAGAAGGATAACTTGATCCTGAACGTGGATGGAGCCATTGGTATCTTGTTTGTGG
       P  V  L  D  Y  A  L  A  V  E  T  I  T  T  S  K  K  D  N  L  I  L  N  V  D  G  A  I  G  I  L  F  V  D·

3301  ACTTGCTGAGAAACTCGGGAGCGTTCACGCGCGAGGAGGCAGAGGAATACATCAAGATTGGAACTTTGAATGGTCTCTTTGTCCTGGGCCGGACGATTGG
       ·L  L  R  N  S  G  A  F  T  R  E  E  A  E  E  Y  I  K  I  G  T  L  N  G  L  F  V  L  G  R  T  I  G·

3401  ATTCATTGGACACTTCTTGGACCAGAAGAGGCTGAAGCAGGGATTGTACAGACACCCTTGGGACGATATCTCGTACCTGACTCCTGGTAACGAGCTCGGA
       ·F  I  G  H  F  L  D  Q  K  R  L  K  Q  G  L  Y  R  H  P  W  D  D  I  S  Y  L  T  P  G  N  E  L  G

3501  CGGACAGTTGCGTCGCTGGACTCCATCAACAAGAAGGCTGCGTAAGCAGTCGTTATACATAGCATCATCTTTTTGTTTTTCTCGTGTGTGCTCGTGTCTT
       R  T  V  A  S  L  D  S  I  N  K  K  A  A

3601  ATAAAGACAGATGTCCATCCTATTTTCTTTGAACAAAAAAAAAAAAAAAAAAAAAAAAAAAAAAAAAAAAAAAAAAAAAMAAAAA
```

*Figure 3-1*

```
            1                                                                                                    100
ACL1    ATGTCTGCTAAAGCCGTTCGCGAATACGATGGAAAGCTGCTCTTGGCCCACTGGCTTCACCGTGTTGCCGTGCCCGAATCAGAGACCGCAGGATCAGCAA
ACL2    ATGTCTGCCAAAGCTGTTCGTGAGTATGATGGAAAGCTGCTGTTGGCACACTGGCTCC-------TGC-GCACGCCTATCCCTGCCACCAGCATCT-CTG
            101                                                                                                  200
ACL1    CAACGGGATCCAAGTTCGTCCAGCCCACCACCCGCCTTGCCCACATCTCCATCGACACCTCGCTCTTGCA---GGACAAGACCCAGTTCGATCAGCACGT
ACL2    CCACAGGGTCCAAGTTTGTCCAGCCAGCAACGCCGCCTGGCTCACATCGGCATTGACACTGCAGTCGTTGAACACGGACAAGACCGTCTTCAACCAGCATGT
            201                                                                                                  300
ACL1    CCGCTCGACCTTGGATCAGCTCGAGGTCTCGCACCCTTGGCTGTTGACCAACAAGCTGGTCGCCAAGCCTGACCAGTTGATCAAGCGTCGTGGAAAGAGC
ACL2    CCAGACCTTGCTTGATAACCTGGAGCAGACCCATCCCTGGCTCTTGACCTCCAAGCTTGTGGCCAAACCAGATCAATTGATCAAGCGCCGTGGCAAGAGT
            301                                                                                                  400
ACL1    GGCTTGCTGCTCTTGAACGCCGAATGGGCTGAGGCTAGAGCCTGGATCGAGAAGCACGCGGCCAAGGACGTCCTTGTGGACTCCGTTCCCGGTGTTCTCA
ACL2    GGCCTGCTGCTCTTGAACGCCGACTGGGCAGAGGTCAGGACCTGGATCACAGCGCATGCGGGCAAGGATGTTGTTGTTGACTCTGTCGCCGGTGTGCTCA
            401                                                                                                  500
ACL1    AGACCTTCCTCGTCGAGCCCTTCATTCCCCACCCTTCTAACACTGAGTACTACATCTGCATCAACTCAGATCGTGATGGTGACAACATCCTCTTCACGCA
ACL2    AGACCTTCTTGGTCGAGCCCTTCATTCCCCACCCACGCAACACGGAATACTACATCTGCATCAACTCCGACCGCGATGGCGACAACATTCTCTTCACACA
            501                                                                                                  600
ACL1    CGAGGGAGGTATCGAGGTCGGAGATGTTGATGCCAAGGCATTGAAGCTCCAGGTGAAGGTTCAGGACGCCTTCCCCACCGCAGAGGCCATTCGCTCGGCT
ACL2    TGAGGGAGGCATTGAGGTTGGCGACGTCGATGCCAAGGCTTTGAAGCTCCAGGTCAAGGTCGGCGACACTTTCCCCACCACTGCCGCCATACAGTCGGCA
            601                                                                                                  700
ACL1    CTCCTGGTCCATGTCCCTGAGGCCAAGCACGATGTTCTTGTTGACTTTATCACTCGCCTCTATGCTGTTTACATCGACCTCCACTTCACCTACCTTGAGA
ACL2    CTGCTCACACACGTCCCTGCCACGAAGCACGACGTCCTCATCGATTTCATCACCCGTCTCTACGCCGTTTACGTCGATCTCCACTTCACCTACCTCGAGA
            701                                                                                                  800
ACL1    TCAACCCCTTGGTCGTCTTGGATCCCACAGAGGACGAGCCTGCTCGTGTCTACTACCTCGACCTGGCTGCTAAGCTCGATCAGACTGCAGAGTTCGAGGC
ACL2    TCAATCCCTTGGTCGTGCTCGACCCTAGCCCCGAACACCCAGCCCAGGTCTACTACTTGGATCTCGCCGCCAAGGTCGATCAGACTGCGAGTTCGAGGC
            801                                                                                                  900
ACL1    TGGTCCCAAGTGGGCCATCGCCAGAGCTCCTCAGAACATTGGAATTGCTGGCGTCA-TCCCCACCACTGTTGGCGCTGATGCTGGCCCTGGCATGGATTT
ACL2    TGGCCCCAAGTGGGCCTTTGCCAGGGGTCCTCAGAACATTGGACTGGTTGCTGCCGGTTCCCAA-------GGCGTTGATGCTGGACCACCTATGGATTT
            901                                                                                                 1000
ACL1    CCCCGCACCTTTGGGTCGTGAATTGACCAAGGAGGAGCCCTATGTTCAGGAGCTGGACTCTAAGACCGGTGCTTCGCTCAAGCTCACCATCCTGAACAAG
ACL2    CCCTGCTCCTTTCGGTCGTGAGTTGACCAAGGAGGAAGCGTATGTTCAGGAACTGGATTCCAAGACCGGCGCCTCGCTCAAGCTGACGATTCTGAACAAG
           1001                                                                                                 1100
ACL1    GATGGACGCATCTGGACCATGGTTGCTGGAGGCGGTGCCTCTGTCGTTTACAGTGATGCCATCGCTGCCCTTGGCCAGGCTGACGAGCTCGCCAACTACG
ACL2    CACCGGTCCCATCTGGACTATGCTCGCTGGCGGTGGAGCTTCCGTCGTGTACAGTGATGCCATTGCTGCCTTGGCACAGGCCGAACGAGCTTGCTAACTATG
           1101                                                                                                 1200
ACL1    GAGAGTACTCTGGTGCCCCCACCGAGACCCAGACCTATGAATACGCCAAGACCATCCTTGACCTTATGACCCGCTCTGCCACCCCTCACCCCGAGGGCAA
ACL2    GAGAGTACTCTGGAGCACCCACCGAGACCCAGACTTATGAATATGCCAAGACGATCCTCGACTTGATGACTCGATCAGCCATCCCCCACCCTCTTGGCAA
           1201                                                                                                 1300
ACL1    GGTCCTCATCATTGGAGGAGGTATCGCCAACTTCACTAACGTCGCCTCGACCTTCAAGGGAATTGTCCGCCGCTCTTACCGAGTTTAAACAGCCCTTGATC
ACL2    GGTTCTGATTATTGGAGGTGGTATCGCCAACTTTACAAATGTGGCCTCGACCTTCAAGGGTATCGTCCGTGCCCTGACTGAGTTCAAGCAGCCTTTGATT
           1301                                                                                                 1400
ACL1    GCCCACAAGGTCCGCATCTTTGTCCGTCGTGGTGGTCCCAACTACCAGGAGGGTCTTCGCTCCATGCGTCAACTCGGCGAGTCCTTGGGAGTTGAGATCC
ACL2    GCCCACAAGGTTCGCATTTTCGTCCGCCGCGGTGGCCCCAACTATCAGGAGGGTCTTCGCTCCGATGCGCCAGCTGGGTGAGACGTTGGGGGTTGAGATCC
           1401                                                                                                 1500
ACL1    AGGTCTTTGGACCCGAGACCCACATCACCGAGATTGTTCCTCTGCCCTTGACTGGACGCTCTTCCG-AC--AAGTTGCCTGCCACCAACGCCAACAACGG
ACL2    AGGTCTTTGGTCCTGAGACCCACATTACAGAGATCCTCCCCCTTGGCCTTGACTGGAAAACTTTCTGCAGTAAACCAGTCTGGGACTGCCAGCCCACGGC
           1501                                                                                                 1600
ACL1    CAGCGCCTCGTCCGGAAACCTCCTTCAGGATCAGCTCTTGGGCACCAACAGCAACCTCAACACCCCTGTTCCCACTGCCCCCGTCTCCCGTGCTGGCACT
ACL2    CCATTTGTCCTCTGGAAATCTTCTGCAGGATCAGCTCCTGGGCAACAACACTCCCCTGAACGCT--GGATCGGCGCG--CTTCGTCACCA----------
           1601                                                                                                 1700
ACL1    CGTCCCGCCAGCGAGAGGATGACTTACTTCACGGACGCAGACGCAAAG------AAGTCG-GCCACGGATTCCAACGTTCCCTTCACTGCCCACACTCGCT
ACL2    CCACCATTGGAGGACAGGATGACTTACTTCCAGGACCAGAATGCCGAGTCCTCAGAGTCTAGCCACGACGAGAACACGCCCTTCACGGCCCACACCGCT
           1701                                                                                                 1800
ACL1    CGTTCATCTACGGAATGCAGCCCCGTGCTGTTCAGGGAATGCTCGACTTTGATTTCATCTGCAAGCGGTGAGGTCCCCTCGGTCGCAGCCATGATCTACCC
ACL2    CTTTTATTTACGGGCATGCAGCCTGCGCGCGTCCAGGGAATGCTTGATTTTGATTTCATTTGCAAGCGCGAGGTCCCCTCAGTTGCTGCCATGGTCTACCC
           1801                                                                                                 1900
ACL1    CTTTGGCGGTGCTCACGTTCAGAAGTTCTACTGGGGCACCAAGGAGACTCTCTTGCCCGTTTACACTACTCTGGAGGAGGCCACTGCCAAGTTCCCCGAG
ACL2    CTTTGGAGGTGCCCATGTCCAAAAGTTCTACTGGGGCACTAAGGAGACCCTCCTGCCCTGTCTTCACGTGCCTTGGATGAGGCTGTTGCCAAATACCCCGAG
```

*Figure 3-2*

```
            1901                                                                                              2000
ACL1  GTTGATACCGTCGTCAACTTTGCCTCGTGCCGCTCTGTTTACCAGTCCACGGTTGATATCCTCAGTCACTCTGACCAGATCAAGACGATCTCGATCATTG
ACL2  GTTGACACCGTCGTGAACTTTGCCTCTTGCCGTTCCGTTTATGACTCGACCCGCGAGATTTTCAAGCACTCGAAGCAAATCCGCACCATCTCCATCATCG
            2001                                                                                              2100
ACL1  CCGAGGGTGTCCCCGAGCGTCGTGCTCGCCAGATCCTCTGGGAGGCCAAGGCCAAGAACGTGCTCGTCATCGGACCAGCCACTGTCGGAGGCATCAAGCC
ACL2  CCGAGGGTGTGCCAGAGCGCCGCGCTCGTGAAATTTTGTGGGAGGCCAAAGAGCGTAATGTCTTGGTCATTGGACCTGCCACTGTCGGAGGCATCAAGCC
            2101                                                                                              2200
ACL1  CGGCTGCTTCAAGATCGGAAACACTGGAGGTATGATGGACAACATTGTCTCGTCCAAGTTGTACCGCGCCGGTTCTGTTGCCTACGTCTCCAAGTCTGGC
ACL2  CGGCTGCTTCAAGATTGGAAACACTGGAGGAATGATGGATAATATTGTATCCTCAAAGCTCTACCGCGCAGGATCCGTGGCTTATGTGTCCAAGTCTGGA
            2201                                                                                              2300
ACL1  GGTATGTCCAACGAGCTGAACAACATCATCTCCCGCACCACTGACGGTGTCTACGAGGGAGTCGCCCATCGGAGGAGACCGTTACCCTGGATCGACCTTCA
ACL2  GGCATGTCCAACGAGTTGAACAACATTATCTCTCGCACCACCGATGGTGTCTACGAGGGAGTTGCCCATTGGAGGGGACCGCTACCCTGGTTCGACTTTTA
            2301                                                                                              2400
ACL1  TCGACCACTTGCTTCGCTATGAGCGGACCCGAACTGCAAGATGTTCGTCTTGCTCGGAGAGGTCGGAGGTGTCGACGACTACAAGGTCTGTGAGGCGAT
ACL2  TTGACCACTTGCTTCGCTACGAGAAGGATCCCGGGTGCAAGATGCTTGTCTTGTTGGGCGAGGTCGGAGGTGTTGAAGAATACAAAGTCTGTGAGGCGAT
            2401                                                                                              2500
ACL1  CAAGAACGGGACCATCCGCAAGCCCGTGATTGCCTGGTGCATCGGTACCTGCGCCAAGATGTTTGCCACCGAGGTCCAGTTCGGACACGCCGGTGCCTTG
ACL2  CAAGAACGGAGCCATCCGCAAGCCCGTGATTGCCTGGTGCATTGGTACCTGCGCCAAGATGTTTGCCACCGAGGTCCAGTTTGGACATGCTGGTGCCCTT
            2501                                                                                              2600
ACL1  GCCCAGTCCGATCTCGAGACTGCCGATGCCAAGAACAAGGGCTCTCCGCGCCGCTGGTGTGGTCGTTCCCGAGACCTTTGAGAAGTTGCCCTTGGTCTTGA
ACL2  GCCCAGTCAGATCTTGAGACAGCTGATGCCAAGAACCGTGCCCTTCGTGCCGCTGGCGTGATCGTCCCAGAGACGTTTGAAATGCTCCCCTTGGTTTTGA
            2601                                                                                              2700
ACL1  GCCAGACCTTCCAGACCTTGGTCAAGAACGGAACCATCCAGCTCAAGCCCGAGCCCGAGACTCCCAAGATCCCCATCGATTACTCCTGGGCCCAGGAGCT
ACL2  GTCAGACCTACCAGGCTCTCGTCAAGAAGGGCGTCGTCATTGTCCGCTCTGAGCCCGAGACACCCAAGATCCCTATTGACTACTCCTGGGCCCAGGAGTT
            2701                                                                                              2800
ACL1  CGGACTTGTCGCGTAAGCCTGCCTCGTTCGTGTCGACCATTTGCGATGACCGTGGTCAGGAGTTGCTCTATGCCGGTATGCGTATCTCGGACGTCTTCAAG
ACL2  GGGTCTGTCCGCAAGCCAGCCTCGTTTGTGTCGACTATTTGTGATGACCGTGGCCAGGAACTGCTCTATGCTGGCATGCGCATCTCGGATGTGTTCAAG
            2801                                                                                              2900
ACL1  GAGGACATTGGTATCGGAGGTGTTCTGTCCTTGCTCTGGTTCAAGCGCCGTCTGCCCGACTACGCCTGCAAGTTTATCGAGATGGTTCTCATGCTCACTG
ACL2  GAGGACATCGGTATCGGTGGTGTTCTCTCCCTGCTCTGGTTCAAGCGCCGTCTCCCCGACTATGCCTGCAAGTTTATCGAGATGGTCCTCATGCTCACAG
            2901                                                                                              3000
ACL1  CTGATCACGGTCCCGCCGTCTGAGGTGGACACAACACCCATCGTCACTGCCCGTGCCGGCAAGGATTTGGTTTCGTCGTTGTGCGCAGGTCTTTTGACGAT
ACL2  CTGATCATGGTCCTGCTGTTCGGGTGCTCATAACACCATTGTGACCGCTCGTGCAGGCAAGGATCTTGTTTCGTCTCTGTGCGCGGGTCTCTTGACGAT
            3001                                                                                              3100
ACL1  TGGTGACCGCTTCGGAGGTGCCTTGGATGGTGCCGCCGAGCAGTTCTCGTCTGCATACGACAAGTCGCTCACGCCCCGTGAGTTTGTCTCTGTGATGCGT
ACL2  TGGAGACCGTTTTGGAGGCGCATTGGACGGAGCCGCTGAGCAGTTCTCGTCTGCATACGACAAGTCGCTCTCGCCCCGCGAGTTTGTCGTCGATGAGA
            3101                                                                                              3200
ACL1  AAGCAGAACAAGTTGATTCTCGGTATCGGCCCACAAGATCAAGTCGCGCACGAACCCCGATCTGCGTGTCGAGATCATCAAGGAGTACGCCAAGAAGCACT
ACL2  AAGCAGAACAAGCTGATTTTGGGTATTGGCCACAAGATCAAGTCGCGCACGAACCCTGATTTGCGTGTGGAGATTATTAAGAACTACGCCAAGGCGCACT
            3201                                                                                              3300
ACL1  TCCCCTGGACCCCTGTTCTGGACTATGCCCTTCAGGTGGAGAACATCACGACGTCCAAGAAGGACAACTTGATCTTGAACGTCGATGGAGCGATCGGAAT
ACL2  TCCCTGCCACGCCTGTCGTGGATTATGCCCTGGCTGTGGAGACCATCACCACCTCCAAGAAGGATAACTTGATCCTGAACGTCGATGGAGCCATTGGTAT
            3301                                                                                              3400
ACL1  CTTGTTTGTGGATCTGTTGAGAAAGTCGGGCGCGTTCACGCGTGAGGAGGCTGAGGAGTACATCAAGATTGGAACCTTGAACGGTCTGTTTGTATTGGGT
ACL2  CTTGTTTGTGGACTTGCTGAGAAAACTCGGGAGCGTTCACGCGCGAGGAGGCAGAGGAATACATCAAGATTGGAACTTTGAATGGTCTCTTTGTCCTGGGC
            3401                                                                                              3500
ACL1  CGCTCGATCGGATTCATTGGACATTACTTGGACCAGAAGAGGCTGAAGCAGGGCTTGTACAGACATCCTTGGGATGATATCTCGTACCTGACCCCCGGCA
ACL2  CGGACGATTGGATTCATTGGACACTTCTTGGACCAGAAGAGGCTGAAGCAGGGATTGTACAGACACCCTTGGGACGATATCTCGTACCTGACTCCTGGTA
            3501                                        3556
ACL1  ATGAGCTCGGACGGACGGTTGCCTCGCTGGATTCGATCAACAAGAAGGCC---TAA
ACL2  ACGAGCTCGGACGGACAGTTGCGTCGCTGGACTCCATCAACAAGAAGGCTGCGTAA
```

Figure 4

```
          1                                                                                                     100
ACL1  MSAKAVREYDGKLLLAHWLHRVAVPESETAGSATTGSKFVQPTTRLAHISIDTSLL-QDKTQFDQHVRSTLDQLEVSHPWLLTNKLVAKPDQLIKRRGKS
ACL2  MSAKAVREYDGKLLLAHWLLRTPIP---ATSISATGSKFVQPATRLAHIGIDTAVLNTDKTVFNQHVQTLLDNLEQTHPWLLTSKLVAKPDQLIKRRGKS 101                                                                                                   200
ACL1  GLLLLNAEWAEARAWIEKHAAKDVLVDSVPGVLKTFLVEPFIPHPSNTEYYICINSDRDGDNILFTHEGGIEVGDVDAKALKLQVKVQDAFPTAEAIRSA
ACL2  GLLLLNADWAEVRTWITAHAGKDVVVDSVAGVLKTFLVEPFIPHPANTEYYICINSDRDGDNILFTHEGGIEVGDVDAKALKLQVKVGDTFPTTAAIQSA 201                                                                                                   300
ACL1  LLVHVPEAKHDVLVDFITRLYAVYIDLHFTYLEINPLVVLDPTEDEPARVYYLDLAAKLDQTAEFEAGPKWAIARAPQNIGIAGVIPTTVGADAGPGMDF
ACL2  LLTHVPATKHDVLIDFITRLYAVYVDLHFTYLEINPLVVLDPTPEHPAQVYYLDLAAKVDQTAEFEAGPKWAFARAPQNIGLVAAG--SQGVDAGPPMDF 301                                                                                                   400
ACL1  PAPFGRELTKEEAYVQELDSKTGASLKLTILNKDGRIWTMVAGGGASVVYSDAIAALGQADELANYGEYSGAPTETQTYEYAKTILDLMTRSATPHPEGK
ACL2  PAPFGRELTKEEAYVQELDSKTGASLKLTILNKDGRIWTMVAGGGASVVYSDAIAALGQANELANYGEYSGAPTETQTYEYAKTILDLMTRSAIPHPLGK 401                                                                                                   500
ACL1  VLIIGGGIANFTNVASTFKGIVRALTEFKQPLIAHKVRIFVRRGGPNYQEGLRSMRQLGESLGVEIQVFGPETHITEIVPLALTGRSS-DNLAATNANNG
ACL2  VLIIGGGIANFTNVASTFKGIVRALTEFKQPLIAHKVRIFVRRGGPNYQEGLRSMRQLGETLGVEIQVFGPETHITEIVPLALTGKLSGLNQSGTATPSA 501                                                                                                   600
ACL1  SASSGNLLQDQLLGTNSNLNTPVPTAPVSRAGTPPASERMTYFTDADAKKVG--HDSNVPFTAQTRSFIYGMQPRAVQGMLDFDFICKREVPSVAAMIYP
ACL2  HLSSGNLLQDQLLGNNTPLNAGSRAS-----SPPPLEDRMTYFQDQNAESSESSHDENTPFTAHTRSFIYGMQPRAVQGMLDFDFICKREVPSVAAMVYP 601                                                                                                   700
ACL1  FGGAHVQKFYWGTKETLLPVYITEEEATAKFPEVDTVVNFASCRSVYQSTVDILSHSDQIKTISIIAEGVPERRARQILWEAKAKNVLVIGPATVGGIKP
ACL2  FGGAHVQKFYWGTKETLLPVFTSLDEAVAKYPEVDTVVNFASCRSVYDSTRELFKHSKQIRTISIIAEGVPERRARQILWEAKERNVLVIGPATVGGIKP 701                                                                                                   800
ACL1  GCFKIGNTGGMMDNIVSSKLYRAGSVAYVSKSGGMSNELNNIISRTTDGVYEGVAIGGDRYPGSTFIDHLLRYERDPNCKMLVLLGEVGGVEEYKVCEAI
ACL2  GCFKIGNTGGMMDNIVSSKLYRAGSVAYVSKSGGMSNELNNIISRTTDGVYEGVAIGGDRYPGSTFIDHLLRYEKDPGCKMLVLLGEVGGVEEYKVCEAI 801                                                                                                   900
ACL1  KNGTIRKPVIAWCIGTCAKMFATEVQFGHAGALAQSDLETADAKNKALRAAGVVVPETFEKLPLVLSQTFQTLVKNGTIQLKPEPETPKIPIDYSWAQEL
ACL2  KNGAIRKPVIAWCIGTCAKMFATEVQFGHAGALAQSDLETADAKNRALRAAGVIVPETFEMLPLVLSQTYQALVKKGVVIVRSEPETPKIPIDYSWAQEL 901                                                                                                   1000
ACL1  GLVRKPASFVSTICDDRGQELLYAGMRISDVFKEDIGIGGVLSLLWFKRRLPDYACKFIEMVLMLTADHGPAVSGAHNTIVTARAGKDLVSSLCAGLLTI
ACL2  GLVRKPASFVSTICDDRGQELLYAGMRISDVFKEDIGIGGVLSLLWFKRRLPDYACKFIEMVLMLTADHGPAVSGAHNTIVTARAGKDLVSSLCAGLLTI 1001                                                                                                  1100
ACL1  GDRFGGALDGAAEQFSSAYDKSLTPREFVSVMRKQNKLILGIGHKIKSRTNPDLRVEIIKEYAKKHFPSTPVLDYALQVENITTSKKDNLILNVDGAIGI
ACL2  GDRFGGALDGAAEQFSSAYDKSLSPREFVSSMRKQNKLILGIGHKIKSRTNPDLRVEIIKNYAKAHFPATPVLDYALAVETITTSKKDNLILNVDGAIGI 1101                                                              1184
ACL1  LFVDLLRNSGAFTREEAEEYIKIGTLNGLFVLGRSIGFIGHYLDQKRLKQGLYRHPWDDISYLTPGNELGRTVASLDSINKKA-
ACL2  LFVDLLRNSGAFTREEAEEYIKIGTLNGLFVLGRTIGFIGHFLDQKRLKQGLYRHPWDDISYLTPGNELGRTVASLDSINKKAA
```

Figure 5-1

```
              1                                                                                                        100
    MaACL1    MSAKAVREYDGKLLLAHWLHRVAVPESETAGSATTGSKFVQPTTRLAHISIDTSLL-QDKTQFDQHVRSTLDQLEVSHPWLLTNKLVAKPDQLIKRRGKS
    MaACL2    MSAKAVREYDGKLLLAHWLLRTPIP---ATSISATGSKFVQPATRLAHIGIDTAVLNTDKTVFNQHVQTLLDNLEQTHPWLLTSKLVAKPDQLIKRRGKS
  U.maydis    MSSKAIREFDAKLLVNYWLPRSPLAH--AD--LKVNADFVAPAPKVAQIAWDPVTN-------------SITDASQLPAWVQSSKLVAKPDQLIKRRGKA
M.musculus    MSAKAISEQTGKELLYKYICTTSAIQN--------------RFKYARVTPDTDWA----------------HLLQDHPWLLSQSLVVKPDQLIKRRGKL
  H.sapiens   MSAKAISEQTGKELLYKFICTTSAIQN--------------RFKYARVTPDTDWA----------------RLLQDHPWLLSQNLVVKPDQLIKRRGKL
D.melanogaster MSAKAITEASGKDILNRHLNTHGAGAA--------------TCRFSTVNSTTDWS----------------KLAVDHPWLLTTPLVCKPDQLIKRRGKL
  C.elegans   MSAKAVSELSGKEVLYKYFESTGIVSA--------------PHAFHVKAGDKFSD----------------VAAKYEWLAQDNKGVIKPDQLIKRRGKL
              101                                                                                                      200
    MaACL1    GLLLLNAEWAEARAWIEKHAAKDVLVDSVPGVLKTFLVEPFIPHPSNTEYYICINSDRDGDNILFTHEGGIEVGDVDAKALKLQVKVQDAFPT--AEAIR
    MaACL2    GLLLLNADWAEVRTWITAHAGKDVVVDSVAGVLKTFLVEPFIPHPANTEYYICINSDRDGDNILFTHEGGIEVGDVDAKALKLQVKVGDTFPT--TAAIQ
  U.maydis    GLLKLNCDWADAKTWIQERAGKAQKVETVTGTLNNEIVEPFCPHPADTEFYVCINSAREGDWILFTHEGGVDVGDVDAKALKLLIPADPAAPFPKREEWT
M.musculus    GLVGVNLSLDGVKSWLKPRLGHEATVGKAKGFLKNFLIEPFVPHSQAEEFYVCIYATREGDYVLFHHEGGVDVGDVDAKAQKLLVGVDEKLNTEDIKRHL
  H.sapiens   GLVGVNLTLDGVKSWLKPRLGQEATVGKATGFLKNFLIEPFVPHSQAEEFYVCIYATREGDYVLFHHEGGVDVGDVDAKAQKLLVGVDEKLNPEDIKKHL
D.melanogaster GLIGVKKNFEQVKQWIGERLNKDQKIGNAVGKLRNFIIEPFVPHTDAEEMYVCLYSHRAADTILFYHQGGVDIGDVDAKAVKLDVPVNSSLSLADVKSKL
  C.elegans   GLVKIGSPKE-LEAWFGKTANSYVKVGQTEGRLHTFIVEPFCAHTENEEMYIALYSERCRDVIMFYEQGGVDIGDVEEKARSVHVPVQLDDNAMSISERE
              201                                                                                                      300
    MaACL1    SALLVHVPEAKHDVLVDFITRLYAVYIDLHFTYLEINPLVVLDPTEDEPARVYYLDLAAKLDQTAEFEACGPKWAIARAPQNIGIAGVIPT-TVGADAGPG
    MaACL2    SALLTHVPATKHDVLIDFITRLYAVYVDLHFTYLEINPLVVLDPTPEHPAQVYYLDLAAKVDQTAEFEACGPKWAFARAPQNIGLVAAG---SQGVDAGPP
  U.maydis    STLLGGVPAAKREVLTDFLIRLYSVVDLHFAYLEINPLVATD----D-GQIAYLDMAAKLDQTADFICGPKWAIARDPSIYLGASAGASGNKGEDRGPP
M.musculus    LVHAPED---KKEVLASFISGLFNFYEDLYFTYLEINPLVVTKDG-----VYILDLAAKVDATADYICKVKWG------------------------------D
  H.sapiens   LVHAPED---KKEILASFISGLFNFYEDLYFTYLEINPLVVTKDG-----VYVLDLAAKVDATADYICKVKWG------------------------------D
D.melanogaster LKEVKDAG--TKERIAKFVSALYTTYVDLYFTYLEINPLVVTADN------LYILDLAAKLDSTADFICRPKWG------------------------------E
  C.elegans   LGVLLGPCS-DKDDIRKEVRSLYEAYKALHFTYLEINPFVLTNGK------IHILDLAAKLDETASFLCSDKWSGRNA----------------SARIAPT
              301                                                                                                      400
    MaACL1    MDFPAPFGRELTKEEAYVQELDSKTGASLKLTILNKDGRIWTMVAGGGASVVYSDAIAALGQADELANYGEYSGAPTETQTYEYAKTILDLMTRSATPHP
    MaACL2    MDFPAPFGRELTKEEAYVQELDSKTGASLKLTILNKDGRIWTMVAGGGASVVYSDAIAALGQANELANYGEYSGAPTETQTYEYAKTILDLMTRSAIPHP
  U.maydis    MYWPAPFGRDLTKEEAYIAKLDAGTGASLKLTVLNPTGRIWTMVAGGGASVVYSDAIAAHGYAHELANYGEYSGAPSEGQTFEYAKTLLDLMTRGEVNP-
M.musculus    IEFPPPFGREAYPEEAYIADLDAKSGASLKLTLLNPKGRIWTMVAGGGASVVYSDTICDLGGVNELANYGEYSGAPSEQQTYDYAKTIISLMTR-EKHP-
  H.sapiens   IEFPPPFGREAYPEEAYIADLDAKSGASLKLTLLNPKGRIWTMVAGGGASVVYSDTICDLGGVNELANYGEYSGAPSEQQTYDYAKTIISLMTR-EKHP-
D.melanogaster IDYPPPFGRDAYPEEAYIADLDAKSGASLKLTILNRNGRIWTMVAGGGASVIYSDTICDLGGASELANYGEYSGAPSEQQTYEYAKTIINLMTSSPKHP-
  C.elegans   LEFPAPFGRDLTSEEQYISDMDAKTGASLKLTLLNRKGRVWTMVAGGGASVVFTDTVCDLGGSSELANYEYSGDPSEAQTYEYAKTILSVMTEGAPRP-
              401                                                                                                      500
    MaACL1    EGKVLIIGGGIANFTNVASTFKGIVRALTEEFKQPLIAHKVRIEVRRGGPNYQEGLRSMRQLGESLGVEIQVFGPETHITEIVPLALTGRSS-DNLAATNA
    MaACL2    LGKVLIIGGGIANFTNVASTFKGIVRALTEEFKQPLIAHKVRIEVRRGGPNYQEGLRSMRQLGETLGVEIQVFGPETHITEIVPLALTGKLSGLNQSGTAT
  U.maydis    QGKLLIIGGGIANFTNVASTFKGIIRALKEYKLSLEAKHGVRIFVRRGGPNYQEGLKAMRLLGEDLGVEIQVFGPETHITDIVPLALGVKTFEEVTLASQQ
M.musculus    EGKILIIGGSIANFTNVAATFKGIVRAIRDYQGCPLKEHEVTIFVRRGGPNYQEGLRVMGEVGKTTGIPIHVFGTETHMTAIVGMALGHRPIPNQPPTAAH
  H.sapiens   DGKILIIGGSIANFTNVAATFKGIVRAIRDYQGCPLKEHEVTIFVRRGGPNYQEGLRVMGEVGKTTGIPIHVFGTETHMTAIVGMALGHRPIPNQPPTAAH
D.melanogaster DGKVLIIGGGIANFTNVAATFQGIITALREFQPKLVEHNVSIFVRRGAGPNYQEGLRKMRDFGSTLGIPLHVFGPETHMTAICGMALGKRPIPQTASVEFS
  C.elegans   DGKVLIIGGSIANFTNVAKTFGGIVRAFETFIDKLKEHNVSIYVRRGGPNYQEGLRRVKDAATKLEIPIYVFGPETHMTAIVGAALGLKPMPTVPTAPQT
              501                                                                                                      600
    MaACL1    NNGSASSGN------LLQDQLLGTNSNLNTPVPTAPVSRAGTPPASERMTYFTDADAKKVG---HDSNVPFTAQTRSFIYGMQPRAVQGMLDFDFICKREV
    MaACL2    PSAHLSSGN------LLQDQLLGNNTPLNAGSRAS-----SPPPLEDRMTYFQDQNAESSESSHDENTPFTAHTRSFIYGMQPRAVQGMLDFDFICKREV
  U.maydis    QNTLPSGAA------TPAHGAANGTKAENKAIGTVDHNTGERVQPQDQIVHFGACGSTTGER---PAYRPFDANTRSLVFGLQPRAIQGMLDFDFSCGRKT
M.musculus    TANFLLN----------ASGSTSTPAPSRTASFSESRADEVAPAKKAKPAMPQ-----------GKSATLFSRHTKAIVWGMQTRAVQGMLDFDYVCSRDE
  H.sapiens   TANFLLN----------ASGSTSTPAPSRTASFSESRADEVAPAKKAKPAMPQDSVPSPRSLQGKSTTLFSRHTKAIVWGMQTRAVQGMLDFDYVCSRDE
D.melanogaster TANFLLPGGQQAQADLKAASDASEALGSGSALSPTAAKPIKLPPISADEADSAGISGAQRNGSSLNRKFFSNTTKAIVWGMQQRAVQSMLDFDFICRRDE
  C.elegans   TQQFLLS---------PERNTAGTE--RPPASPAPNTSTIEHPLAKRHPLHQS--------------LFENDTKAIIWGQHKAIQGMLDFDFVCRRHS
              601                                                                                                      700
    MaACL1    PSVAAMIYPFGGAHVQKFYWGTKETLPVVTTLEEATAKFPEVDTVVNFASCRSVYQSTVDILSHSDQIKTISIIAEGVPERRARQILWEAKAKNVLVIG
    MaACL2    PSVAAMYYPFGGAHVQKFYWGTKETLPVFTSLDEAVAKYPEVDTVVFASCRSVYDSTREIFKHSKQIRTISIIIAEGVPERRARQILWEAKERNVLVIG
  U.maydis    PSVAAMIYPFCGGHHIQKEYWGTKETLPVYTSIKEAVAKHPDADVVVNFASSRSVYSSTLEVLDCP-QIRALALIAEGVPERHAREILHRAEKAGVLIIG
M.musculus    PSVAAMVYPFTGDHKQKEYWGHKEILIPVFKNMADAMKKHPEVDVLINFASLRSAYDSTMETMNYA-QIRTIAIIAEGIPEALTRKLIKKADQKGVTIIG
  H.sapiens   PSVAAMVYPFTGDHKQKEYWGHKEILIPVFKNMADAMKKHPEVDVLINFASLRSAYDSTMETMNYA-QIRTIAIIAEGIPEALTRKLIKKADQKGVTIIG
D.melanogaster PSVAAMVYPFTGDHKQKEYWGHKEILIPVIKKMSDAIHHKKEVDTMASMRSAYESTLEVLEFP-QIRTVAIIAEGVPLEVFP-QIRTVAIIAEGVPIEPNMTRKLIEADKKGVAIIG
  C.elegans   PSVVASTYPFTGDNKQKYYFGQKEILLPAYKSMAKAFASHPDATVMVTFASMRSVFETVLEALQFT-QIKVIAIIAEGVPENQTRKLLKIAEDKGVTLIG
```

Figure5-2

```
              701                                                                                                  800
    MaACL1    PATVGGIKPGCFKIGNTGGMMDNIVSSKLYRAGSVAYVSKSGGMSNELNNIISRTTDGVYEGVAIGGDRYPGSTFIDHLLRYERDPNCKMLVLLGEVGGV
    MaACL2    PATVGGIKPGCFKIGNTGGMMDNIVSSKLYRAGSVAYVSKSGGMSNELNNIISRTTDGVYEGVAIGGDRYPGSTFIDHLLRYEKDPGCKMLVLLGEVGGV
    U.maydis  PATVGGIKPGCFRIGNSGGMMDNILASKLYRPGSVGYVSKSGGMSNELNNILSITTNGTYEGIAIGGDRYPGTTFIDHLLRYEQDPECKMLVLLGEVGGI
    M.musculus PATVGGIKPGCFKIGNTGGMLDNILASKLYRPGSVAYVSRSGGMSNELNNIISRTTDGVYEGVAIGGDRYPGSTFMDHVLRYQDTPGVKMIVVLGEIGGT
    H.sapiens  PATVGGIKPGCFKIGNTGGMLDNILASKLYRPGSVAYVSRSGGMSNELNNIISRTTDGVYEGVAIGGDRYPGSTFMDHVLRYQDTPGVKMIVVLGEIGGT
    D.melanogaster PATVGGVKPGCFKIGNTGGMLDNILHSKLYRPGSVAYVSRSGGMSNELNNIISKATDGVIEGIAIGGDRYPGSTFMDHILRYQADPETKLIVLLGEVGGT
    C.elegans  PATVGGIKPGCFKIGNTGGMMDNILASKLYRPGSVAYVSRSGGMSNELNNIISQNTNGVYEGIAIGGDRYPGSTYTDHVMRYQHDDRVKMIVLLGEVGGI
              801                                                                                                  900
    MaACL1    EEYKVCEAIKNGTIRKPVIAWCIGTCAKMFATEVQFGHAGALAQSDLETADAKNKALRAAGVVVPETFEKLPLVLSQTFQTLVKNGTIQLKPEPETPKIP
    MaACL2    EEYKVCEAIKNGAIRKPVIAWCIGTCAKMFATEVQFGHAGALAQSDLETADAKNKALRAAGVIVPETFEMLPLVLSQTYQALVKKGVVIVRSEPETPKIP
    U.maydis  EEYRVIEAVKKGTIKKPIIAWAIGTCAKMFTTEVQFGHAGSMANSDMETASAKNAANKAAGFIVPDTFEDLPAVIREVYNKLVASGTIQPKPERPAPAIP
    M.musculus EEYKICRGIKEGRLTKPVVCMCIGTCATMFSSEVQFGHAGACANQASETAVAKNQALKEAGVFVPRSFDELGEIIQSVYEDLVAKGAIVPAQEVPPPTVP
    H.sapiens  EEYKICRGIKEGRLTKPIVCMCIGTCATMFSSEVQFGHAGACANQASETAVAKNQALKEAGVFVPRSFDELGEIIQSVYEDLVANGVIVPAQEVPPPTVP
    D.melanogaster EEYDVCAALKDGRITKPLVAWCIGTCASMFTSEVQFGHAGSCANSDRETATAKNKGLRDAGAYVPDSFDTLGELIHHVYGELVKTGRVVPKEEVPPPTVP
    C.elegans  EEYRIVELLKEKKITKPLIAWCIGTCADHITSEVQFGHAGASANGQGETAACKNTALRTAGALVPDSFDDLGNKIRQTYEELLRLEIIVPQPEVPPPAVP
              901                                                                                                 1000
    MaACL1    IDYSWAQELGLVRKPASFVSTICDDRGQELLYAGMRISDVFKEDIGIGGVLSLLWFKRRLPDYACKFIEMVLMLTADHGPAVSGAHNTIVTARAGKDLVS
    MaACL2    IDYSWAQELGLVRKPASFVSTICDDRGQELLYAGMRISDVFKEDIGIGGVLSLLWFKRRLPDYACKFIEMVLMLTADHGPAVSGAHNTIVTARAGKDLVS
    U.maydis  VDYKWAQELGMVRKPAAFISTISDERGSELNYSGVKISEVFEESGNGIGGVISLLWFKRRLPDYCTKFIEMALMLTADHGPAVSGAMNTIITSRAGKDLIS
    M.musculus MDYSWARELGLIRKPASFMTSICDERGQELIYAGMPITEVFKEEMGIGGVLLLWFQRRLPKYSCQFIEMCLMVTADHGPAVSGAHNTIICARAGKDLVS
    H.sapiens  MDYSWARELGLIRKPASFMTSICDERGQELIYAGMPITEVFKEENGIGGVLLLWFQRRLPKYSCQFIEMCLMVTADHGPAVSGAHNTIICARAGKDLVS
    D.melanogaster MDYSWARELGLIRKPASFMTSICDERGQELIYAGMPISEVLSKDVGIGGVISLLWFQRCLPSYVCKFFEMCLMVTADHGPAVSGAHNTIVCARAGKDLVS
    C.elegans  MDYAWARELGLIRKPASFMTSICDERGEELNYAGVPITKVLESDMGIGGVLGLLWFQKRLPPHANKFIECLMLTADHGPAVSGAHNTIVCARAGKDLIS
              1001                                                                                                1100
    MaACL1    SLCAGLLTIGDRFGGALDGAAEQFSSAYDKSLTPREFVSVMRKQNKLILGIGHKIKSRTNPDLRVEIIKEYAKKH----FPSTPVLDYALQVENITTSKKD
    MaACL2    SLCAGLLTIGDRFGGALDGAAEQFSSAYDKSLSPREFVSSMRKQNKLILGIGHKIKSRTNPDLRVEIIKNYAKAH----FPATPVLDYALAVETITTSKKD
    U.maydis  SLVGLLTIGDRFGGALDDAATEFSSAYDRGMTAREFVDSMRKANKLIPGIGHKIKSVSNPDYRVQVVKEFVLTN----FPSHKMLDYALAVEKVTTAKKD
    M.musculus SLTSGLLTIGDRFGGALDAAAKMFSKAFDSGIIPMEFVNKMKKEGKLIMGIGHRVKSINNPDMRVQILKDFVKQH----FPATPLLDYALEVEKITTSKKP
    H.sapiens  SLTSGLLTIGDRFGGALDAAAKMFSKAFDSGIIPMEFVNKMKKEGKLEMGIGHRVKSINNPDMRVQILKDYVRQH----FPATPLLDYALEVEKITTSKKP
    D.melanogaster SVVSGLLTIGDRFGGALDGSARQFSEAYDTNLHPMEFVNKMKREGKLILGIGHRVKSINNPDVRVKIIKEFVLEN----FPACPLLKYALEVEKITTNKKP
    C.elegans  SLTSGLLTIGDRFGGALDGAARQFSEAFDQGWSPNQFVGEMRKRGTHIMGIGHRVKSINNPDKRVEILKRFALNKKEFAQETPLLDYALEVEKITTAKKP
              1101                                                                                        1196
    MaACL1    NLILNVDGAIGILFVDLLRNSGAFTREEAEEYIKIGTLNGLFVLGRSIGFIGHYLDQKRLKQGLYRHPWDDISYLTPGNELGRTVASLDSINKKA-
    MaACL2    NLILNVDGAIGILFVDLLRNSGAFTREEAEEYIKIGTLNGLFVLGRTIGFIGHFLDQKRLKQGLYRHPWDDISYLTPGNELGRTVASLDSINKKAA
    U.maydis  TLILNVDGCLAVCFVDLLRDSGAFTIEEARDYLSYGFLNGIFTLGRSIGFIGHHIDQKRLKAGLYRHPADDFHIEMATPARVMGTLKK--------
    M.musculus NLILNVDGFIGVAFVDNLRNCGSFTREEADEYVDIGALNGIFVLGRSMGFIGHYLDQKRLKQGLYRHPWDDISYVLPEHMSM--------------
    H.sapiens  NLILNVDGLIGVAFVDNLRNCGSFTREEADEYIDIGALNGIFVLGRSMGFIGHYLDQKRLKQGLYRHPWDDISYVLPEHMSM--------------
    D.melanogaster NLILNVDGVIATAFVDNLRNSGSFTSEEAQEYINVGAINSLFVLGRSIGFIGHYMDQKRLKQGLYRHPWDDISYVIPEQYN---------------
    C.elegans  NLILNVDGAIAIIFVDILRNSGMFTTAEAQEVIEIGALNGMFVLGRSIGFIGHYLDQSRLKQGLYRHPWDDISYIMPERNL---------------
```

ATP:CITRATE LYASE GENES

TECHNICAL FIELD

The present invention relates to novel genes for ATP:citrate lyase.

BACKGROUND ART

Fatty acids are important components of lipids such as phospholipids and triacylglycerols. Fatty acids containing two or more unsaturated bonds are collectively referred to as polyunsaturated fatty acids (PUFA) and are known to include arachidonic acid, dihomo-γ-linolenic acid, eicosapentaenoic acid and docosahexaenoic acid. Various physiological activities have been reported for these fatty acids (Non-patent Document 1). These polyunsaturated fatty acids are expected to have applications in various fields, but some of them cannot be synthesized in the animal body. Thus, microbial techniques have been developed for obtaining polyunsaturated fatty acids by culturing various microorganisms. Other attempts have also been made to produce polyunsaturated fatty acids in plants. In these cases, polyunsaturated fatty acids are known to be accumulated, for example, as components of lipids such as triacylglycerols within microorganism cells or plant seeds.

Such novel fatty acid synthesis in animals, plants and microorganisms is mediated by fatty acid synthetase, starting from acetyl-CoA and malonyl-CoA that is generated from acetyl-CoA by the action of acetyl-CoA carboxylase (ACC). These reactions are known to occur in the cytoplasm for animals or microorganisms and in chloroplasts for plants.

Acetyl-CoA, which serves as a source material of these fatty acids and cholesterol newly synthesized in the cytoplasm, is supplied from citrate by the action of ATP:citrate lyase (E.C. 2.3.3.8; hereinafter also referred to as ACL).

ACL is an enzyme catalyzing the following reaction.

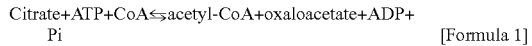
[Formula 1]

This enzyme is widely distributed in eukaryotic organisms including animals, plants and fungi, and its intracellular localization is found in the cytoplasm (Non-patent Document 2). ACL genes have been reported so far in several organisms. For example, as animal ACL genes, those derived from *Homo sapiens* and *Rattus norvegicus* have been cloned (Non-patent Document 3, Non-patent Document 4). As plant ACL genes, ACLA-1, -2, -3 and ACLB-1, -2 derived from *Arabidopsis* (ecotype Columbia) have been cloned (Non-patent Document 5). In the case of filamentous fungi, ACLA and ACLB genes derived from *Sordaria macrospora* have been cloned (Non-patent Document 6).

With respect to *Mortierella alpina* (hereinafter also referred to as "*M. alpina*"), which is a lipid-producing fungus, the cytoplasmic fraction has been reported to have ATP:citrate lyase activity (Non-patent Document 7).

Until now, these known ACL genes have been used in an attempt to increase the content of total fatty acids in hosts, for example, by highly expressing a *Sordaria macrospora*-derived ACL gene together with fatty acid synthetase (FAS) in yeast cells (Patent Document 1) or by highly expressing a *Rattus norvegicus*-derived ACL gene in plants (Non-patent Document 8).

Patent Document 1: US Patent Publication No. 2006/0051847
Non-patent Document 1: Lipids, 39, pp. 1147 (2004)
Non-patent Document 2: Adv Appl Microbiol., 51, pp. 1-51 (2002)
Non-patent Document 3: Eur J Bio Chem., 204, pp. 491-499 (1992)
Non-patent Document 4: J Bio chem., 265, pp. 1430-1435 (1990)
Non-patent Document 5: Plant Physiology., 130, pp. 740-756 (2002)
Non-patent Document 6: Curr. genet., 37, pp. 189-93 (2000)
Non-patent Document 7: Microbiology., 146, pp. 2325-2331 (2000)
Non-patent Document 8: Plant Physiology., 122, pp. 1231-1238 (2000)

DISCLOSURE OF THE INVENTION

Problems to be Solved by the Invention

However, the ACL genes previously reported are not sufficient, for example, because these genes cannot be confirmed to have an effect by themselves when introduced into and expressed in host cells or because there is a limit on the range of hosts available for use in the expression of such genes. For this reason, there is a need to identify a novel gene, which differs from those reported to date and allows an increase in the content of total fatty acids or lipids in hosts.

Means for Solving the Problems

The object of the present invention is to provide a protein or nucleic acid that allows an increase in the content of fatty acids or lipids by being expressed in or introduced into host cells.

To achieve the above object, the inventors of the present invention have made extensive and intensive efforts. First, EST analysis was performed on a lipid-producing fungus, *Mortierella alpina*, to extract sequences sharing high identity with known ACL genes. To obtain the entire open reading frame (ORF) encoding ACL, genes were further cloned by cDNA library screening or PCR. These genes were expressed in *Saccharomyces cerevisiae* having no ACL gene, followed by ACL activity measurement to confirm the ACL activity of the above genes.

Moreover, as a result of attempting to introduce and highly express these genes in host cells (e.g., a lipid-producing fungus, *Mortierella alpina*) to thereby achieve high level production of total fatty acids, the inventors succeeded in cloning a novel gene related to ACL, which allows an increase in the content of total fatty acids as compared to hosts expressing a conventional level of ACL. This led to the completion of the present invention. Namely, the present invention is as follows.

(1) A nucleic acid comprising a nucleotide sequence shown in any one of (a) to (e) below:
(a) a nucleotide sequence which encodes a protein consisting of an amino acid sequence with deletion, substitution or addition of one or more amino acids in the amino acid sequence shown in SEQ ID NO: 11 or SEQ ID NO: 12 and having ATP:citrate lyase activity;
(b) a nucleotide sequence which is hybridizable under stringent conditions with a nucleic acid consisting of a nucleotide sequence complementary to a nucleotide sequence consisting of SEQ ID NO: 9 or SEQ ID NO: 10 and which encodes a protein having ATP:citrate lyase activity;
(c) a nucleotide sequence which consists of a nucleotide sequence sharing an identity of 70% or more with a nucleotide sequence consisting of SEQ ID NO: 9 or SEQ ID NO: 10 and which encodes a protein having ATP:citrate lyase activity;

(d) a nucleotide sequence which encodes an amino acid sequence sharing an identity of 70% or more with an amino acid sequence consisting of SEQ ID NO: 11 or SEQ ID NO: 12 and which encodes a protein having ATP:citrate lyase activity; or (e) a nucleotide sequence which is hybridizable under stringent conditions with a nucleic acid consisting of a nucleotide sequence complementary to a nucleotide sequence encoding a protein consisting of the amino acid sequence shown in SEQ ID NO: 11 or 12 and which encodes a protein having ATP:citrate lyase activity.

(2) The nucleic acid according to (1) above, which comprises a nucleotide sequence shown in any one of (a) to (c) below:

(a) a nucleotide sequence which encodes a protein consisting of an amino acid sequence with deletion, substitution or addition of 1 to 10 amino acids in the amino acid sequence shown in SEQ ID NO: 11 or SEQ ID NO: 12 and having ATP:citrate lyase activity;

(b) a nucleotide sequence which is hybridizable under conditions of 2×SSC at 50° C. with a nucleic acid consisting of a nucleotide sequence complementary to a nucleotide sequence consisting of SEQ ID NO: 9 or SEQ ID NO: 10 and which encodes a protein having ATP:citrate lyase activity; or (c) a nucleotide sequence which encodes an amino acid sequence sharing an identity of 90% or more with an amino acid sequence consisting of SEQ ID NO: 11 or SEQ ID NO: 12 and which encodes a protein having ATP:citrate lyase activity.

(3) A nucleic acid comprising a nucleotide sequence shown in any one of (a) to (c) below or a fragment thereof:

(a) the nucleotide sequence shown in SEQ ID NO: 9 or SEQ ID NO: 10;

(b) a nucleotide sequence encoding a protein consisting of the amino acid sequence shown in SEQ ID NO: 11 or SEQ ID NO: 12; or (c) the nucleotide sequence shown in SEQ ID NO: 5 or SEQ ID NO: 6.

(4) A protein shown in (a) or (b) below:

(a) a protein which consists of an amino acid sequence with deletion, substitution or addition of one or more amino acids in SEQ ID NO: 11 or SEQ ID NO: 12 and which has ATP:citrate lyase activity; or (b) a protein which consists of an amino acid sequence sharing an identity of 70% or more with an amino acid sequence consisting of SEQ ID NO: 11 or SEQ ID NO: 12 and which has ATP:citrate lyase activity.

(5) A protein consisting of the amino acid sequence shown in SEQ ID NO: 11 or SEQ ID NO: 12.

(6) A recombinant vector comprising the nucleic acid according to any one of (1) to (3) above.

(7) A transformant carrying the nucleic acid according to any one of (1) to (3) above.

(8) A transformant transformed with the recombinant vector according to (6) above.

(9) The transformant according to (8) above, whose ability to produce fatty acids is improved by introduction of the vector according to (6) above.

(10) The transformant according to any one of (7) to (9) above, wherein the transformant is a lipid-producing fungus.

(11) The transformant according to (10) above, wherein the lipid-producing fungus is *Mortierella alpina*.

(12) A method for preparing a fatty acid or lipid, which comprises collecting a fatty acid or lipid from a cultured product obtained by culturing the transformant according to any one of (7) to (11) above.

(13) A fatty acid or lipid obtainable by using the method according to (12) above.

(14) A food product comprising the fatty acid or lipid according to (13) above.

Advantages of the Invention

The ACL of the present invention allows an improvement in the ability to produce fatty acids and/or lipids, and hence is preferred as a means for improving the productivity of polyunsaturated fatty acids in microorganisms and plants. As a result, the ACL of the present invention enables the provision of useful lipids at a lower cost than in conventional cases, and is useful as being applicable to foods, cosmetics, pharmaceuticals, soaps, etc.

BRIEF DESCRIPTION OF THE DRAWINGS

FIG. 1 shows the cDNA sequence of MaACL1 according to the present invention, along with its deduced amino acid sequence. FIG. 1-1 discloses nucleotides 1-1900 of SEQ ID NO: 5 and amino acids 1-575 of SEQ ID NO: 11.

FIG. 1 shows the cDNA sequence of MaACL1 according to the present invention, along with its deduced amino acid sequence. FIG. 1-2 discloses nucleotides 1901-3840 of SEQ ID NO: 5 and amino acids 576-1179 of SEQ ID NO: 11.

FIG. 2 shows the cDNA sequence of MaACL2 according to the present invention, along with its deduced amino acid sequence. FIG. 2-1 discloses nucleotides 1-1900 of SEQ ID NO: 6 and amino acids 1-627 of SEQ ID NO: 12.

FIG. 2 shows the cDNA sequence of MaACL2 according to the present invention, along with its deduced amino acid sequence. FIG. 2-2 discloses nucleotides 1901-3686 of SEQ ID NO: 6 and amino acids 628-1174 of SEQ ID NO: 12.

FIG. 3 shows a comparison of DNA sequences between CDS regions of MaACL1 and MaACL2. FIG. 3-1 discloses nucleotides 1-1887 of SEQ ID NO: 7 (ACL1) and nucleotides 1-1869 of SEQ ID NO: 8 (ACL2).

FIG. 3 shows a comparison of DNA sequences between CDS regions of MaACL1 and MaACL2. FIG. 3-2 discloses nucleotides 1888-3540 of SEQ ID NO: 7 (ACL1) and nucleotides 1870-3525 of SEQ ID NO: 8 (ACL2), respectively, in order of appearance.

FIG. 4 shows a comparison of deduced amino acid sequences between MaACL1 and MaACL2. FIG. 4 discloses SEQ ID NOS 11 and 12, respectively, in order of appearance.

FIG. 5 shows the deduced amino acid sequences of MaACL1p and MaACL2p in comparison with known amino acid sequences. FIG. 5-1 discloses amino acids 1-687 of SEQ ID NO:11 (MaACL1), 1-681 of SEQ ID NO: 12 (MaACL2), 1-667 of SEQ ID NO: 36 (*U. maydis*), 1-612 of SEQ ID NO: 37 (*M. musculus*), 1-622 of SEQ ID NO: 38 (*H. sapiens*), 1-634 of SEQ ID NO: 39 (*D. melanogaster*), and 1-618 of SEQ ID NO: 40 (*C. elegans*).

FIG. 5 shows the deduced amino acid sequences of MaACL1p and MaACL2p in comparison with known amino acid sequences. FIG. 5-2 discloses amino acids 688-1179 of SEQ ID NO: 11 (MaACL1), 682-1174 of SEQ ID NO: 12 (MaACL2), 668-1152 of SEQ ID NO: 36 (*U. maydis*), 613-1091 of SEQ ID NO: 37 (*M. musculus*), 623-1101 of SEQ ID NO: 38 (*H. sapiens*), 635-1112 of SEQ ID NO: 39 (*D. melanogaster*), and 619-1099 of SEQ ID NO: 40 (*C. elegans*).

BEST MODE FOR CARRYING OUT THE INVENTION

Figure 6:
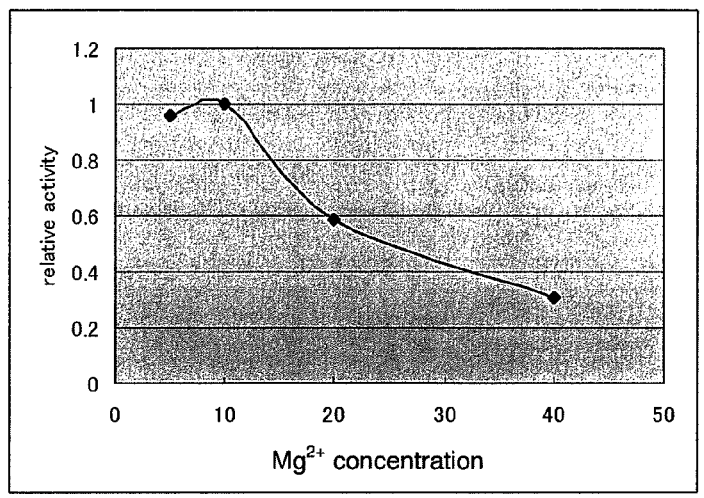
FIG. 6 is a graph showing the dependence of MaACL1 on $Mg^{2+}$ concentration.

The present invention relates to novel genes for ATP:citrate lyase derived from the genus *Mortierella*, characterized by generating acetyl-CoA, oxaloacetate, ADP and Pi from ATP, citrate and CoA.

In the case of eukaryotic organisms having intracellular compartments separated by organelles, acetyl-CoA according to the present invention is generated primarily in mitochondria by the action of pyruvate dehydrogenase or by β-oxidation. However, acetyl-CoA cannot permeate through the mitochondrial membrane, and is supplied as citrate into the cytoplasm. Acetyl-CoA supplied to the cytoplasm from this citrate by the action of ACL serves as a source material for fatty acids or cholesterol newly synthesized in the cytoplasm.

Nucleic Acids of the Present Invention Encoding ATP: Citrate Lyase

ATP:citrate lyase (ACL) in the present invention encompasses MaACL1 and MaACL2. The correspondence between cDNA, CDS, ORF and amino acid sequence is summarized in Table 1 below for each of nucleic acids encoding MaACL1 and MaACL2.

genomic DNAs, chemically synthesized DNAs, PCR-amplified DNAs, as well as combinations thereof and DNA/RNA hybrids.

Preferred embodiments for the nucleic acids of the present invention include (a) the nucleotide sequence shown in SEQ ID NO: 9 or SEQ ID NO: 10, (b) a nucleotide sequence encoding a protein consisting of the amino acid sequence shown in SEQ ID NO: 11 or 12, and (c) the nucleotide sequence shown in SEQ ID NO: 5 or 6.

The above nucleotide sequence shown in SEQ ID NO: 9 or SEQ ID NO: 10, nucleotide sequence encoding a protein consisting of the amino acid sequence shown in SEQ ID NO: 11 or 12, and nucleotide sequence shown in SEQ ID NO: 5 or 6 are as shown in Table 1.

To obtain these nucleotide sequences, nucleotide sequence data of ESTs or genomic DNAs from organisms having ATP: citrate lyase activity (hereinafter also referred to as ACL activity) may be used to search a nucleotide sequence encoding a protein sharing high identity with known proteins having ACL activity. Preferred organisms having ACL activity are lipid-producing fungi including, but not limited to, *M. alpina*.

For EST analysis, a cDNA library is first prepared. As to techniques for cDNA library preparation, reference may be made to "Molecular Cloning, A Laboratory Manual 3rd ed." (Cold Spring Harbor Press (2001)). Alternatively, a commercially available cDNA library preparation kit may be used. Techniques for cDNA library preparation suitable for the present invention are as follows, by way of example. Namely,

TABLE 1

|  | MaACL1 | | MaACL2 | |
| --- | --- | --- | --- | --- |
|  | SEQ ID NO | Corresponding region in SEQ ID NO: 5 | SEQ ID NO | Corresponding region in SEQ ID NO: 6 |
| cDNA | SEQ ID NO: 5 | ***** | SEQ ID NO: 6 | ***** |
| CDS | SEQ ID NO: 7 | Positions 178-3717 | SEQ ID NO: 8 | Positions 21-3545 |
| ORF | SEQ ID NO: 9 | Positions 178-3714 | SEQ ID NO: 10 | Positions 21-3542 |
| Amino acid sequence | SEQ ID NO: 11 | ***** | SEQ ID NO: 12 | ***** |

Namely, sequences related to MaACL1 of the present invention include SEQ ID NO: 11 (amino acid sequence of MaACL1), SEQ ID NO: 9 (sequence representing the ORF region of MaACL1), SEQ ID NO: 7 (sequence representing the CDS region of MaACL1) and SEQ ID NO: 5 (nucleotide sequence of cDNA for MaACL1). Among them, SEQ ID NO: 7 corresponds to nucleotides 178-3717 of SEQ ID NO: 5, while SEQ ID NO: 9 corresponds to nucleotides 178-3714 of SEQ ID NO: 5 or nucleotides 1-3537 of SEQ ID NO: 7.

Likewise, sequences related to MaACL2 include SEQ ID NO: 12 (amino acid sequence of MaACL2), SEQ ID NO: 10 (sequence representing the ORF region of MaACL2), SEQ ID NO: 8 (sequence representing the CDS region of MaACL2) and SEQ ID NO: 6 (nucleotide sequence of cDNA for MaACL2). Among them, SEQ ID NO: 8 corresponds to nucleotides 21-3545 of SEQ ID NO: 6, while SEQ ID NO: 10 corresponds to nucleotides 21-3542 of SEQ ID NO: 6 or nucleotides 1-3522 of SEQ ID NO: 8.

The nucleic acids of the present invention encompass single-stranded and double-stranded DNAs as well as complementary RNAs thereof, which may be either naturally occurring or artificially prepared. DNAs include, but are not limited to, genomic DNAs, cDNAs corresponding to the an appropriate strain of *M. alpina*, a lipid-producing fungus, is inoculated into an appropriate medium and pre-cultured for an appropriate period. Culture conditions suitable for this pre-culture include, for example, medium composition of 1.8% glucose, 1% yeast extract and pH 6.0, a culture period of 3 days, and a culture temperature of 28° C. The pre-cultured product is then subjected to main culture under appropriate conditions. Medium composition suitable for main culture may be, for example, 1.8% glucose, 1% soybean powder, 0.1% olive oil, 0.01% Adekanol, 0.3% $KH_2PO_4$, 0.1% $Na_2SO_4$, 0.05% $CaCl_2.2H_2O$, 0.05% $MgCl_2.6H_2O$ and pH 6.0. Culture conditions suitable for main culture may be, for example, aerobic spinner culture at 300 rpm, 1 vvm, 26° C. for 8 days. An appropriate amount of glucose may be added during culture. The cultured product is sampled at appropriate time points during main culture, from which the cells are then collected to prepare total RNA. For preparation of total RNA, it is possible to use any known technique, such as guanidine hydrochloride/CsCl method. The resulting total RNA may be treated with a commercially available kit to purify poly(A)+ RNA. Further, a cDNA library may be prepared with a commercially available kit. Then, any clone from the cDNA library thus prepared is determined for its nucleotide sequence by using primers which are designed on a vector to allow determination of the nucleotide sequence of an insert. As a result, ESTs can be obtained. For example, when a ZAP-cDNA GigapackIII Gold Cloning Kit (STRATAGENE) is used for cDNA library preparation, directional cloning can be performed.

The nucleotide sequence identity between CDSs of MaACL1 and MaACL2 of the present invention is 79.1%. Likewise, the amino acid sequence identity between MaACL1 and MaACL2 is 87.1%. It should be noted that when analyzed by BLASTP, the amino acid sequences of MaACL1 and MaACL2 of the present invention share an identity of 61.6% and 61.9%, respectively, with a *Ustilago maydis* 521-derived putative protein (FIG. 5) (UM01005.1, GB accession No. EAK82015, giA6096782) having the lowest E-value.

The present invention also encompasses nucleic acids functionally equivalent to a nucleic acid comprising the above nucleotide sequence shown in SEQ ID NO: 9 or 10 (hereinafter also referred to as "the nucleotide sequence of the present invention") or nucleotide sequence encoding a protein consisting of the amino acid sequence shown in SEQ ID NO: 11 or 12 (hereinafter also referred to as "the amino acid sequence of the present invention"). The phrase "functionally equivalent" is intended to mean that a protein encoded by the nucleotide sequence of the present invention or a protein consisting of the amino acid sequence of the present invention has ACL activity, or alternatively, it is intended to mean having not only ACL activity, but also enzyme activity properties equal to those of a protein encoded by the nucleotide sequence of the present invention or a protein consisting of the amino acid sequence of the present invention. Enzyme activity properties include all properties, such as changes in activity in response to changes in temperature, pH, salt concentration or substrate concentration under enzyme reaction conditions, Km values, substrate specificity, etc.

The ACL of the present invention catalyzes a reaction in which acetyl-CoA, oxaloacetate, ADP and Pi are generated from ATP, citrate and CoA. Its "ACL activity" can be measured in a known manner. For example, reference may be made to the following document: Plant Physiol., 2002, 130, 740-56.

"ACL activity" in the present invention may be measured as follows, by way of example. A cytoplasmic fraction is prepared from yeast cells (having no endogenous ACL gene) which are transformed to express MaACL1 or MaACL2 of the present invention, as described in, e.g., Plant Physiol., 2002, 130, 740-56. To a reaction solution containing 20 mM $MgCl_2$, 1 mM DTT, 10 mM ATP, 10 mM citrate, 0.2 mM CoA, 6 units of malate dehydrogenase and 0.1 mM NADH in 10 mM Tris-HCl (pH 8.4), the above cytoplasmic fraction is added and reacted at 28° C. for an appropriate period, and then measured for changes in $A_{340}$ (decrease in NADH levels) with an absorptiometer to thereby quantify "ACL activity."

The phrase "having ACL activity" as used herein is preferably intended to mean having an activity of 1.0 nmol·$min^{-1}$·$mg^{-1}$ or more, although it is not limited in any way as long as a decrease in NADH levels can be detected in the above assay.

Moreover, the ACL activity of MaACL1 of the present invention (SEQ ID NO: 11) was confirmed to depend on $Mg^{2+}$ concentration. More specifically, the activity reached a peak at a $Mg^{2+}$ concentration of 5 to 10 mM, and then decreased with increases in $Mg^{2+}$ concentration (FIG. 6). MaACL1 was also found to show the maximum activity at an ATP:citrate:$Mg^{2+}$ ratio of about 1:1:1.

Such nucleic acids that are functionally equivalent to the nucleic acids of the present invention include a nucleic acid comprising a nucleotide sequence shown in any one of (a) to (e) below. It should be noted that when used to describe the nucleotide sequences listed below, the phrase "the above activity of the present invention" is intended to mean "having ACL activity and/or enzyme activity properties equal to those of a protein encoded by the nucleotide sequence of the present invention or a protein consisting of the amino acid sequence of the present invention" defined above.

(a) A nucleotide sequence which encodes a protein consisting of an amino acid sequence with deletion, substitution or addition of one or more amino acids in the amino acid sequence shown in SEQ ID NO: 11 or SEQ ID NO: 12 and having the activity of the present invention Nucleotide sequences contained in the nucleic acids of the present invention include a nucleotide sequence which encodes a protein consisting of an amino acid sequence with deletion, substitution or addition of one or more amino acids in the amino acid sequence shown in SEQ ID NO: 11 or SEQ ID NO: 12 and having the above activity of the present invention.

More specifically, it is a nucleotide sequence which encodes a protein consisting of:

(i) an amino acid sequence with deletion of one or more (preferably one or several (e.g., 1-350, 1-300, 1-250, 1-200, 1-150, 1-100, 1-50, 1-30, 1-25, 1-20, 1-15, 1-10, more preferably 1-5)) amino acids in the amino acid sequence shown in SEQ ID NO: 11 or 12;

(ii) an amino acid sequence with substitution of other amino acids for one or more (preferably one or several (e.g., 1-350, 1-300, 1-250, 1-200, 1-150, 1-100, 1-50, 1-30, 1-25, 1-20, 1-15, 1-10, more preferably 1-5)) amino acids in the amino acid sequence shown in SEQ ID NO: 11 or 12;

(iii) an amino acid sequence with addition of other one or more (preferably one or several (e.g., 1-350, 1-300, 1-250, 1-200, 1-150, 1-100, 1-50, 1-30, 1-25, 1-20, 1-15, 1-10, more preferably 1-5)) amino acids in the amino acid sequence shown in SEQ ID NO: 11 or 12; or (iv) an amino acid sequence with any combination of (i) to (iii) above, and having the above activity of the present invention.

Among the above modifications, substitution is preferably conservative, which means the replacement of a certain amino acid residue by another residue having similar physical and chemical characteristics. It may be any substitution as long as it does not substantially alter the structural characteristics of the original sequence. For example, any substitution is possible as long as the substituted amino acids do not disrupt a helix present in the original sequence or do not disrupt any other type of secondary structure characterizing the original sequence.

Conservative substitution is generally introduced by synthesis in biological systems or chemical peptide synthesis, preferably by chemical peptide synthesis. In this case, substituents may include unnatural amino acid residues, as well as peptidomimetics, and reversed or inverted forms of amino acid sequences in which unsubstituted regions are reversed or inverted.

Amino acid residues are classified and listed below in groups of mutually substitutable members, but are not limited to the following:

Group A: leucine, isoleucine, norleucine, valine, norvaline, alanine, 2-aminobutanoic acid, methionine, O-methylserine, t-butylglycine, t-butylalanine and cyclohexylalanine;

Group B: aspartic acid, glutamic acid, isoaspartic acid, isoglutamic acid, 2-aminoadipic acid and 2-aminosuberic acid;

Group C: asparagine and glutamine;

Group D: lysine, arginine, ornithine, 2,4-diaminobutanoic acid and 2,3-diaminopropionic acid;
Group E: proline, 3-hydroxyproline and 4-hydroxyproline;
Group F: serine, threonine and homoserine; and
Group G: phenylalanine and tyrosine.

Non-conservative substitution may involve the exchange of a member of one of the above classes for a member from another class. In this case, for the purpose of maintaining biological functions of the proteins of the present invention, it is preferable to consider the hydropathic index of amino acids (hydropathic amino acid index) (Kyte et al., J. Mol. Biol., 157:105-131 (1982)).

In the case of non-conservative substitution, amino acid substitutions may also be accomplished on the basis of hydrophilicity.

In the specification and drawings of the present application, nucleotides, amino acids and abbreviations thereof are those according to the IUPAC-IUB Commission on Biochemical Nomenclature or those conventionally used in the art, for example, as described in Immunology—A Synthesis (second edition, edited by E. S. Golub and D. R. Gren, Sinauer Associates, Sunderland, Mass. (1991)). Moreover, amino acids which may have optical isomers are intended to represent their L-isomer, unless otherwise specified.

Stereoisomers (e.g., D-amino acids) of the above amino acids, unnatural amino acids such as α,α-disubstituted amino acids, N-alkylamino acids, lactic acid, and other unconventional amino acids may also be members constituting the proteins of the present invention.

It should be noted that in the protein notation used herein, the lefthand direction is the amino terminal direction and the righthand direction is the carboxy terminal direction, in accordance with standard usage and convention.

Similarly, unless otherwise specified, the lefthand end of single-stranded polynucleotide sequences is the 5'-end and the lefthand direction of double-stranded polynucleotide sequences is referred to as the 5' direction.

Those skilled in the art would be able to design and prepare appropriate mutants of the proteins described herein by using techniques known in the art. For example, when targeting a region which appears to be less important for the biological activity of the protein of the present invention, it is possible to identify a suitable region in the protein molecule whose structure can be changed without impairing the biological activity of the protein of the present invention. It is also possible to identify residues or regions in the molecule, which are conserved between similar proteins. Moreover, it is also possible to introduce conservative amino acid substitutions into a region which appears to be important for the biological activity or structure of the protein of the present invention, without impairing the biological activity and without adversely affecting the polypeptide structure of the protein.

For example, MaACL1 and MaACL2 of the present invention share an amino acid sequence identity of about 62% with a basidiomycetes U. maydis-derived ACL-like putative protein (gi_46096782), and also share a certain identity with animal-derived ACL or ACL-like putative protein sequences including mouse (gi_29293809), human (gi_38569421), Drosophila (gi_28372804) and nematode (gi_17551266) (FIG. 5). By way of example for possible amino acid residues to be mutated, residues other than those conserved among all of the 7 sequences shown in FIG. 5 may be determined to be possible amino acid residues to be mutated, or alternatively, residues other than those conserved among at least 4, 5 or 6 sequences of these 7 sequences may be determined to be possible amino acid residues to be mutated.

Alternatively, the three underlined regions indicated respectively by solid, dotted and double lines in FIG. 5 are particularly important sites for ATP:citrate lyase/succinyl-CoA lyase (PROSITE, PS01216, PS00399 and PS01217, respectively, from the N-terminal side). Namely, mutants according to the present invention are not limited in any way as long as the above sites are conserved. Thus, by way of another example for possible amino acid residues to be mutated, amino acid residues other than those of the three underlined regions shown in FIG. 5 may be determined to be possible amino acid residues to be mutated.

Moreover, MaACL1 and MaACL2 of the present invention share an amino acid identity of 87.1% with each other (FIG. 4). By way of yet another example for possible amino acid residues to be mutated, residues that are not conserved between MaACL1 and MaACL2 may be determined to be possible amino acid residues to be mutated.

Those skilled in the art would be able to conduct a so-called structure-function study which identifies residues, in the protein of the present invention and in a similar peptide thereof, that are important for biological activity or structure, and compares amino acid residues between these two peptides, thereby predicting which residues in the protein similar to the protein of the present invention are amino acid residues corresponding to those important for biological activity or structure. Moreover, chemically similar amino acid substitutions may be chosen for the amino acid residues thus predicted to thereby select a mutant which retains the biological activity of the protein of the present invention. Likewise, those skilled in the art would also be able to analyze the three-dimensional structure and amino acid sequence of this protein mutant. The analysis results thus obtained can further be used to predict the alignment of amino acid residues with respect to the three-dimensional structure of the protein. Since amino acid residues predicted to be on the protein surface may be involved in important interactions with other molecules, those skilled in the art would be able to prepare a mutant which causes no change in these amino acid residues predicted to be on the protein surface, on the basis of analysis results as mentioned above. Moreover, those skilled in the art would also be able to prepare a mutant having a single amino acid substitution for any of the amino acid residues constituting the protein of the present invention. These mutants may be screened by any known assay to collect information about the individual mutants, which in turn allows evaluation of the usefulness of individual amino acid residues constituting the protein of the present invention when a comparison is made with the following case where a mutant having substitution of a specific amino acid residue shows lower biological activity than that of the protein of the present invention, where such a mutant shows no biological activity, or where such a mutant produces unsuitable activity to inhibit the biological activity of the protein of the present invention. Moreover, based on information collected from such routine experiments, those skilled in the art may readily analyze amino acid substitutions undesirable for mutants of the protein of the present invention either alone or in combination with other mutations.

As described above, a protein consisting of an amino acid sequence with deletion, substitution or addition of one or more amino acids in the amino acid sequence shown in SEQ ID NO: 11 or 12 can be prepared according to techniques such as site-directed mutagenesis as described in "Molecular Cloning, A Laboratory Manual 3rd ed." (Cold Spring Harbor Press (2001)), "Current Protocols in Molecular Biology" (John Wiley & Sons (1987-1997), Kunkel (1985) Proc. Natl. Acad. Sci. USA 82: 488-92, and Kunkel (1988) Method. Enzymol. 85: 2763-6. Preparation of a mutant with such a mutation including amino acid deletion, substitution or addition may be accomplished, for example, by known procedures such as Kunkel method or Gapped duplex method using a mutation-introducing kit based on site-directed mutagenesis such as a QuikChange™ Site-Directed Mutagenesis Kit (Stratagene), a GeneTailor™ Site-Directed Mutagenesis System (Invitrogen) or a TaKaRa Site-Directed Mutagenesis System (e.g., Mutan-K, Mutan-Super Express Km; Takara Bio Inc., Japan).

Techniques for allowing deletion, substitution or addition of one or more amino acids in the amino acid sequences of proteins while retaining their activity include site-directed mutagenesis mentioned above, as well as other techniques such as those for treating a gene with a mutagen, and those in which a gene is selectively cleaved to remove, substitute or add a selected nucleotide or nucleotides, and then ligated.

A preferred nucleotide sequence contained in the nucleic acids of the present invention is a nucleotide sequence which encodes a protein consisting of an amino acid sequence with deletion, substitution or addition of 1 to 10 amino acids in the amino acid sequence shown in SEQ ID NO: 11 or 12 and having ACL activity.

There is no limitation on the number or sites of amino acid mutations or modifications in the protein of the present invention, as long as the resulting mutant retains ACL activity or enzyme activity properties equal to those of a protein encoded by the nucleotide sequence of the present invention or a protein consisting of the amino acid sequence of the present invention.

(b) A nucleotide sequence which is hybridizable under stringent conditions with a nucleic acid consisting of a nucleotide sequence complementary to a nucleotide sequence consisting of SEQ ID NO: 9 or SEQ ID NO: 10 and which encodes a protein having the above activity of the present invention Nucleotide sequences contained in the nucleic acids of the present invention include a nucleotide sequence which is hybridizable under stringent conditions with a nucleic acid consisting of a nucleotide sequence complementary to a nucleotide sequence consisting of SEQ ID NO: 9 or SEQ ID NO: 10 and which encodes a protein having the above activity of the present invention.

SEQ ID NO: 9 or SEQ ID NO: 10 and the above activity of the present invention are as described above.

To obtain the above nucleotide sequence, an appropriate probe may be prepared in a manner known to those skilled in the art, and this probe may be used in known hybridization techniques such as colony hybridization, plaque hybridization or Southern blotting to obtain the nucleotide sequence from a cDNA library, a genomic library or the like.

As to detailed procedures for hybridization techniques, reference may be made to "Molecular Cloning, A Laboratory Manual 3rd ed." (Cold Spring Harbor Press (2001); particularly Sections 6-7), "Current Protocols in Molecular Biology" (John Wiley & Sons (1987-1997); particularly Sections 6.3-6.4), "DNA Cloning 1: Core Techniques, A Practical Approach 2nd ed." (Oxford University (1995); particularly Section 2.10 for hybridization conditions).

The strength of hybridization is determined primarily by hybridization conditions, more preferably by hybridization conditions and washing conditions. The term "stringent conditions" as used herein is intended to include moderately or highly stringent conditions.

More specifically, moderately stringent conditions include, for example, hybridization conditions of 1×SSC to 6×SSC at 42° C. to 55° C., more preferably 1×SSC to 3×SSC at 45° C. to 50° C., and most preferably 2×SSC at 50° C. In certain cases such as where a hybridization solution contains about 50% formamide, a temperature which is 5° C. to 15° C. lower than the above temperature is used. Washing conditions may be 0.5×SSC to 6×SSC at 40° C. to 60° C. During hybridization and washing, 0.05% to 0.2% SDS, preferably about 0.1% SDS may usually be added.

Highly stringent (high stringent) conditions include hybridization and/or washing at higher temperature and/or lower salt concentration, compared to the moderately stringent conditions. For example, hybridization conditions may be 0.1×SSC to 2×SSC at 55° C. to 65° C., more preferably 0.1×SSC to 1×SSC at 60° C. to 65° C., and most preferably 0.2×SSC at 63° C. Washing conditions may be 0.2×SSC to 2×SSC at 50° C. to 68° C., and more preferably 0.2×SSC at 60° C. to 65° C.

Hybridization conditions particularly used in the present invention include, but are not limited to, prehybridization in 5×SSC, 1% SDS, 50 mM Tris-HCl (pH 7.5) and 50% formamide at 42° C., overnight incubation at 42° C. in the presence of a probe to form hybrids, and the subsequent three washings in 0.2×SSC, 0.1% SDS at 65° C. for 20 minutes.

It is also possible to use a commercially available hybridization kit which uses no radioactive substance as a probe. Specific examples include hybridization with a DIG nucleic acid detection kit (Roche Diagnostics) or with an ECL direct labeling & detection system (Amersham).

A preferred nucleotide sequence falling within the present invention is a nucleotide sequence which is hybridizable under conditions of 2×SSC at 50° C. with a nucleic acid consisting of a nucleotide sequence complementary to a nucleotide sequence consisting of SEQ ID NO: 9 or SEQ ID NO: 10 and which encodes a protein having ACL activity.

(c) A nucleotide sequence which consists of a nucleotide sequence sharing an identity of 70% or more with a nucleotide sequence consisting of SEQ ID NO: 9 or SEQ ID NO: 10 and which encodes a protein having the above activity of the present invention Nucleotide sequences contained in the nucleic acids of the present invention include a nucleotide sequence which consists of a nucleotide sequence sharing an identity of 70% or more with a nucleotide sequence consisting of SEQ ID NO: 9 or SEQ ID NO: 10 and which encodes a protein having the above activity of the present invention.

Preferred examples include nucleic acids comprising a nucleotide sequence which shares an identity of at least 75%, more preferably 80%, even more preferably 85% (e.g., 90%, 95%, more particularly 98% or 99%) with the nucleic acid sequence shown in SEQ ID NO: 9 or 10 and which encodes a protein having the above activity of the present invention. As described above, the identity between MaACL1 (SEQ ID NO: 9) and MaACL2 (SEQ ID NO: 10) is 79.1%. The nucleic acids of the present invention include those being at least 80% or more of the nucleic acid sequence shown in SEQ ID NO: 9 or 10 and being similar to these two sequences.

The percent identity between two nucleic acid sequences can be determined by visual inspection and mathematical calculation, or more preferably by using a computer program to compare sequence information between two nucleic acids. Computer programs for sequence comparison include, for example, the BLASTN program (Altschul et al. (1990) J. Mol. Biol. 215: 403-10) version 2.2.7, available for use via the National Library of Medicine website: http://www.ncbi.nlm.nih.gov/blast/bl2seq/bls.html, or the WU-BLAST 2.0 algorithm. Standard default parameter settings for WU-BLAST 2.0 are described at the following Internet site: http://blast.wustl.edu.

(d) A nucleotide sequence which encodes an amino acid sequence sharing an identity of 70% or more with an amino acid sequence consisting of SEQ ID NO: 11 or SEQ ID NO: 12 and which encodes a protein having the above activity of the present invention Nucleotide sequences contained in the nucleic acids of the present invention include a nucleotide sequence which encodes an amino acid sequence sharing an identity of 70% or more with an amino acid sequence consisting of SEQ ID NO: 11 or SEQ ID NO: 12 and which encodes a protein having the above activity of the present invention. Proteins encoded by the nucleic acids of the present invention may also be those sharing identity with the amino acid sequence of MaACL1 or MaACL2, as long as they are functionally equivalent to proteins having the above activity of the present invention.

Specific examples include amino acid sequences sharing an identity of 75% or more, preferably 85% or more, more preferably 88% (e.g., 90%, 95%, 98%, more particularly 99%) or more with the amino acid sequence shown in SEQ ID NO: 11 or SEQ ID NO: 12. As described above, the amino acid sequence identity between MaACL1 (SEQ ID NO: 11) and MaACL2 (SEQ ID NO: 12) is 87.1%. Proteins encoded by the nucleic acids of the present invention include those being at least 88% or more of the amino acid sequence shown in SEQ ID NO: 11 or 12 and being similar to these two sequences.

A preferred nucleotide sequence contained in the nucleic acids of the present invention is a nucleotide sequence which encodes an amino acid sequence sharing an identity of 90% or more with an amino acid sequence consisting of SEQ ID NO: 11 or SEQ ID NO: 12 and which encodes a protein having the above activity of the present invention. More preferred is a nucleotide sequence which encodes an amino acid sequence sharing an identity of 95% or more with an amino acid sequence consisting of SEQ ID NO: 11 or SEQ ID NO: 12 and which encodes a protein having the above activity of the present invention.

The percent identity between two amino acid sequences may be determined by visual inspection and mathematical calculation. Alternatively, the percent identity may be determined by using a computer program. Examples of such a computer program include BLAST, FASTA (Altschul et al., J. Mol. Biol., 215:403-410 (1990)) and ClustalW. In particular, various conditions (parameters) for an identity search with the BLAST program are described by Altschul et al. (Nucl. Acids. Res., 25, p. 3389-34.02, 1997) and publicly available via the website of the National Center for Biotechnology Information (NCBI) or the DNA Data Bank of Japan (DDBJ) (BLAST Manual, Altschul et al., NCB/NLM/NIH Bethesda, Md. 20894; Altschul et al.). It is also possible to use a program such as genetic information processing software GENETYX Ver. 7 (Genetyx Corporation, Japan), DINASIS Pro (Hitachisoft, Japan) or Vector NTI (Infomax) for determination of the percent identity.

Certain alignment schemes for aligning amino acid sequences may also result in matching of a specific short region of the sequences, and it is also possible to detect a region with very high sequence identity in such a small aligned region even when there is no significant relationship between the full-length sequences used. In addition, the BLAST algorithm uses the BLOSUM62 amino acid scoring matrix, and optional parameters that can be used are as follows: (A) inclusion of a filter to mask segments of the query sequence that have low compositional complexity (as determined by the SEG program of Wootton and Federhen (Computers and Chemistry, 1993); also see Wootton and Federhen, 1996, "Analysis of compositionally biased regions in sequence databases," Methods Enzymol., 266: 554-71) or segments consisting of short-periodicity internal repeats (as determined by the XNU program of Clayerie and States (Computers and Chemistry, 1993)), and (B) a statistical significance threshold for reporting matches against database sequences, or E-score (the expected probability of matches being found merely by chance, according to the stochastic model of Karlin and Altschul, 1990; if the statistical significance ascribed to a match is greater than this E-score threshold, the match will not be reported).

(e) A nucleotide sequence which is hybridizable under stringent conditions with a nucleic acid consisting of a nucleotide sequence complementary to a nucleotide sequence encoding a protein consisting of the amino acid sequence shown in SEQ ID NO: 11 or 12 and which encodes a protein having the above activity of the present invention Nucleotide sequences contained in the nucleic acids of the present invention include a nucleotide sequence which is hybridizable under stringent conditions with a nucleic acid consisting of a nucleotide sequence complementary to a nucleotide sequence encoding a protein consisting of the amino acid sequence shown in SEQ ID NO: 11 or 12 and which encodes a protein having the above activity of the present invention.

Such a protein consisting of the amino acid sequence shown in SEQ ID NO: 11 or 12 and hybridization conditions are as described above.

The nucleic acids of the present invention also include a nucleic acid which comprises a nucleotide sequence with deletion, substitution or addition of one or more nucleotides in a nucleotide sequence consisting of SEQ ID NO: 9 or SEQ ID NO: 10 and encoding a protein having the above activity of the present invention. More specifically, it is also possible to use a nucleic acid which comprises a nucleotide sequence selected from:

(i) a nucleotide sequence with deletion of one or more (preferably one or several (e.g., 1-1050, 1-750, 1-700, 1-650, 1-600, 1-550, 1-500, 1-450, 1-400, 1-350, 1-300, 1-250, 1-200, 1-150, 1-100, 1-50, 1-30, 1-25, 1-20, 1-15, 1-10, more preferably 1-5)) nucleotides in the nucleotide sequence shown in SEQ ID NO: 9 or 10;

(ii) a nucleotide sequence with substitution of other nucleotides for one or more (preferably one or several (e.g., 1-1050, 1-750, 1-700, 1-650, 1-600, 1-550, 1-500, 1-450, 1-400, 1-350, 1-300, 1-250, 1-200, 1-150, 1-100, 1-50, 1-30, 1-25, 1-20, 1-15, 1-10, more preferably 1-5)) nucleotides in the nucleotide sequence shown in SEQ ID NO: 9 or 10;

(iii) a nucleotide sequence with addition of other one or more (preferably one or several (e.g., 1-1050, 1-750, 1-700, 1-650, 1-600, 1-550, 1-500, 1-450, 1-400, 1-350, 1-300, 1-250, 1-200, 1-150, 1-100, 1-50, 1-30, 1-25, 1-20, 1-15, 1-10, more preferably 1-5)) nucleotides in the nucleotide sequence shown in SEQ ID NO: 9 or 10; or (iv) a nucleotide sequence with any combination of (i) to (iii) above, and encoding a protein having the above activity of the present invention.

Preferred embodiments for the nucleic acids of the present invention also include a nucleic acid comprising a nucleotide sequence shown in any one of (a) to (c) below or a fragment thereof:

(a) the nucleotide sequence shown in SEQ ID NO: 9 or SEQ ID NO: 10;

(b) a nucleotide sequence encoding a protein consisting of the amino acid sequence shown in SEQ ID NO: 11 or SEQ ID NO: 12; or (c) the nucleotide sequence shown in SEQ ID NO: 5 or SEQ ID NO: 6.

The above (a) nucleotide sequence shown in SEQ ID NO: 9 or SEQ ID NO: 10, (b) nucleotide sequence encoding a protein consisting of the amino acid sequence shown in SEQ ID NO: 11 or 12, and (c) nucleotide sequence shown in SEQ ID NO: 5 or 6 are as shown in Table 1. Fragments of these sequences may be either naturally occurring or artificially prepared, including regions contained in the above nucleotide sequences, i.e., ORF, CDS, a biologically active region, a region used as a primer as described later, and a region which may serve as a probe.

ATP:Citrate Lyase Proteins of the Present Invention

The proteins of the present invention, which may be either naturally occurring or artificially prepared, include a protein consisting of the amino acid sequence shown in SEQ ID NO: 11 or 12 and proteins functionally equivalent to this protein. Such a protein consisting of the amino acid sequence shown in SEQ ID NO: 11 or 12 is as described above. "Proteins functionally equivalent" are intended to mean proteins having "the above activity of the present invention," as explained in the section "Nucleic acids of the present invention encoding ATP:citrate lyase" described above.

In the present invention, proteins functionally equivalent to a protein consisting of the amino acid sequence shown in SEQ ID NO: 11 or 12 include a protein shown in (a) or (b) below:

(a) a protein which consists of an amino acid sequence with deletion, substitution or addition of one or more amino acids in SEQ ID NO: 11 or SEQ ID NO: 12 and which has the above activity of the present invention; or (b) a protein which consists of an amino acid sequence sharing an identity of 70% or more with an amino acid sequence consisting of SEQ ID NO: 11 or SEQ ID NO: 12 and which has the above activity of the present invention.

Among the above, the amino acid sequence with deletion, substitution or addition of one or more amino acids in SEQ ID NO: 11 or 12 or the amino acid sequence sharing an identity of 70% or more with an amino acid sequence consisting of SEQ ID NO: 11 or SEQ ID NO: 12 is as explained in the section "Nucleic acids of the present invention encoding ATP: citrate lyase" described above. The phrase "protein which has the above activity of the present invention" is intended to also include mutants of a protein encoded by a nucleic acid comprising the nucleotide sequence of SEQ ID NO: 9 or SEQ ID NO: 10, or mutated proteins with various modifications such as substitution, deletion or addition of one or more amino acids in the amino acid sequence shown in SEQ ID NO: 11 or 12, as well as their modified proteins whose amino acid side chains or the like are modified, and their fusion proteins with other proteins, as long as these proteins have ACL activity.

The proteins of the present invention may also be artificially prepared by chemical synthesis techniques such as Fmoc method (fluorenylmethyloxycarbonyl method) and tBoc method (t-butyloxycarbonyl method). In addition, peptide synthesizers available from Advanced ChemTech, Perkin Elmer, Pharmacia, Protein Technology Instrument, Synthecell-Vega, PerSeptive, Shimadzu Corporation (Japan) or other manufacturers may be used for chemical synthesis.

Cloning of ACL Nucleic Acids

The ACL nucleic acids of the present invention can be cloned, for example, by screening from a cDNA library using an appropriate probe. They can also be cloned by PCR amplification with appropriate primers and the subsequent ligation to an appropriate vector. The clones thus obtained may further be subcloned into another vector.

For example, it is possible to use commercially available plasmid vectors including pBlue-Script™ SK(+) (Stratagene), pGEM-T (Promega), pAmp (TM: Gibco-BRL), p-Direct (Clontech) and pCR2.1-TOPO (Invitrogen). In the case of using PCR amplification, primers may be any regions of the nucleotide sequence shown in, e.g., SEQ ID NO: 5 or 6. Then, PCR is performed on cDNA prepared from *M. alpina* cells with the above primers and DNA polymerase or the like. Although this procedure can be readily accomplished by those skilled in the art according to, e.g., "Molecular Cloning, A Laboratory Manual 3rd ed." (Cold Spring Harbor Press (2001)), PCR conditions in the present invention may be set as follows, by way of example:

Denaturation temperature: 90-95° C.
Annealing temperature: 40-60° C.
Elongation temperature: 60-75° C.
Number of cycles: 10 or more cycles.

The resulting PCR products may be purified in a known manner, for example, by using a kit (e.g., GENECLEAN (Funakoshi Co., Ltd., Japan), QIAquick PCR purification Kits (QIAGEN), ExoSAP-IT (GE Healthcare Bio-Sciences)), a DEAE-cellulose filter or a dialysis tube. In the case of using an agarose gel, the PCR products are subjected to agarose gel electrophoresis and nucleic acid fragments are excised from the agarose gel, followed by purification with GENECLEAN (Funakoshi Co., Ltd., Japan) or QIAquick Gel extraction Kits (QIAGEN) or by the freeze-squeeze method, etc.

The cloned nucleic acids can be determined for their nucleotide sequences with a nucleotide sequencer.

Vector Construction for ACL Expression and Transformant Preparation

The present invention also provides a recombinant vector comprising a nucleic acid encoding MaACL1 or MaACL2 of the present invention. The present invention further provides a transformant transformed with the above recombinant vector.

Such a recombinant vector and transformant can be obtained as follows. Namely, a plasmid carrying a nucleic acid encoding the ACL of the present invention is digested with restriction enzymes. This digestion may be followed by blunt ending with T4 polymerase. The digested DNA fragment is purified by agarose gel electrophoresis. This DNA fragment may be integrated into an expression vector in a known manner to obtain a vector for ACL expression. This expression vector is introduced into a host to prepare a transformant, which is then provided for expression of a desired protein.

In this case, the types of expression vector and host are not limited in any way as long as they allow expression of a desired protein. Examples of a host include fungi, bacteria, plants, animals or cells thereof. Fungi include filamentous fungi such as lipid-producing *M. alpina*, and yeast strains such as *Saccharomyces cerevisiae*. Bacteria include *Escherichia coli* (*E. coli*) and *Bacillus subtilis*. Likewise, plants include oil plants such as rapeseed, soybean, cotton, safflower and flax.

As lipid-producing strains, those such as found in MYCO-TAXON, Vol. XLIV, NO. 2, pp. 257-265 (1992) can be used. Specific examples include microorganisms belonging to the genus *Mortierella*, as exemplified by microorganisms belonging to the subgenus *Mortierella* such as *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS 219.35, CBS224.37, CBS250.53, CBS343.66, CBS527.72, CBS528.72, CBS529.72, CBS608.70, CBS754.68, as well as microorganisms belonging to the subgenus *Micromucor* such as *Mortierella isabellina* CBS194.28, IFO6336, IFO7824, IFO7873, IFO7874, IFO8286, IFO8308, IFO7884, *Mortierella* nana IFO8190, *Mortierella ramanniana* IFO5426, IFO8186, CBS112.08, CBS212.72, IFO7825, IFO8184, IFO8185, IFO8287, *Mortierella vinacea* CBS236.82. Particularly preferred is *Mortierella alpina*.

When a fungus is used as a host, it is desirable that the nucleic acid of the present invention is self-replicable in the host or has a structure insertable onto the fungal chromosome. At the same time, it is preferable to further comprise a promoter and a terminator. When *M. alpina* is used as a host, examples of an expression vector include pD4, pDuraSC and pDura5. Any promoter may be used as long as it allows expression in the host, and examples include promoters derived from *M. alpina*, such as histonH4.1 gene promoter, GAPDH (glyceraldehyde-3-phosphate dehydrogenase) gene promoter and TEF (translation elongation factor) gene promoter.

Techniques for introducing a recombinant vector into filamentous fungi (e.g., *M. alpina*) include electroporation, spheroplast and particle delivery methods, as well as direct microinjection of DNA into nuclei. In the case of using an auxotrophic host strain, strains growing on a selective medium lacking nutrients required for the host strain may be selected to thereby obtain transformed strains. Alternatively, in a case where a drug resistance marker gene is used for transformation, culture may be carried out with a selective medium containing the drug to thereby obtain cell colonies resistant to the drug.

When yeast is used as a host, examples of an expression vector include pYE22m. Alternatively, commercially available yeast expression vectors such as pYES (Invitrogen) and pESC (STRATAGENE) may also be used. Yeast hosts suitable for the present invention include, but are not limited to, *Saccharomyces cerevisiae* strain EH13-15 (trp1, MATα). Examples of a promoter available for use include those derived from yeast or the like, such as GAPDH promoter, gal1 promoter and gal10 promoter.

Techniques for introducing a recombinant vector into yeast cells include lithium acetate, electroporation and spheroplast methods, as well as dextran-mediated transfection, calcium phosphate precipitation, polybrene-mediated transfection, protoplast fusion, encapsulation of polynucleotide(s) in liposomes, and direct microinjection of DNA into nuclei.

When a bacterium such as *E. coli* is used as a host, examples of an expression vector include pGEX and pUC18 available from Pharmacia. Examples of a promoter available for use include those derived from *E. coli*, phage or the like, such as trp promoter, lac promoter, PL promoter and PR promoter. Techniques for introducing a recombinant vector into bacteria include electroporation and calcium chloride methods.

Method of the Present Invention for Preparing Fatty Acids or Lipids

The present invention provides a method for preparing fatty acids or lipids from the above transformant, i.e., a method for preparing fatty acids or lipids from a cultured product obtained by culturing the above transformant, more specifically as described below. However, the method of the present invention is not limited to the following, and may be accomplished in any other manner generally known.

For culture of organisms transformed to express ACL, any medium may be used as long as it is a culture solution (medium) having appropriate pH and osmotic pressure as well as containing nutrients required for growth of each host, trace elements, and biomaterials such as serum or antibiotics. For example, in the case of *M. alpina* transformed to express ACL, a medium having the composition shown below or the like may be used without being limited thereto:

(1) 1.8% glucose, 1% soybean powder, 0.1% olive oil, 0.01% Adekanol, 0.3% $KH_2PO_4$, 0.1% $Na_2SO_4$, 0.05% $CaCl_2.2H_2O$, 0.05% $MgCl_2.6H_2O$ (pH 6.0); or (2) GY medium (2.0% glucose, 1.0% yeast extract)

Any culture conditions may be used as long as they are suitable for host growth and are adequate for maintenance of the generated enzyme in a stable state. More specifically, individual conditions may be adjusted, including anaerobic degree, culture period, temperature, humidity, static culture or shaking culture. Culture may be accomplished under the same conditions (one-step culture) or by so-called two-step or three-step culture using two or more different culture conditions. For large-scale culture, two-step or more step culture is preferred because of its high culture efficiency.

To explain detailed procedures for the method of the present invention for preparing fatty acids, culture in which *M. alpina* is used as a host will be illustrated below as an example. Namely, a transformed strain carrying MaACL1 or MaACL2 of the present invention is inoculated into GY medium, and shaking culture is initiated at 28° C. Then, on day 3 of culture, a 20% glucose solution is added to the culture solution in a ½₀ volume, and shaking culture is continued for 8 days or more in total.

The fatty acids or lipids of the present invention can be extracted in the following manner. However, the method of the present invention is not limited to the following, and may be accomplished in any other manner generally known. More specifically, the fatty acids or lipids of the present invention can be extracted as follows from microbial cells, which have been transformed in accordance with the present invention. A transformed strain of an organism (e.g., a lipid-producing fungus or yeast) is cultured and then treated in a routine manner, e.g., by centrifugation or filtration to obtain cultured cells. The cells were washed well with water and preferably further dried. Drying may be accomplished by freeze-drying, air-drying, etc. The dried cells are optionally crushed with a Dynomil or by ultrasonication, and then extracted with an organic solvent preferably under a nitrogen stream. Examples of an organic solvent available for use include ether, hexane, methanol, ethanol, chloroform, dichloromethane, petroleum ether and so on. Alternatively, good results can also be obtained by alternating extraction with methanol and petroleum ether or by extraction with a single-phase solvent system of chloroform-methanol-water. When the organic solvent is distilled off from the extract under reduced pressure, fatty acid-containing lipids can be obtained.

Moreover, fatty acids can be separated in a state of mixed fatty acids or mixed fatty acid esters from the above fatty acid-containing lipids by concentration and separation in a routine manner (e.g., urea addition, separation under cooling, column chromatography).

The method of the present invention for preparing lipids or fatty acids enables the efficient production of fatty acids due to increased fatty acid content in microbial cells.

As an actual example for the method of the present invention for preparing fatty acids, when *M. alpina* was used as a host to create a transformed strain carrying MaACL1 or MaACL2 of the present invention, from which fatty acids were then actually extracted, the fatty acid content in these microbial cells was found to increase about 1.1-fold when compared to a control strain which was not transformed with ACL.

Fatty Acids or Lipids of the Present Invention

The present invention also provides fatty acids and lipids in cells expressing MaACL1 or MaACL2 of the present invention. Fatty acids may be free fatty acids or may be triglycerides, phospholipids or the like.

As used herein, the term "fatty acid" refers to a linear or branched monocarboxylic acid of a long-chain carbohydrate, represented by the formula ROOH (wherein R is an alkyl group). Examples include, but are not limited to, myristic acid (tetradecanoic acid) (14:0), myristoleic acid (tetradecenoic acid) (14:1), palmitic acid (hexadecanoic acid) (16:0), palmitoleic acid (9-hexadecenoic acid) (16:1), stearic acid (octadecanoic acid) (18:0), oleic acid (cis-9-octadecenoic acid) (18:1(9)), vaccenic acid (11-octadecenoic acid) (18:1(11)), linolic acid (cis,cis-9,12 octadecadienoic acid) (18:2(9,12)), α-linolenic acid (9,12,15-octadecatrienoic acid) (18:3(9,12,15)), γ-linolenic acid (6,9,12-octadecatrienoic acid) (18:3(6,9,12)), stearidonic acid (6,9,12,15-octadecatetraenoic acid) (18:4(6,9,12,15)), arachidic acid (icosanoic acid) (20:0), (8,11-icosadienoic acid) (20:2(8,11)), mead acid (5,8,11-icosatrienoic acid) (20:3(5,8,11)), dihomo-γ-linolenic acid (8,11,14-icosatrienoic acid) (20:3(8,11,14)), arachidonic acid (5,8,11,14-icosatetraenoic acid) (20:4(5,8,11,14)), eicosatetraenoic acid (8,11,14,17-icosatetraenoic acid) (20:4(8,11,14,17)), eicosapentaenoic acid (5,8,11,14,17-icosapentaenoic acid) (20:5(5,8,11,14,17)), behenic acid (docosanoic acid) (22:0), (7,10,13,16-docosatetraenoic acid) (22:4(7,10,13,16)), (7,10,13,16,19-docosapentaenoic acid) (22:5(7,10,13,16,19)), (4,7,10,13,16-docosapentaenoic acid) (22:5(4,7,10,13,16)), (4,7,10,13,16,19-docosahexaenoic acid) (22:6(4,7,10,13,16,19)), lignoceric acid (tetradocosanoic acid) (24:0), nervonic acid (cis-15-tetradocosanoic acid) (24:1) and cerotic acid (hexadocosanoic acid) (26:0). It should be noted that the above substance names are common names defined by the IUPAC Biochemical Nomenclature, and their systematic names are given in parentheses along with numerics denoting the number of carbons and the positions of double bonds.

As used herein, the term "lipid" is intended to mean a simple lipid including a compound (e.g., glyceride) which is composed of a fatty acid and an alcohol attached via an ester linkage, or an analog (e.g., cholesterol ester) thereof; a complex lipid which is generated from such a simple lipid by partial modification with phosphoric acid, amino acid(s), saccharide(s) or the like; or a derived lipid which is a hydrolysate of the above lipid and is not soluble in water.

The fatty acid composition of the present invention may be composed of any number and any type of fatty acids, as long as it is a combination of one or more fatty acids selected from those listed above.

Food or Other Products Comprising Fatty Acids or Lipids of the Present Invention The present invention also provides a food product comprising the above fatty acids or lipids. The fatty acids or lipids of the present invention can be used in a routine manner for purposes such as production of food products containing fats and oils as well as production of industrial source materials (those for cosmetics, pharmaceuticals (e.g., external preparations for skin), soaps, etc.). Cosmetics (cosmetic compositions) or pharmaceuticals (pharmaceutical compositions) may be formulated into any dosage form including, but not limited to, solutions, pastes, gels, solids or powders. Likewise, possible forms of food products include pharmaceutical formulations such as capsules, as well as processed foods such as ordinary fluid diets, semi-digested nourishing diets, elemental diets, drinkable preparations or enteral nutrient preparations, which comprise the fatty acids or lipids of the present invention in admixture with proteins, sugars, fats, trace elements, vitamins, emulsifiers, flavorings, etc.

Moreover, examples of the food product of the present invention include, but are not limited to, nutritional supplementary foods, health foods, functional foods, children's foods, infant modified milk, premature infant modified milk, and geriatric foods. The term "food" or "food product" is used herein as a generic name for edible materials in the form of solids, fluids, liquids or mixtures thereof.

The term "nutritional supplementary foods" refers to food products enriched with specific nutritional ingredients. The term "health foods" refers to food products that are healthful or good for health, and encompasses nutritional supplementary foods, natural foods and diet foods. The term "functional foods" refers to food products for replenishing nutritional ingredients which assist body control functions. Functional foods are synonymous with foods for specified health use. The term "children's foods" refers to food products given to children up to about 6 years old. The term "geriatric foods" refers to food products treated to facilitate digestion and absorption when compared to untreated foods. The term "infant modified milk" refers to modified milk given to children up to about one year old. The term "premature infant modified milk" refers to modified milk given to premature infants until about 6 months after birth.

These food products include natural foods (treated with fats and oils) such as meat, fish and nuts; foods supplemented with fats and oils during preparation (e.g., Chinese foods, Chinese noodles, soups); foods prepared using fats and oils as heating media (e.g., tempura (deep-fried fish and vegetables), deep-fried foods, fried bean curd, Chinese fried rice, doughnuts, Japanese fried dough cookies (karinto)); fat- and oil-based foods or processed foods supplemented with fats and oils during processing (e.g., butter, margarine, mayonnaise, dressing, chocolate, instant noodles, caramel, biscuits, cookies, cake, ice cream); and foods sprayed or coated with fats and oils upon finishing (e.g., rice crackers, hard biscuits, sweet bean paste bread). However, the food product of the present invention is not limited to foods containing fats and oils, and other examples include agricultural foods such as bakery products, noodles, cooked rice, sweets (e.g., candies, chewing gums, gummies, tablets, Japanese sweets), bean curd and processed products thereof; fermented foods such as Japanese rice wine (sake), medicinal liquor, sweet cooking sherry (mirin), vinegar, soy sauce and miso (bean paste); livestock food products such as yoghurt, ham, bacon and sausage; seafood products such as fish cake (kamaboko), deep-fried fish cake (ageten) and puffy fish cake (hanpen); as well as fruit drinks, soft drinks, sports drinks, alcoholic beverages, and tea.

Method for Strain Evaluation or Selection Using ACL-Encoding Nucleic Acid or ACL Protein of the Present Invention The present invention also provides a method for evaluating or selecting a lipid-producing strain using the ACL-encoding nucleic acid or ACL protein of the present invention. Details are given below.

(1) Evaluation Method

One embodiment of the present invention is a method for evaluating a lipid-producing strain using the ACL-encoding nucleic acid or ACL protein of the present invention. As a first example for the above evaluation method of the present invention, lipid-producing test strains are evaluated for the above activity of the present invention by using primers or probes designed based on the nucleotide sequence of the present invention. General procedures for such evaluation are known and can be found in, e.g., International Patent Publication No. WO01/040514 or JP 8-205900 A. A brief explanation will be given below of this evaluation.

First, the genome of a test strain is prepared. For genome preparation, it is possible to use any known technique such as Hereford method or potassium acetate method (see, e.g., Methods in Yeast Genetics, Cold Spring Harbor Laboratory Press, p 130 (1990)).

Primers or probes are designed based on the nucleotide sequence of the present invention, preferably SEQ ID NO: 9 or 10. These primers or probes may be any regions of the nucleotide sequence of the present invention, and known procedures may be used for their design. The number of nucleotides in a polynucleotide used as a primer is generally 10 nucleotides or more, preferably 15 to 25 nucleotides. Likewise, the number of nucleotides appropriate for a region to be flanked by primers is generally 300 to 2000 nucleotides.

The primers or probes prepared above are used to examine whether the genome of the above test strain contains a sequence specific to the nucleotide sequence of the present invention. A sequence specific to the nucleotide sequence of the present invention may be detected using known procedures. For example, a polynucleotide comprising a part or all of a sequence specific to the nucleotide sequence of the present invention or a polynucleotide comprising a nucleotide sequence complementary to the above nucleotide sequence is used as one primer, and a polynucleotide comprising a part or all of a sequence located upstream or downstream of this sequence or a polynucleotide comprising a nucleotide sequence complementary to the above nucleotide sequence is used as the other primer to amplify nucleic acids from the test strain by PCR or other techniques, followed by determining the presence or absence of amplification products, the molecular weight of amplification products, etc.

PCR conditions suitable for the method of the present invention are not limited in any way, and may be set as follows, by way of example:

Denaturation temperature: 90-95° C.
Annealing temperature: 40-60° C.
Elongation temperature: 60-75° C.
Number of cycles: 10 or more cycles.

The resulting reaction products (i.e., DNA fragments) may be separated by electrophoresis on an agarose gel or the like to determine the molecular weight of the amplification products. Each amplification product is then confirmed as to whether its molecular weight is a size enough to cover a nucleic acid molecule corresponding to a region specific to the nucleotide sequence of the present invention, whereby the test strain can be predicted or evaluated for the above activity of the present invention. Moreover, if the above amplification products are analyzed for their nucleotide sequences, as described above, the above activity of the present invention can be predicted or evaluated with more accuracy. It should be noted that procedures for evaluating the above activity of the present invention are as described above.

As another example for the above evaluation method of the present invention, a test strain is cultured and measured for the expression level of ACL encoded by the nucleotide sequence of the present invention (e.g., SEQ ID NO: 9 or 10), whereby the test strain can be evaluated for the above activity of the present invention. It should be noted that the expression level of ACL can be measured by culturing a test strain under appropriate conditions and quantifying mRNA or protein for ACL. Quantification of mRNA or protein may be accomplished by using known procedures, for example, Northern hybridization or quantitative RT-PCR for mRNA quantification and Western blotting for protein quantification (Current Protocols in Molecular Biology, John Wiley & Sons 1994-2003). For evaluation of the above activity, it is also possible to measure the fatty acid rate of a fatty acid composition produced by the ACL of the present invention. Procedures for measuring the fatty acid rate of a fatty acid composition are as described above.

(2) Selection Method

Another embodiment of the present invention is a method for selecting a lipid-producing strain using the ACL-encoding nucleic acid or ACL protein of the present invention. As an example for the above selection method of the present invention, test strains are cultured and measured for the expression level of ACL encoded by the nucleotide sequence of the present invention (e.g., SEQ ID NO: 9 or 10) to select a strain with a desired expression level, whereby a strain having a desired activity can be selected. Alternatively, a type strain is predetermined, and this type strain and test strains are each cultured and measured for the above expression level, followed by comparison of the expression level between the type strain and each test strain, whereby a desired strain can be selected. More specifically, for example, a type strain and test strains are cultured under appropriate conditions and measured for their expression levels to select a test strain showing higher or lower expression than the type strain, whereby a strain having a desired activity can be selected. Examples of a desired activity include the expression level of ACL and the content of total fatty acids produced by ACL, which may be measured as described above.

As another example for the above selection method of the present invention, test strains are cultured to select a strain in which the above activity of the present invention is high or low, whereby a strain having a desired activity can be selected. Examples of a desired activity include the expression level of ACL and the content of total fatty acids produced by ACL, which may be measured as described above.

Examples of a test strain or type strain available for use include, but are not limited to, a strain transformed with the above vector of the present invention, a strain modified to suppress expression of the above nucleic acid of the present invention, a strain modified by mutagenesis, and a strain having natural mutation(s). It should be noted that ACL activity in the present invention can be measured, for example, by the procedures described in the section "Nucleic acids of the present invention encoding ATP:citrate lyase." Mutagenesis may be accomplished by, but not limited to, physical techniques including ultraviolet or radioactive irradiation, or chemical techniques including treatment with an agent such as EMS (ethylmethane sulfonate) or N-methyl-N-nitrosoguanidine (see, e.g., Yasuji Oshima ed., Biochemistry Experiments vol. 39, Experimental Protocols for Yeast Molecular Genetics, pp. 67-75, Japan Scientific Societies Press).

Strains used in the present invention as type and test strains include, but are not limited to, the above lipid-producing strains or yeast strains. More specifically, the type strain or test strain may be a combination of any strains belonging to different genera or species, and one or more test strains may be used simultaneously.

The present invention will now be described in more detail by way of the following examples, which are not intended to limit the scope of the invention.

Example 1

(1) EST Analysis

*M. alpina* strain 1S-4 was inoculated into 100 ml medium (1.8% glucose, 1% yeast extract, pH 6.0) and pre-cultured for 3 days at 28° C. A 10 L culture vessel (Able Co., Tokyo) was charged with 5 L medium (1.8% glucose, 1% soybean powder, 0.1% olive oil, 0.01% Adekanol, 0.3% $KH_2PO_4$, 0.1% $Na_2SO_4$, 0.05% $CaCl_2.2H_2O$, 0.05% $MgCl_2.6H_2O$, pH 6.0) and inoculated with the entire pre-cultured product, followed by aerobic spinner culture under conditions of 300 rpm, 1 vvm and 26° C. for 8 days. On days 1, 2 and 3 of culture, glucose was added in an amount corresponding to 2%, 2% and 1.5%, respectively. The cells were collected at each stage of culture (day 1, 2, 3, 6 or 8) to prepare total RNA by the guanidine hydrochloride/CsCl method. Using an Oligotex-dT30<Super>mRNA Purification Kit ('dT30' disclosed as SEQ ID NO: 41) (Takara Bio Inc., Japan), poly(A)$^+$RNA was purified from the total RNA. A cDNA library was prepared for each stage with a ZAP-cDNA GigapackIII Gold Cloning Kit (STRATAGENE), followed by one-pass sequence analysis from the 5'-end of cDNA (8000 clones×5 stages). The resulting sequences were clustered. As a result, about 5000 sequences were obtained.

(2) Search for ATP:Citrate Lyase Gene Homologs

The nucleotide sequences obtained by the EST analysis were searched against amino acid sequences registered in GENEBANK with a homology search program, BLASTX, to extract homologs of the ATP:citrate lyase gene. As a result, four ACL homolog sequences (SEQ ID NOs: 1, 2, 3 and 4) were found. SEQ ID NOs: 1 and 3 were homologous to each other and showed a hit with the same region in a *Neurospora crassa*-derived ATP:citrate lyase subunit 1-like putative protein, while SEQ ID NOs: 2 and 4 were also homologous to each other and showed a hit with the same region in a *Sordaria macrospora*-derived ATP:citrate lyase subunit 1-like putative protein. Namely, this strain had at least two or more possible ATP:citrate lyase homologs. Table 2 shows the number of clones constituting each sequence in relation to source libraries from which the clones were obtained.

TABLE 2

| Gene | SEQ ID NO | Source library | | | | |
|---|---|---|---|---|---|---|
| | | Day 1 | Day 2 | Day 3 | Day 6 | Day 8 |
| MaACL1 | SEQ ID NO: 1 | 3 | 0 | 1 | 2 | 0 |
| MaACL1 | SEQ ID NO: 2 | 0 | 1 | 0 | 0 | 0 |
| MaACL2 | SEQ ID NO: 3 | 0 | 0 | 1 | 0 | 0 |
| MaACL2 | SEQ ID NO: 4 | 0 | 0 | 0 | 0 | 1 |

Example 2

(1) Cloning of ACL Homologs

SEQ ID NOs: 1 to 4 contain no CDS appearing to encode ACL. Thus, for cloning of cDNAs encoding the full lengths of these genes, primers were prepared based on each sequence as follows.
Primers Designed Based on SEQ ID NO: 2:

```
                                      (SEQ ID NO: 18)
    Primer 422-1:    GATACCGTCGTCAACTTTGCCTC (SEQ ID NO: 19)
    Primer 422-2:    CATCTTGCAGTTGGGGTCCCGCT
```

Primers Designed Based on SEQ ID NO: 4:

```
                                      (SEQ ID NO: 20)
    Primer 424-1:    GTTGACACCGTGGTGAACTTTGCC (SEQ ID NO: 21)
    Primer 424-2:    GCATCTTGCACCCGGATCCTTCTC
```

Using these primers, PCR was performed with ExTaq (Takara Bio Inc., Japan) by using a cDNA library containing ESTs constituting SEQ ID NO: 2 or 4 as a template. The resulting DNA fragments were TA-cloned with a TOPO-TA cloning Kit (INVITROGEN CORPORATION) to determine the nucleotide sequence for each insert.

The results confirmed that DNA fragments covering nucleotides 3-443 of SEQ ID NO: 2 and nucleotides 6-449 of SEQ ID NO: 4 were each cloned. These plasmids were designated as pCR-422-P and pCR-424-P, respectively.

Then, these plasmids were each used as a template to perform PCR with the above primers. In PCR, ExTaq (Takara Bio Inc., Japan) was used, but the attached dNTP mix was replaced by a PCR labeling mix (Roche Diagnostics) for digoxigenin (DIG) labeling of DNAs to be amplified, thereby preparing probes for use in cDNA library screening. These probes were used to screen the cDNA libraries from which the ESTs constituting the individual sequences had been obtained by EST analysis.

Hybridization conditions were set as follows.
Buffer: 5×SSC, 1% SDS, 50 mM Tris-HCl (pH 7.5), 50% formamide
Temperature: 42° C. (overnight)
Washing: in 0.2×SSC, 0.1% SDS at 65° C. for 20 minutes (repeated three times)

Detection was accomplished by using a DIG nucleic acid detection kit (Roche Diagnostics). From phage clones obtained by screening, the plasmids were excised by in vivo excision to determine the nucleotide sequence for each insert. Plasmids each carrying the longest insert obtained by screening with each probe were designated as pB-ACL1 and pB-ACL2, respectively. The nucleotide sequences of the inserts in pB-ACL1 and pB-ACL2 are shown in SEQ ID NOs: 5 and 6, respectively, and in FIGS. 1 and 2, respectively. SEQ ID NO: 5 was found to contain a CDS of 3540 bp (SEQ ID NO: 7), while SEQ ID NO: 6 was found to contain a CDS of 3525 bp (SEQ ID NO: 8), thus suggesting that cDNA encoding the full length of ATP:citrate lyase homolog was obtained for each case. These genes were designated as MaACL1 and MaACL2, respectively. The deduced amino acid sequences of proteins encoded by these genes (MaACL1p and MaACL2p) are shown in SEQ ID NO: 11 and SEQ ID NO: 12, respectively.

(2) Sequence Analysis

The MaACL1 gene and the MaACL2 gene are homologous to each other and were found to share an identity of 79.1% in their CDSs (FIG. 3). Likewise, they were found to share an identity of 87.1% in their deduced amino acid sequences (FIG. 4). On the other hand, a Blast search against the NCBI protein sequence database (nr) indicated that the highest identity was observed with a basidiomycetes *U. maydis*-derived ACL-like putative protein (gi__46096782), which shared an amino acid sequence identity of 61.6% with MaACL1 and 61.9% with MaACL2. Moreover, MaACL1 and MaACL2 were also found to share a certain, but lower, identity with animal-derived ACL or ACL-like putative protein sequences including mouse (gi__29293809), human (gi__38569421), *Drosophila* (gi__ 28372804) and nematode (gi__17551266) (FIG. 5).

Example 3

(1) Construction of Yeast Expression Vectors

To express MaACL1 and MaACL2 in yeast cells, yeast expression vectors were constructed as follows. First, the plasmid pB-ACL1 was used as a template to perform PCR with ExTaq (Takara Bio Inc., Japan) using primers ACL1F-EX and ACL1R-HS.

```
                        (SEQ ID NO: 22)
Primer ACL1F-EX:  GAATTCTCTAGAATGTCTGCTAAAGCCGTTCG
                  CG (SEQ ID NO: 23)
Primer ACL1R-HS:  AAGCTTGTCGACTTAGGCCTTCTTGTTGATCG
```

The PCR product was digested with restriction enzymes EcoRI and HindIII. The resulting DNA fragment was inserted into the EcoRI-HindIII site of vector pUC18 to obtain plasmid pUC-ACL1. This was digested with restriction enzymes EcoRI and SalI to obtain a DNA fragment of approximately 3.5 kbp, which was then inserted into the EcoRI-SalI site of vector pYE22m (Biosci. Biotech. Biochem., 59, pp. 1221-1228 (1995)) to obtain plasmid pYEMaACL1. On the other hand, the plasmid pB-ACL2 was digested with restriction enzymes NotI and SalI or digested with restriction enzymes SalI and KpnI to obtain a DNA fragment of approximately 2.7 kbp or approximately 1 kbp, respectively. pYE22m was digested with a restriction enzyme EcoRI and blunt-ended with a DNA Blunting Kit (Takara Bio Inc., Japan), followed by insertion of a NotI linker (pd(GCGGCCGC)) to obtain vector pYE22mN. This vector pYE22mN was digested with restriction enzymes NotI and KpnI, and linked to the NotI-SalI and SalI-KpnI fragments of ACL2 prepared above to obtain plasmid pYEMaACL2.

(2) Yeast Transformation

The plasmid pYE22m, pYEMaACL1 or pYEMaACL2 was used to transform yeast Saccharomyces cerevisiae stratin EH13-15 (trp1, MATα) (Appl. Microbiol. Biotechnol., 30, 515-520 (1989)) by the lithium acetate method. The transformed strains were screened by the ability to grow on SC-Trp agar medium (2% agar) containing, per liter, 6.7 g Yeast nitrogen base w/o amino acids (DIFCO), 20 g glucose and 1.3 g amino acid powder (a mixture of 1.25 g adenine sulfate, 0.6 g arginine, 3 g aspartic acid, 3 g glutamic acid, 0.6 g histidine, 1.8 g leucine, 0.9 g lysine, 0.6 g methionine, 1.5 g phenylalanine, 11.25 g serine, 0.9 g tyrosine, 4.5 g valine, 6 g threonine and 0.6 g uracil).

Example 4

(1) Yeast Culture

Among the transformed strains obtained with each vector, any two strains (strains c-1 and c-2, strains MaACL1-1 and MaACL1-2, or strains MaACL2-1 and MaACL2-2) were selected and cultured under the following conditions. Namely, in the pre-culture step, a loopful of each yeast strain was inoculated from the plate into SC-Trp medium (10 ml) and cultured with shaking at 30° C. for 2 days. In the main culture step, the pre-cultured solution (1 ml) was added to SC-Trp medium (100 ml) and cultured with shaking at 30° C. for 1 day.

(2) Preparation of Enzyme Solutions

Each cultured solution was centrifuged to collect the cells, which were then washed with ½ volumes of sterilized water. The cells were suspended in 5 ml extraction buffer (50 mM Tris-HCl (pH 8.0), 1 mM EDTA, 10 mM DTT, 1 mM PMSF) and homogenized at 16 kPa with a French press, followed by centrifugation at 20,000×g at 4° C. for 10 minutes to collect the supernatant. The supernatant was applied to a PD-10 column (GE Healthcare Bio-Sciences) filled with Shehadex G-25, and eluted with elution buffer (10 mM sodium phosphate (pH 7.4), 1 mM $MgCl_2$, 0.1 mM EDTA, 1 mM DTT) to give an enzyme solution.

(3) Measurement of ACL Activity

ACL activity was determined by measuring the amount of oxaloacetate generated during the ACL-catalyzed reaction shown below, which was determined from a reduction in NADH levels (measured as a change in $A_{340}$ (6.22 $mM^{-1}$ $cm^{-1}$)) caused by the malate dehydrogenase-catalyzed reaction.

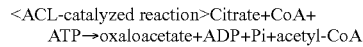

<ACL-catalyzed reaction>Citrate+CoA+ATP→oxaloacetate+ADP+Pi+acetyl-CoA

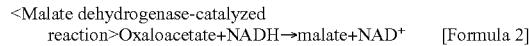

<Malate dehydrogenase-catalyzed reaction>Oxaloacetate+NADH→malate+$NAD^+$  [Formula 2]

The reaction solution was prepared in a total volume of 1 ml containing 10 mM Tris-HCl (pH 8.4), 10 mM $MgCl_2$, 1 mM DTI, 10 mM ATP, 10 mM citrate, 0.2 mM CoA, 6 units of malate dehydrogenase, 0.1 mM NADH and 50 μl enzyme solution. The reaction was initiated by addition of CoA. The reaction was performed at 28° C.

The results obtained are shown in Table 3. When compared to strains c-1 and c-2, strains MaACL1-1 and MaACL1-2 or strains MaACL2-1 and MaACL2-2 were found to have higher ACL activity, suggesting that products of the MaACL1 and MaACL2 genes had ACL activity.

TABLE 3

| | Measurement of MaACL activity | | | | | |
|---|---|---|---|---|---|---|
| Strain | c-1 | c-2 | MaACL1-1 | MaACL1-2 | MaACL2-1 | MaACL2-2 |
| ACL activity (nmol · min-1 · mg-1) | 0.80 | 0.98 | 30.96 | 20.94 | 1.15 | 1.09 |

Next, MaACL1 was studied for its dependence on $Mg^{2+}$ concentration. Namely, the above ACL reaction solution was modified to have a $MgCl_2$ concentration of 5 mM, 10 mM, 20 mM or 40 mM, and the activity was measured in the same manner. FIG. 6 shows the relative activity, assuming that the activity at a $MgCl_2$ concentration of 10 mM was set to 1.

As shown in FIG. 6, ACL1 showed the maximum activity at an ATP:citrate:$Mg^{2+}$ ratio of about 1:1:1.

Example 5

(1) Construction of *Mortierella* Genomic Library

*M. alpina* strain 1S-4 was inoculated into 100 ml liquid medium (1% glucose, 0.5% yeast extract, pH 6.0) and cultured with shaking at 28° C. for 4 days. The cells were collected by filtration with a filter and treated by the CTAB method to extract genomic DNA.

The resulting genomic DNA (about 200 µg) was partially digested with a restriction enzyme Sau3AI, such that cleaved DNAs had a distribution whose center was located at around 20 kb. The resulting DNA fragments were subjected to 10% to 40% sucrose density gradient centrifugation (rotor SW28 (Beckman), 25,000 rpm, 10° C., 24 hours) and fractionated into 1 ml aliquots using an AUTOMATIC LIQUID CHARGER (ADVANTEC) and a MICRO TUBE PUMP (EYELA). A fraction having a distribution whose center was located at around 20 kbp was purified. The thus obtained genomic DNA fragments were treated with a λBlueSTAR/BamHI vector kit (NOVAGEN) to prepare a genomic library.

(2) Cloning of URA5 Genomic DNA

To use the *Mortierella* URA5 gene as a marker gene, its genomic DNA including promoter and terminator regions was cloned as follows. Namely, a probe was prepared based on the cDNA sequence of the *Mortierella* URA5 gene (Biosci Biotechnol Biochem., 68, pp. 277-285 (2004)) and used for screening from the *Mortierella* genomic library to identify a nucleotide sequence of approximately 2.1 kbp covering this gene (SEQ ID NO: 13).

(3) Cloning of GAPDH Homolog Genomic DNA

To constitutively and highly express a transgene in *Mortierella* cells, a homolog of the glyceraldehyde-3-phosphate dehydrogenase (GAPDH) gene, which is known to be constitutively and highly expressed in many organisms, was cloned. Based on the GAPDH homolog sequence (SEQ ID NO: 14) found among the ESTs obtained in Example 1, primers ATGACCATCAAGATCGGCATCA (SEQ ID NO: 24) and TTAAGCATGATCCTTCTTGGCC (SEQ ID NO: 25) were prepared. These primers were used to prepare a probe in the same manner as shown in Example 2 by using the *Mortierella* cDNA as a template, followed by screening from the genomic library to identify a nucleotide sequence of approximately 3 kbp covering the GAPDH homolog (SEQ ID NO: 15).

Example 6

Construction of *Mortierella* Expression Vectors

A 0.9 kb region upstream of the *M. alpina* GAPDH structural gene was amplified by PCR with primers:

```
AAGCTTGATCACGTCGGGTGATGAGT    (SEQ ID NO: 26)
TGCTGTTGAC;
and

GAATTCGATGTTGAATGTGTGGTGTG    (SEQ ID NO: 27)
``` and a 0.5 kb region downstream of the *M. alpina* GAPDH structural gene was amplified by PCR with primers:

```
TCTAGATAAGAAAAGGGAGTGAATCG;   (SEQ ID NO: 28)
and

GCGGCCGCGATCCATGCACGGGTCCTTC  (SEQ ID NO: 29)
``` to clone the GAPDH promoter (SEQ ID NO: 16) and the GAPDH terminator (SEQ ID NO: 17). These were digested at the restriction enzyme sites added on the primers, i.e., at the HindIII and EcoRI sites and at the XbaI and NotI sites, respectively, and then inserted into the HindIII/EcoRI site and the XbaI/NotI site on pBluescriptII SK− (Stratagene), respectively. This plasmid was further blunt-ended at the ApaI site, into which 18SrDNA (0.9 kb) which had been prepared from plasmid pD4 (Appl Environ Microbiol., 66, pp. 4655-4661 (2000)) by digestion with XbaI and HindIII and the subsequent blunt ending was then integrated to prepare plasmid pBGptR. A SalI-digested fragment (2.1 kb) prepared from the genomic DNA of the *M. alpina* Ura5 gene including the promoter and terminator was inserted into the XhoI site of pBGptR to prepare vector pH001. Further, for insertion of a multicloning site, which is to facilitate introduction of a useful gene for production of PUFA, between GAPDH promoter and terminator, pH001 was digested at the HindIII site 5′-terminal to the GAPDH promoter and at the NotI site 3′-terminal to the GAPDH terminator with the corresponding restriction enzymes and then blunt-ended, followed by self-ligation to destroy the HindIII and NotI sites in two steps, thereby constructing vector pH002. Oligonucleotides for multicloning site preparation:

```
SC/MCS-F2:
                              (SEQ ID NO: 30)
5'-ctagcgcggccgcctcgagaagcttcccggggcatgcctgcagt
ctagag;
and SC/MCS-R2:
                              (SEQ ID NO: 31)
5'-aattctctagactgcaggcatgccccgggaagcttctcgaggcg
gccgcg
``` were complementarily annealed to each other to give an EcoRI/NheI overhang, which was then inserted into the EcoRI/XbaI site of pH002 to construct vector pH003. In vector pH003, EcoRI/XbaI/PstI/SphI/SmaI/HindIII/XbaI/NotI was available for use as a multicloning site. Next, two sites for an octanucleotide-recognizing restriction enzyme AscI were introduced outside the EcoRI and HindIII sites of pUC19 to construct vector pUCAA from which an insert can be excised in its entirety by AscI digestion. This pUCAA was digested with EcoRI/HindIII and then blunt-ended, into which a blunt-ended insert (4.4 kb) obtained from pH003 by partial digestion with BssHII was then inserted to prepare vector pH004. pH004 was partially digested with EcoRI and then blunt-ended and further ligated to destroy the EcoRI site adjacent to BssHII, thereby constructing pDuraSC which serves as a basic vector for self-cloning.

To highly express MaACL1 and MaACL2 in *Mortierella* cells, *Mortierella* expression vectors were constructed as follows. The plasmid pUC-ACL1 was digested with restriction enzymes XbaI and HindIII to give a DNA fragment of approximately 3.5 kbp. This DNA fragment was inserted into the XbaI-SalI site of the vector pDuraSC to construct plasmid pDuraSC-ACL1. On the other hand, the vector pDuraSC was digested with a restriction enzyme EcoRI, blunt-ended with a Blunting Kit and then digested with XhoI, while the plasmid pB-ACL2 was digested with a restriction enzyme NotI, blunt-ended with a Blunting Kit and then partially digested with XhoI to give a fragment of approximately 3.5 kbp. The resulting fragments were ligated to each other to construct plasmid pDuraSC-ACL2.

Example 7

Transformation of Mortierella

Uracil-auxotrophic strain Δura-3 derived from *M. alpina* as described in a patent document (WO2005/019437 entitled "Method of Breeding Lipid-Producing Fungus") was used as a host and transformed with the plasmid pDuraSC-ACL1 or pDuraSC-ACL2 by the particle delivery method. For screening of the transformed strains, SC agar medium was used (0.5% Yeast Nitrogen Base w/o Amino Acids and Ammonium Sulfate (Difco), 0.17% ammonium sulfate, 2% glucose, 0.002% adenine, 0.003% tyrosine, 0.0001% methionine, 0.0002% arginine, 0.0002% histidine, 0.0004% lysine, 0.0004% tryptophan, 0.0005% threonine, 0.0006% isoleucine, 0.0006% leucine, 0.0006% phenylalanine, and 2% agar).

Example 8

Evaluation of Mortierella Transformants (1) Transformed Strains Obtained with Plasmid pDuraSC-ACL1

The resulting transformed strains were each inoculated into 4 ml GY medium (2% glucose, 1% yeast extract) and cultured with shaking at 28° C. for 3 or 4 days. The cells were collected by filtration, and RNA was extracted with an RNeasy plant kit (QIAGEN). A SuperScript First-Strand system for RT-PCR (Invitrogen) was used to synthesize cDNA, followed by RT-PCR with primers GCGTCATCCCCACCACT-GTT (SEQ ID NO: 32) and GCTGGCGGGAGGAGTGC-CAGCACG (SEQ ID NO: 33).

Figure 7:
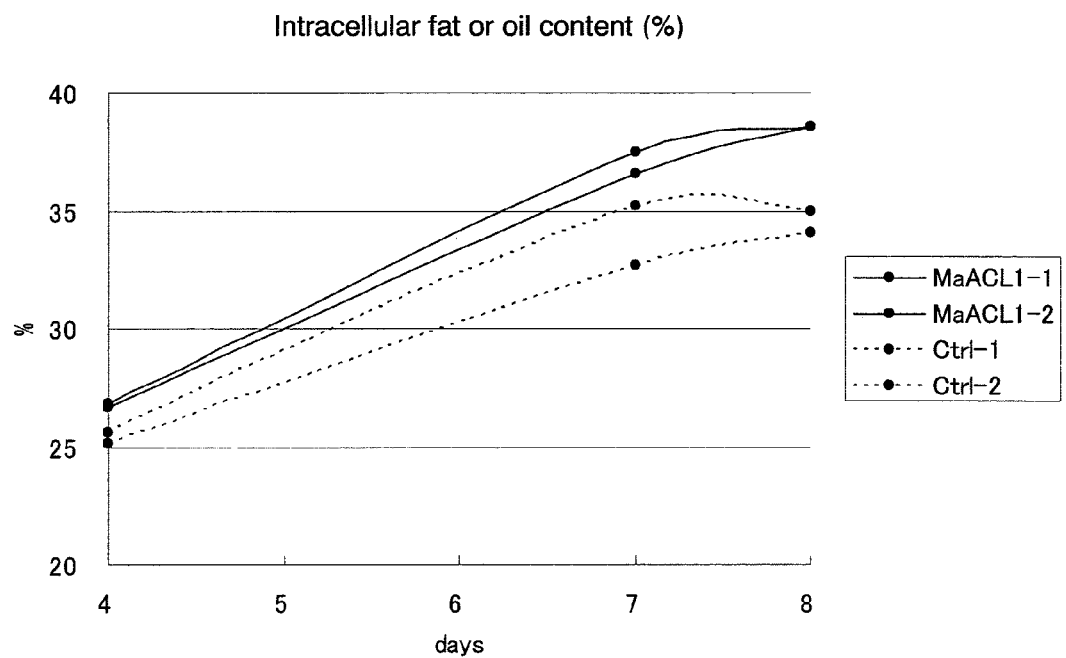
FIG. 7 shows the time course of the intracellular fat or oil content compared between MaACL1 transformants (MaACL1-1, -2) and non-transformants (Ctrl-1, -2) in culture.

As a result, among the individual transformed strains, those with high ACL1 expression levels were selected. These strains were each inoculated into a liquid medium (2% glucose, 1% yeast extract) and cultured with shaking at 28° C. On day 3 of culture, a 20% glucose solution was added to the culture solution in a volume of 1/20. On days 4, 6, 7 and 8 of culture, a portion of the cells were collected and freeze-dried. Fatty acids in the cells were derived into corresponding methyl esters and then extracted with hexane. After distilling off hexane, the fatty acids were analyzed by gas chromatography to quantify the content of fatty acids per cell. The results obtained are shown in FIG. 7.

As shown above, the *Mortierella* strains transformed to highly express the MaACL1 gene allowed an increase in the intracellular fat or oil content at the late stage of culture when compared to the wild-type strains.

(2) Transformed Strains Obtained with Plasmid pDuraSC-ACL2

The resulting transformed strains were each subcultured on SC agar medium to select 9 strains showing good growth. Further, the above selected strains were each inoculated into 4 ml GY medium (2% glucose, 1% yeast extract) and cultured with shaking at 28° C. for 4 days. The cells were collected by filtration and freeze-dried. A portion (about 10-20 mg) of the dried cells was treated by the hydrochloric acid/methanol method to derive fatty acids in the cells into corresponding methyl esters, followed by extraction with hexane. After distilling off hexane, the fatty acids were analyzed by gas chromatography. As a result, strains having a higher intracellular content of fatty acids and a higher ratio of arachidonic acid in total fatty acids were selected and designated as MaACL2#1 and MaACL2#2, respectively.

These strains were each inoculated into 4 ml GY medium and cultured with shaking at 28° C. for 4 days. The cells were collected by filtration, and RNA was extracted with an RNeasy plant kit (QIAGEN). A SuperScript First-Strand system for RT-PCR (Invitrogen) was used to synthesize cDNA. To confirm the expression of each gene from the introduced construct, the above cDNA was used as a template to perform PCR with ExTaq (Takara Bio Inc., Japan) in 25 cycles of 94° C. for 30 seconds, 55° C. for 30 seconds, and 72° C. for 1 minute by using a combination of the following primers:

Primer MaGAPDHpfw: CACACCACACATTCAACATC (SEQ ID NO: 34); and

Primer ACL2-R5: CGAAGCCGGCAAAGGCG-GCAGTCG (SEQ ID NO: 35). As a result, these strains were confirmed to express the MaACL2 gene from the introduced construct.

Moreover, these two strains and strain 1S-4 were each inoculated into 4 ml GY medium (n=3) and cultured with shaking at 28° C. at 125 rpm. On day 3 of culture, 20% glucose (200 μl) was added, and culture was further continued until day 6. On day 6, all cells were collected by filtration and freeze-dried. A portion (about 10-20 mg) of the dried cells was treated by the hydrochloric acid/methanol method to derive fatty acids in the cells into corresponding methyl esters, followed by extraction with hexane. After distilling off hexane, the fatty acids were analyzed by gas chromatography. The intracellular fatty acid content and the arachidonic acid production per medium are summarized in Tables 4 and 5, respectively.

TABLE 4

| Intracellular fatty acid content (%) | | |
|---|---|---|
| MaACL2#1 | MaACL2#2 | 1S-4 |
| 35.09 ± 3.27 | 35.95 ± 2.99 | 33.67 ± 2.61 |

TABLE 5

| Arachidonic acid production per medium (g/L) | | |
|---|---|---|
| MaACL2#1 | MaACL2#2 | 1S-4 |
| 2.00 ± 0.43 | 2.35 ± 0.25 | 1.89 ± 0.12 |

As shown above, the *Mortierella* strains transformed to highly express the MaACL2 gene allowed an increase in both intracellular fatty acid content and arachidonic acid production per medium when compared to the wild-type strain.

INDUSTRIAL APPLICABILITY

The ACL genes of the present invention allow an improvement in the ability to produce fatty acids and/or lipids, and hence are preferred as a mans for improving the productivity of polyunsaturated fatty acids in microorganisms and plants. As a result, the ACL genes of the present invention enable the provision of effective fatty acids or lipids at a lower cost than in conventional cases, and are useful as being applicable to foods, cosmetics, pharmaceuticals, soaps, etc.

SEQUENCE LISTING FREE TEXT

SEQ ID NO: 18: primer
SEQ ID NO: 19: primer

SEQ ID NO: 20: primer
SEQ ID NO: 21: primer
SEQ ID NO: 22: primer
SEQ ID NO: 23: primer
SEQ ID NO: 24: primer
SEQ ID NO: 25: primer
SEQ ID NO: 26: primer
SEQ ID NO: 27: primer SEQ ID NO: 28: primer
SEQ ID NO: 29: primer
SEQ ID NO: 30: primer
SEQ ID NO: 31: primer
SEQ ID NO: 32: primer
SEQ ID NO: 33: primer
SEQ ID NO: 34: primer
SEQ ID NO: 35: primer

The invention claimed is:

1. An isolated nucleic acid comprising any one of (a) to (f) below:
   (a) a nucleotide sequence encoding SEQ ID NO: 11 or SEQ ID NO: 12;
   (b) a nucleotide sequence encoding a protein comprising SEQ ID NO: 11 or SEQ ID NO: 12 except that 1 to 30 amino acids have been deleted, substituted, or added, and having ATP:citrate lyase activity;
   (c) a nucleotide sequence which is hybridizable under hybridization conditions comprising 2×SSC at 50° C. with the nucleotide sequence complementary to SEQ ID NO: 9 or SEQ ID NO: 10 and which encodes a protein having ATP:citrate lyase activity;
   (d) a nucleotide sequence sharing an identity of 75% or more with SEQ ID NO: 9 or SEQ ID NO: 10 and encoding a protein having ATP:citrate lyase activity;
   (e) a nucleotide sequence which encodes an amino acid sequence sharing an identity of 75% or more with SEQ ID NO: 11 or SEQ ID NO: 12 and having ATP:citrate lyase activity; or
   (f) a nucleotide sequence which is hybridizable under hybridization conditions comprising 2×SSC at 50° C. with the nucleotide sequence complementary to a nucleotide sequence encoding a protein comprising SEQ ID NO: 11 or 12 and having ATP:citrate lyase activity.

2. The isolated nucleic acid according to claim 1, which comprises any one of (a) to (c) below:
   (a) a nucleotide sequence encoding a protein comprising SEQ ID NO: 11 or SEQ ID NO: 12 except that 1 to 10 amino acids have been deleted, substituted, or added, and having ATP:citrate lyase activity;
   (b) a nucleotide sequence which is hybridizable under hybridization conditions of 0.2×SSC at 63° C. with the nucleotide sequence complementary to SEQ ID NO: 9 or SEQ ID NO: 10 and which encodes a protein having ATP:citrate lyase activity; or
   (c) a nucleotide sequence which encodes an amino acid sequence sharing an identity of 90% or more with SEQ ID NO: 11 or SEQ ID NO: 12 and which encodes a protein having ATP:citrate lyase activity.

3. An isolated nucleic acid comprising any one of (a) to (c) below:
   (a) the nucleotide sequence of SEQ ID NO: 9 or SEQ ID NO: 10;
   (b) a nucleotide sequence encoding a protein comprising SEQ ID NO: 11 or SEQ ID NO: 12; or
   (c) the nucleotide sequence shown in of SEQ ID NO: 5 or SEQ ID NO: 6.

4. A recombinant vector comprising the nucleic acid according to claim 1.

5. A transformant carrying the nucleic acid according to claim 1.

6. A transformant transformed with the recombinant vector according to claim 4.

7. A transformant transformed with the recombinant vector according to claim 4, whose ability to produce fatty acids is improved by introduction of the vector according to claim 4.

8. The transformant according to claim 5, wherein the transformant is a lipid-producing fungus.

9. The transformant according to claim 8, wherein the lipid-producing fungus is *Mortierella alpina*.

10. A method for preparing a fatty acid or lipid, which comprises collecting a fatty acid or lipid from a cultured product obtained by culturing the transformant according to claim 5.

* * * * *

SEQUENCE LISTING

<160> NUMBER OF SEQ ID NOS: 41

<210> SEQ ID NO 1
<211> LENGTH: 1069
<212> TYPE: DNA
<213> ORGANISM: Mortierella alpina

<400> SEQUENCE: 1

```
tccagacctt ggtcaagaac ggaaccatcc agctcaagcc cgagcccgag actcccaaga      60
tccccatcga ttactcctgg gcccaggagc tcggacttgt ccgtaagcct gcctcgttcg     120
tgtcgaccat ttgcgatgac cgtggtcagg agttgctcta tgccggtatg cgtatctcgg     180
acgtcttcaa ggaggacatt ggtatcggag gtgttctgtc cttgctctgg ttcaagcgcc     240
gtctgcccga ctacgcctgc aagtttatcg agatggttct catgctcact gctgatcacg     300
gtcccgccgt ctcaggtgca cacaacacca tcgtcactgc ccgtgccggc aaggatttgg     360
tttcgtcgtt gtgcgcaggt cttttgacga ttggtgaccg cttcggaggt gccttggatg     420
gtgccgccga gcagttctcg tctgcatacg acaagtcgct cacgccccgt gagtttgtct     480
ctgtgatgcg taagcagaac aagttgattc tcggtatcgg ccacaagatc aagtcgcgca     540
cgaaccccga tctgcgtgtc gagatcatca aggagtacgc caagaagcac ttcccctcga     600
cccctgttct ggactatgcc cttcaggtgg agaacatcac gacgtccaag aaggacaact     660
tgatcttgaa cgtcgatgga gcgatcggaa tcttgtttgt ggatctgttg agaaactcgg     720
gcgcgttcac gcgtgaggag gctgaggagt acatcaagat tggaacgttg aacggtctgt     780
ttgtattggg tcgctcgatc ggattcattg gacattactt ggaccagaag aggctgaagc     840
agggcttgta cagacatcct tgggatgata tctcgtacct gaccccggc aatgagctcg     900
gacggacggt tgcctcgctg gattcgatca acaagaaggc ctaaagaggg gacgttggag     960
aaactgaacg aacttagaga agaaaaaaca acactcatc atctatcgtt gtacatatta    1020
aatattaaat aactttgtga gcccaaaaaa aaaaaaaaa aaaaaaaaa                 1069
```

<210> SEQ ID NO 2
<211> LENGTH: 470
<212> TYPE: DNA
<213> ORGANISM: Mortierella alpina

<400> SEQUENCE: 2

```
ttgataccgt cgtcaacttt gcctcgtgcc gctctgttta ccagtccacg gttgatatcc      60
tcagtcactc tgaccagatc aagacgatct cgatcattgc cgagggtgtc cccgagcgtc     120
gtgctcgcca gatcctctgg gaggccaagg ccaagaacgt gctcgtgatc ggaccagcca     180
ctgtcggagg catcaagccc ggctgcttca agatcggaaa cactggaggt atgatggaca     240
acattgtctc gtccaagttg taccgcgccg gttctgttgc ctacgtctcc aagtctggcg     300
gtatgtccaa cgagctgaac aacatcatct cgcgcaccac tgacggtgtc tacgagggag     360
tcgccatcgg aggagaccgt taccctggat cgaccttcat cgaccacttg cttcgctatg     420
```

```
agcgggaccc caactgcaag atgttggtct tgctcggaga ggtcggaggt            470
```

<210> SEQ ID NO 3
<211> LENGTH: 603
<212> TYPE: DNA
<213> ORGANISM: Mortierella alpina

<400> SEQUENCE: 3

```
ccaagatgtt tgcaccgagg tccagtttgg acatgctggt gcccttgccc agtcagatct   60
tgagacagct gatgccaaga accgtgccct tcgtgccgct ggcgtgatcg tcccagagac  120
gtttgaaatg ctccccttgg ttttgagtca gacctaccag gctctcgtca agaagggcgt  180
cgtcattgtc cgctctgagc ccagacacc caagatccct attgactact cctgggccca  240
ggagttgggt cttgtccgca agccagcctc gtttgtgtcg actatttgtg atgaccgtgg  300
ccaggaactg ctctatgctg gcatgcgcat ctcggatgtg ttcaaggagg acatcggtat  360
cggtggtgtt ctctccctgc tctggttcaa gcgccgtctc cccgactatg cctgcaagtt  420
tatcgagatg gtcctcatgc tcacagctga tcatggtcct gctgtttcgg gtgctcataa  480
cacgattgtg accgctcgtg caggccagga tcttgtttcg tctctgtgcg cgggtctgtt  540
gacgattgga gaccgtcttg gaggcgcctt ggaccgaccc gctgagcact tctcgtctgc  600
ata                                                                603
```

<210> SEQ ID NO 4
<211> LENGTH: 474
<212> TYPE: DNA
<213> ORGANISM: Mortierella alpina
<220> FEATURE:
<221> NAME/KEY: modified_base
<222> LOCATION: (386)..(386)
<223> OTHER INFORMATION: a, c, t, g, unknown or other
<220> FEATURE:
<221> NAME/KEY: modified_base
<222> LOCATION: (389)..(389)
<223> OTHER INFORMATION: a, c, t, g, unknown or other

<400> SEQUENCE: 4

```
ccgaggttga caccgtggtg aactttgcct cttgccgttc cgtttatgac tcgacccgcg   60
agattttcaa gcactcgaag caaatccgca ccatctccat catcgccgag ggtgtgccag  120
agcgccgcgc tcgtcaaatt ttgtgggagg ccaaagagcg taatgtcttg gtcattggac  180
ctgccactgt cggaggcatc aagcccggct gcttcaagat tggaaacact ggaggaatga  240
tggataatac tgtatcctca aagctctacc gcgcaggatc cgtggcttat gtgtccaagt  300
ctggaggcat gtccaacgag ttgaacaaca ttatctctcg caccaccgat ggtgtctacg  360
agggagttgc cattggaggg accgntanc ctggttcgac ttttactgac cacttgcttc   420
gctacgagaa ggatccgggt gcaagatgct tgtcttgtcg ggcgaggtcg gagg         474
```

<210> SEQ ID NO 5
<211> LENGTH: 3840
<212> TYPE: DNA
<213> ORGANISM: Mortierella alpina
<220> FEATURE:
<221> NAME/KEY: CDS
<222> LOCATION: (178)..(3714)

<400> SEQUENCE: 5

```
ttgcctgtcc ctcctggcgc cccttctctc actactcact agactcgtcc tcctcctcta   60
cattgtatac ctagccttct cttcctacgg tctccttccg ctcctggtgc tttctatact  120
```

```
catcctcttt gcatagcatt ttctcccctt ctataatata catacacaca caacaag                    177 atg tct gct aaa gcc gtt cgc gaa tac gat gga aag ctg ctc ttg gcc                   225
Met Ser Ala Lys Ala Val Arg Glu Tyr Asp Gly Lys Leu Leu Leu Ala
1               5                   10                  15 cac tgg ctt cac cgt gtt gcc gtg ccc gaa tca gag acc gca gga tca                   273
His Trp Leu His Arg Val Ala Val Pro Glu Ser Glu Thr Ala Gly Ser
            20                  25                  30 gca aca acg gga tcc aag ttc gtc cag ccc acc acc cgc ctt gcc cac                   321
Ala Thr Thr Gly Ser Lys Phe Val Gln Pro Thr Thr Arg Leu Ala His
        35                  40                  45 atc tcc atc gac acc tcg ctc ttg cag gac aag acc cag ttc gat cag                   369
Ile Ser Ile Asp Thr Ser Leu Leu Gln Asp Lys Thr Gln Phe Asp Gln
50                  55                  60 cac gtc cgc tcg acc ttg gat cag ctc gag gtc tcg cac cct tgg ctg                   417
His Val Arg Ser Thr Leu Asp Gln Leu Glu Val Ser His Pro Trp Leu
65                  70                  75                  80 ttg acc aac aag ctg gtc gcc aag cct gac cag ttg atc aag cgt cgt                   465
Leu Thr Asn Lys Leu Val Ala Lys Pro Asp Gln Leu Ile Lys Arg Arg
                85                  90                  95 gga aag agc ggc ttg ctg ctc ttg aac gcc gaa tgg gct gag gct aga                   513
Gly Lys Ser Gly Leu Leu Leu Leu Asn Ala Glu Trp Ala Glu Ala Arg
            100                 105                 110 gcc tgg atc gag aag cac gcg gcc aag gac gtc ctt gtg gac tcg gtt                   561
Ala Trp Ile Glu Lys His Ala Ala Lys Asp Val Leu Val Asp Ser Val
        115                 120                 125 ccc ggt gtt ctc aag acc ttc ctc gtc gag ccc ttc att ccc cac cct                   609
Pro Gly Val Leu Lys Thr Phe Leu Val Glu Pro Phe Ile Pro His Pro
130                 135                 140 tct aac act gag tac tac atc tgc atc aac tca gat cgt gat ggt gac                   657
Ser Asn Thr Glu Tyr Tyr Ile Cys Ile Asn Ser Asp Arg Asp Gly Asp
145                 150                 155                 160 aac atc ctc ttc acg cac gag gga ggt atc gag gtc gga gat gtt gat                   705
Asn Ile Leu Phe Thr His Glu Gly Gly Ile Glu Val Gly Asp Val Asp
                165                 170                 175 gcc aag gca ttg aag ctc cag gtg aag gtt cag gac gcc ttc ccc acc                   753
Ala Lys Ala Leu Lys Leu Gln Val Lys Val Gln Asp Ala Phe Pro Thr
            180                 185                 190 gca gag gcc att cgc tcg gct ctc ctg gtc cat gtc cct gag gcc aag                   801
Ala Glu Ala Ile Arg Ser Ala Leu Leu Val His Val Pro Glu Ala Lys
        195                 200                 205 cac gat gtt ctt gtt gac ttt atc act cgc ctc tat gct gtt tac atc                   849
His Asp Val Leu Val Asp Phe Ile Thr Arg Leu Tyr Ala Val Tyr Ile
210                 215                 220 gac ctc cac ttc acc tac ctt gag atc aac ccc ttg gtc gtc ttg gat                   897
Asp Leu His Phe Thr Tyr Leu Glu Ile Asn Pro Leu Val Val Leu Asp
225                 230                 235                 240 ccc aca gag gac gag cct gct cgt gtc tac tac ctc gac ctg gct gct                   945
Pro Thr Glu Asp Glu Pro Ala Arg Val Tyr Tyr Leu Asp Leu Ala Ala
                245                 250                 255 aag ctc gat cag act gca gag ttc gag gct ggt ccc aag tgg gcc atc                   993
Lys Leu Asp Gln Thr Ala Glu Phe Glu Ala Gly Pro Lys Trp Ala Ile
            260                 265                 270 gcc aga gct cct cag aac att gga att gct ggc gtc atc ccc acc act                   1041
Ala Arg Ala Pro Gln Asn Ile Gly Ile Ala Gly Val Ile Pro Thr Thr
        275                 280                 285 gtt ggc gct gat gct ggc cct ggc atg gat ttc ccc gca cct ttc ggt                   1089
Val Gly Ala Asp Ala Gly Pro Gly Met Asp Phe Pro Ala Pro Phe Gly
290                 295                 300 cgt gaa ttg acc aag gag gag gcc tat gtt cag gag ctg gac tct aag                   1137
Arg Glu Leu Thr Lys Glu Glu Ala Tyr Val Gln Glu Leu Asp Ser Lys
```

```
                    305                 310                 315                 320
acc ggt gct tcg ctc aag ctc acc atc ctg aac aag gat gga cgc atc            1185
Thr Gly Ala Ser Leu Lys Leu Thr Ile Leu Asn Lys Asp Gly Arg Ile
                325                 330                 335 tgg acc atg gtt gct gga ggc ggt gcc tct gtc gtt tac agt gat gcc            1233
Trp Thr Met Val Ala Gly Gly Gly Ala Ser Val Val Tyr Ser Asp Ala
            340                 345                 350 atc gct gcc ctt ggc cag gct gac gag ctc gcc aac tac gga gag tac            1281
Ile Ala Ala Leu Gly Gln Ala Asp Glu Leu Ala Asn Tyr Gly Glu Tyr
            355                 360                 365 tct ggt gcc ccc acc gag acc cag acc tat gaa tac gcc aag acc atc            1329
Ser Gly Ala Pro Thr Glu Thr Gln Thr Tyr Glu Tyr Ala Lys Thr Ile
        370                 375                 380 ctt gac ctt atg acc cgc tct gcc acc cct cac ccc gag ggc aag gtc            1377
Leu Asp Leu Met Thr Arg Ser Ala Thr Pro His Pro Glu Gly Lys Val
385                 390                 395                 400 ctg atc att gga gga ggt atc gcc aac ttc act aac gtc gcc tcg acc            1425
Leu Ile Ile Gly Gly Gly Ile Ala Asn Phe Thr Asn Val Ala Ser Thr
                405                 410                 415 ttc aag gga att gtc cgc gct ctt acc gag ttt aaa cag ccc ttg atc            1473
Phe Lys Gly Ile Val Arg Ala Leu Thr Glu Phe Lys Gln Pro Leu Ile
            420                 425                 430 gcc cac aag gtc cgc atc ttt gtc cgt cgt ggt ggt ccc aac tac cag            1521
Ala His Lys Val Arg Ile Phe Val Arg Arg Gly Gly Pro Asn Tyr Gln
            435                 440                 445 gag ggt ctt cgc tcc atg cgt caa ctc ggc gag tcc ttg gga gtt gag            1569
Glu Gly Leu Arg Ser Met Arg Gln Leu Gly Glu Ser Leu Gly Val Glu
        450                 455                 460 atc cag gtc ttt gga ccc gag acc cac atc acc gag att gtt cct ctg            1617
Ile Gln Val Phe Gly Pro Glu Thr His Ile Thr Glu Ile Val Pro Leu
465                 470                 475                 480 gcc ttg act gga cgc tct tcc gac aac ttg gct gcc acc aac gcc aac            1665
Ala Leu Thr Gly Arg Ser Ser Asp Asn Leu Ala Ala Thr Asn Ala Asn
                485                 490                 495 aac ggc agc gcc tcg tcc gga aac ctc ctt cag gat cag ctc ttg ggc            1713
Asn Gly Ser Ala Ser Ser Gly Asn Leu Leu Gln Asp Gln Leu Leu Gly
            500                 505                 510 acc aac agc aac ctc aac acc cct gtt ccc act gcc ccc gtc tcc cgt            1761
Thr Asn Ser Asn Leu Asn Thr Pro Val Pro Thr Ala Pro Val Ser Arg
            515                 520                 525 gct ggc act cct ccc gcc agc gag agg atg act tac ttc acg gac gca            1809
Ala Gly Thr Pro Pro Ala Ser Glu Arg Met Thr Tyr Phe Thr Asp Ala
        530                 535                 540 gac gca aag aag gtc ggc cac gat tcc aac gtt ccc ttc act gcc cag            1857
Asp Ala Lys Lys Val Gly His Asp Ser Asn Val Pro Phe Thr Ala Gln
545                 550                 555                 560 act cgc tcg ttc atc tac gga atg cag ccc cgt gct gtt cag gga atg            1905
Thr Arg Ser Phe Ile Tyr Gly Met Gln Pro Arg Ala Val Gln Gly Met
                565                 570                 575 ctc gac ttt gat ttc atc tgc aag cgt gag gtc ccc tcg gtc gca gcc            1953
Leu Asp Phe Asp Phe Ile Cys Lys Arg Glu Val Pro Ser Val Ala Ala
            580                 585                 590 atg atc tac ccc ttt ggc ggt gct cac gtt cag aag ttc tac tgg ggc            2001
Met Ile Tyr Pro Phe Gly Gly Ala His Val Gln Lys Phe Tyr Trp Gly
            595                 600                 605 acc aag gag act ctc ttg ccc gtt tac act act ctg gag gag gcc act            2049
Thr Lys Glu Thr Leu Leu Pro Val Tyr Thr Thr Leu Glu Glu Ala Thr
        610                 615                 620 gcc aag ttc ccc gag gtt gat acc gtc gtc aac ttt gcc tcg tgc cgc            2097
Ala Lys Phe Pro Glu Val Asp Thr Val Val Asn Phe Ala Ser Cys Arg
```

-continued

| | | | | | | | | | | | | | | | | |
|---|---|---|---|---|---|---|---|---|---|---|---|---|---|---|---|---|
| | 625 | | | | 630 | | | | 635 | | | | 640 | | | |
| tct | gtt | tac | cag | tcc | acg | gtt | gat | atc | ctc | agt | cac | tct | gac | cag | atc | 2145 |
| Ser | Val | Tyr | Gln | Ser | Thr | Val | Asp | Ile | Leu | Ser | His | Ser | Asp | Gln | Ile | |
| | | | | 645 | | | | | 650 | | | | | 655 | | |
| aag | acg | atc | tcg | atc | att | gcc | gag | ggt | gtc | ccc | gag | cgt | cgt | gct | cgc | 2193 |
| Lys | Thr | Ile | Ser | Ile | Ile | Ala | Glu | Gly | Val | Pro | Glu | Arg | Arg | Ala | Arg | |
| | | | 660 | | | | | 665 | | | | | 670 | | | |
| cag | atc | ctc | tgg | gag | gcc | aag | gcc | aag | aac | gtg | ctc | gtg | atc | gga | cca | 2241 |
| Gln | Ile | Leu | Trp | Glu | Ala | Lys | Ala | Lys | Asn | Val | Leu | Val | Ile | Gly | Pro | |
| | | | 675 | | | | | 680 | | | | | 685 | | | |
| gcc | act | gtc | gga | ggc | atc | aag | ccc | ggc | tgc | ttc | aag | atc | gga | aac | act | 2289 |
| Ala | Thr | Val | Gly | Gly | Ile | Lys | Pro | Gly | Cys | Phe | Lys | Ile | Gly | Asn | Thr | |
| | 690 | | | | | 695 | | | | | 700 | | | | | |
| gga | ggt | atg | atg | gac | aac | att | gtc | tcg | tcc | aag | ttg | tac | cgc | gcc | ggt | 2337 |
| Gly | Gly | Met | Met | Asp | Asn | Ile | Val | Ser | Ser | Lys | Leu | Tyr | Arg | Ala | Gly | |
| 705 | | | | | 710 | | | | | 715 | | | | | 720 | |
| tct | gtt | gcc | tac | gtc | tcc | aag | tct | ggc | ggt | atg | tcc | aac | gag | ctg | aac | 2385 |
| Ser | Val | Ala | Tyr | Val | Ser | Lys | Ser | Gly | Gly | Met | Ser | Asn | Glu | Leu | Asn | |
| | | | | 725 | | | | | 730 | | | | | 735 | | |
| aac | atc | atc | tcg | cgc | acc | act | gac | ggt | gtc | tac | gag | gga | gtc | gcc | atc | 2433 |
| Asn | Ile | Ile | Ser | Arg | Thr | Thr | Asp | Gly | Val | Tyr | Glu | Gly | Val | Ala | Ile | |
| | | | 740 | | | | | 745 | | | | | 750 | | | |
| gga | gga | gac | cgt | tac | cct | gga | tcg | acc | ttc | atc | gac | cac | ttg | ctt | cgc | 2481 |
| Gly | Gly | Asp | Arg | Tyr | Pro | Gly | Ser | Thr | Phe | Ile | Asp | His | Leu | Leu | Arg | |
| | | 755 | | | | | 760 | | | | | 765 | | | | |
| tat | gag | cgg | gac | ccc | aac | tgc | aag | atg | ttg | gtc | ttg | ctc | gga | gag | gtc | 2529 |
| Tyr | Glu | Arg | Asp | Pro | Asn | Cys | Lys | Met | Leu | Val | Leu | Leu | Gly | Glu | Val | |
| | 770 | | | | | 775 | | | | | 780 | | | | | |
| gga | ggt | gtc | gag | gag | tac | aag | gtc | tgt | gag | gcg | atc | aag | aac | ggg | acc | 2577 |
| Gly | Gly | Val | Glu | Glu | Tyr | Lys | Val | Cys | Glu | Ala | Ile | Lys | Asn | Gly | Thr | |
| 785 | | | | | 790 | | | | | 795 | | | | | 800 | |
| atc | cgc | aag | ccc | gtg | att | gcc | tgg | tgc | atc | ggt | acc | tgc | gcc | aag | atg | 2625 |
| Ile | Arg | Lys | Pro | Val | Ile | Ala | Trp | Cys | Ile | Gly | Thr | Cys | Ala | Lys | Met | |
| | | | | 805 | | | | | 810 | | | | | 815 | | |
| ttt | gcc | acc | gag | gtc | cag | ttc | gga | cac | gcc | ggt | gcc | ttg | gcc | cag | tcc | 2673 |
| Phe | Ala | Thr | Glu | Val | Gln | Phe | Gly | His | Ala | Gly | Ala | Leu | Ala | Gln | Ser | |
| | | | 820 | | | | | 825 | | | | | 830 | | | |
| gat | ctc | gag | act | gcc | gat | gcc | aag | aac | aag | gct | ctc | cgc | gcc | gct | ggt | 2721 |
| Asp | Leu | Glu | Thr | Ala | Asp | Ala | Lys | Asn | Lys | Ala | Leu | Arg | Ala | Ala | Gly | |
| | | 835 | | | | | 840 | | | | | 845 | | | | |
| gtg | gtc | gtt | ccc | gag | acc | ttt | gag | aag | ttg | ccc | ttg | gtc | ttg | agc | cag | 2769 |
| Val | Val | Val | Pro | Glu | Thr | Phe | Glu | Lys | Leu | Pro | Leu | Val | Leu | Ser | Gln | |
| | 850 | | | | | 855 | | | | | 860 | | | | | |
| acc | ttc | cag | acc | ttg | gtc | aag | aac | gga | acc | atc | cag | ctc | aag | ccc | gag | 2817 |
| Thr | Phe | Gln | Thr | Leu | Val | Lys | Asn | Gly | Thr | Ile | Gln | Leu | Lys | Pro | Glu | |
| 865 | | | | | 870 | | | | | 875 | | | | | 880 | |
| ccc | gag | act | ccc | aag | atc | ccc | atc | gat | tac | tcc | tgg | gcc | cag | gag | ctc | 2865 |
| Pro | Glu | Thr | Pro | Lys | Ile | Pro | Ile | Asp | Tyr | Ser | Trp | Ala | Gln | Glu | Leu | |
| | | | | 885 | | | | | 890 | | | | | 895 | | |
| gga | ctt | gtc | cgt | aag | cct | gcc | tcg | ttc | gtg | tcg | acc | att | tgc | gat | gac | 2913 |
| Gly | Leu | Val | Arg | Lys | Pro | Ala | Ser | Phe | Val | Ser | Thr | Ile | Cys | Asp | Asp | |
| | | | 900 | | | | | 905 | | | | | 910 | | | |
| cgt | ggt | cag | gag | ttg | ctc | tat | gcc | ggt | atg | cgt | atc | tcg | gac | gtc | ttc | 2961 |
| Arg | Gly | Gln | Glu | Leu | Leu | Tyr | Ala | Gly | Met | Arg | Ile | Ser | Asp | Val | Phe | |
| | | 915 | | | | | 920 | | | | | 925 | | | | |
| aag | gag | gac | att | ggt | atc | gga | ggt | gtt | ctg | tcc | ttg | ctc | tgg | ttc | aag | 3009 |
| Lys | Glu | Asp | Ile | Gly | Ile | Gly | Gly | Val | Leu | Ser | Leu | Leu | Trp | Phe | Lys | |
| | 930 | | | | | 935 | | | | | 940 | | | | | |
| cgc | cgt | ctg | ccc | gac | tac | gcc | tgc | aag | ttt | atc | gag | atg | gtt | ctc | atg | 3057 |
| Arg | Arg | Leu | Pro | Asp | Tyr | Ala | Cys | Lys | Phe | Ile | Glu | Met | Val | Leu | Met | |

```
                 945           950            955              960
ctc act gct gat cac ggt ccc gcc gtc tca ggt gca cac aac acc atc    3105
Leu Thr Ala Asp His Gly Pro Ala Val Ser Gly Ala His Asn Thr Ile
                 965                 970                 975 gtc act gcc cgt gcc ggc aag gat ttg gtt tcg tcg ttg tgc gca ggt    3153
Val Thr Ala Arg Ala Gly Lys Asp Leu Val Ser Ser Leu Cys Ala Gly
                 980                 985                 990 ctt ttg acg att ggt gac cgc ttc gga ggt gcc ttg gat ggt gcc gcc   3201
Leu Leu Thr Ile Gly Asp Arg Phe Gly Gly Ala Leu Asp Gly Ala Ala
                 995                 1000                1005 gag cag ttc tcg tct gca tac gac aag tcg ctc acg ccc cgt gag       3246
Glu Gln Phe Ser Ser Ala Tyr Asp Lys Ser Leu Thr Pro Arg Glu
        1010                1015                1020 ttt gtc tct gtg atg cgt aag cag aac aag ttg att ctc ggt atc       3291
Phe Val Ser Val Met Arg Lys Gln Asn Lys Leu Ile Leu Gly Ile
        1025                1030                1035 ggc cac aag atc aag tcg cgc acg aac ccc gat ctg cgt gtc gag       3336
Gly His Lys Ile Lys Ser Arg Thr Asn Pro Asp Leu Arg Val Glu
        1040                1045                1050 atc atc aag gag tac gcc aag aag cac ttc ccc tcg acc cct gtt       3381
Ile Ile Lys Glu Tyr Ala Lys Lys His Phe Pro Ser Thr Pro Val
        1055                1060                1065 ctg gac tat gcc ctt cag gtg gag aac atc acg acg tcc aag aag       3426
Leu Asp Tyr Ala Leu Gln Val Glu Asn Ile Thr Thr Ser Lys Lys
        1070                1075                1080 gac aac ttg atc ttg aac gtc gat gga gcg atc gga atc ttg ttt       3471
Asp Asn Leu Ile Leu Asn Val Asp Gly Ala Ile Gly Ile Leu Phe
        1085                1090                1095 gtg gat ctg ttg aga aac tcg ggc gcg ttc acg cgt gag gag gct       3516
Val Asp Leu Leu Arg Asn Ser Gly Ala Phe Thr Arg Glu Glu Ala
        1100                1105                1110 gag gag tac atc aag att gga acg ttg aac ggt ctg ttt gta ttg       3561
Glu Glu Tyr Ile Lys Ile Gly Thr Leu Asn Gly Leu Phe Val Leu
        1115                1120                1125 ggt cgc tcg atc gga ttc att gga cat tac ttg gac cag aag agg       3606
Gly Arg Ser Ile Gly Phe Ile Gly His Tyr Leu Asp Gln Lys Arg
        1130                1135                1140 ctg aag cag ggc ttg tac aga cat cct tgg gat gat atc tcg tac       3651
Leu Lys Gln Gly Leu Tyr Arg His Pro Trp Asp Asp Ile Ser Tyr
        1145                1150                1155 ctg acc ccc ggc aat gag ctc gga cgg acg gtt gcc tcg ctg gat       3696
Leu Thr Pro Gly Asn Glu Leu Gly Arg Thr Val Ala Ser Leu Asp
        1160                1165                1170 tcg atc aac aag aag gcc taaagagggg acgttggaga aactgaacga          3744
Ser Ile Asn Lys Lys Ala
        1175 acttagagaa gaaaaacaa acactcatca tctatcgttg tacatattaa atattaaata  3804 actttgtgaa gcccaaaaaa aaaaaaaaaa aaaaaa                           3840

<210> SEQ ID NO 6
<211> LENGTH: 3686
<212> TYPE: DNA
<213> ORGANISM: Mortierella alpina
<220> FEATURE:
<221> NAME/KEY: CDS
<222> LOCATION: (21)..(3542)

<400> SEQUENCE: 6
ctgcaggctc gcccttcacc atg tct gcc aaa gct gtt cgt gag tat gat gga   53
                      Met Ser Ala Lys Ala Val Arg Glu Tyr Asp Gly
                        1               5                  10
```

```
aag ctg ctg ttg gca cac tgg ctc ctg cgc acg cct atc cct gcc acc    101
Lys Leu Leu Leu Ala His Trp Leu Leu Arg Thr Pro Ile Pro Ala Thr
         15                  20                  25 agc atc tct gcc aca ggg tcc aag ttt gtc cag cca gca acg cgc ctg    149
Ser Ile Ser Ala Thr Gly Ser Lys Phe Val Gln Pro Ala Thr Arg Leu
         30                  35                  40 gct cac atc ggc att gac act gca gtg ttg aac acg gac aag acc gtc    197
Ala His Ile Gly Ile Asp Thr Ala Val Leu Asn Thr Asp Lys Thr Val
         45                  50                  55 ttc aac cag cat gtc cag acc ttg ctt gat aac ctg gag cag acc cat    245
Phe Asn Gln His Val Gln Thr Leu Leu Asp Asn Leu Glu Gln Thr His
 60              65                  70                  75 ccc tgg ctc ttg acc tcc aag ctt gtg gcc aaa cca gat caa ttg atc    293
Pro Trp Leu Leu Thr Ser Lys Leu Val Ala Lys Pro Asp Gln Leu Ile
                 80                  85                  90 aag cgc cgt ggc aag agt ggc ctg ctc ttg aac gcg gac tgg gca        341
Lys Arg Arg Gly Lys Ser Gly Leu Leu Leu Asn Ala Asp Trp Ala
                     95                 100                 105 gag gtc agg acc tgg atc aca gcg cat gcg ggc aag gat gtt gtt gtt    389
Glu Val Arg Thr Trp Ile Thr Ala His Ala Gly Lys Asp Val Val Val
                110                 115                 120 gac tct gtc gcg ggt gtg ctc aag acg ttc ttg gtc gag ccc ttc att    437
Asp Ser Val Ala Gly Val Leu Lys Thr Phe Leu Val Glu Pro Phe Ile
         125                 130                 135 ccc cac cca gcc aac acg gaa tac tac atc tgc atc aac tcg gac cgc    485
Pro His Pro Ala Asn Thr Glu Tyr Tyr Ile Cys Ile Asn Ser Asp Arg
140                 145                 150                 155 gat ggc gac aac att ctc ttc aca cat gag gga ggc att gag gtt ggc    533
Asp Gly Asp Asn Ile Leu Phe Thr His Glu Gly Gly Ile Glu Val Gly
                160                 165                 170 gac gtc gat gcc aag gct ttg aag ctc cag gtc aag gtc ggc gac act    581
Asp Val Asp Ala Lys Ala Leu Lys Leu Gln Val Lys Val Gly Asp Thr
             175                 180                 185 ttc ccc acc act gcc gcc ata cag tcg gca ctg ctc aca cac gtc cct    629
Phe Pro Thr Thr Ala Ala Ile Gln Ser Ala Leu Leu Thr His Val Pro
             190                 195                 200 gcc acg aag cac gac gtc ctc atc gat ttc atc acc cgt ctc tac gcc    677
Ala Thr Lys His Asp Val Leu Ile Asp Phe Ile Thr Arg Leu Tyr Ala
     205                 210                 215 gtt tac gtc gat ctc cac ttc acc tac ctc gag atc aat ccc ttg gtc    725
Val Tyr Val Asp Leu His Phe Thr Tyr Leu Glu Ile Asn Pro Leu Val
220                 225                 230                 235 gtc ctc gac cct acc ccc gaa cac cca gcc cag gtc tac tac ttg gat    773
Val Leu Asp Pro Thr Pro Glu His Pro Ala Gln Val Tyr Tyr Leu Asp
                240                 245                 250 ctc gcc gcc aag gtc gat cag act gca gag ttc gag gct ggc ccc aag    821
Leu Ala Ala Lys Val Asp Gln Thr Ala Glu Phe Glu Ala Gly Pro Lys
             255                 260                 265 tgg gcc ttt gcc agg gct cct cag aac att gga ctg gtt gct gcc ggt    869
Trp Ala Phe Ala Arg Ala Pro Gln Asn Ile Gly Leu Val Ala Ala Gly
         270                 275                 280 tcc caa ggc gtt gat gct gga cca cct atg gat ttc cct gct cct ttc    917
Ser Gln Gly Val Asp Ala Gly Pro Pro Met Asp Phe Pro Ala Pro Phe
 285                 290                 295 ggt cgt gag ttg acc aag gag gaa gcg tat gtt cag gaa ctg gat tcc    965
Gly Arg Glu Leu Thr Lys Glu Glu Ala Tyr Val Gln Glu Leu Asp Ser
300                 305                 310                 315 aag acc ggc gcc tcg ctc aag ctg acg att ctg aac aag gac ggt cgc   1013
Lys Thr Gly Ala Ser Leu Lys Leu Thr Ile Leu Asn Lys Asp Gly Arg
                320                 325                 330
```

```
atc tgg act atg gtc gct ggc ggt gga gct tcc gtc gtg tac agt gat   1061
Ile Trp Thr Met Val Ala Gly Gly Gly Ala Ser Val Val Tyr Ser Asp
            335                 340                 345 gcc att gct gcc ttg gga cag gcg aac gag ctt gct aac tat gga gag   1109
Ala Ile Ala Ala Leu Gly Gln Ala Asn Glu Leu Ala Asn Tyr Gly Glu
        350                 355                 360 tac tct gga gca ccc acc gag acc cag act tat gaa tat gcc aag acg   1157
Tyr Ser Gly Ala Pro Thr Glu Thr Gln Thr Tyr Glu Tyr Ala Lys Thr
    365                 370                 375 atc ctc gac ttg atg act cga tca gcc atc ccc cac cct ctt ggc aag   1205
Ile Leu Asp Leu Met Thr Arg Ser Ala Ile Pro His Pro Leu Gly Lys
380                 385                 390                 395 gtt ctg att att gga ggt ggt atc gcc aac ttt aca aat gtg gcc tcg   1253
Val Leu Ile Ile Gly Gly Gly Ile Ala Asn Phe Thr Asn Val Ala Ser
                400                 405                 410 acc ttc aag ggt atc gtc cgt gcc ctg act gag ttc aag cag cct ttg   1301
Thr Phe Lys Gly Ile Val Arg Ala Leu Thr Glu Phe Lys Gln Pro Leu
            415                 420                 425 att gcc cac aag gtt cgc att ttc gtc cgc cgc ggt ggc ccc aac tat   1349
Ile Ala His Lys Val Arg Ile Phe Val Arg Arg Gly Gly Pro Asn Tyr
        430                 435                 440 cag gag ggt ctt cgc tcg atg cgc cag ctg ggt gag acg ttg ggg gtt   1397
Gln Glu Gly Leu Arg Ser Met Arg Gln Leu Gly Glu Thr Leu Gly Val
    445                 450                 455 gag atc cag gtc ttt ggt cct gag acc cac att aca gag atc gtg ccc   1445
Glu Ile Gln Val Phe Gly Pro Glu Thr His Ile Thr Glu Ile Val Pro
460                 465                 470                 475 ttg gcc ttg act gga aaa ctt tct gga cta aac cag tct ggg act gcc   1493
Leu Ala Leu Thr Gly Lys Leu Ser Gly Leu Asn Gln Ser Gly Thr Ala
                480                 485                 490 acg ccc agc gcc cat ttg tcc tct gga aat ctt ctg cag gat cag ctc   1541
Thr Pro Ser Ala His Leu Ser Ser Gly Asn Leu Leu Gln Asp Gln Leu
            495                 500                 505 ctg ggc aac aac act ccc ctg aac gct gga tcg cgc gct tcg tca cca   1589
Leu Gly Asn Asn Thr Pro Leu Asn Ala Gly Ser Arg Ala Ser Ser Pro
        510                 515                 520 cca cca ttg gag gac agg atg act tac ttc cag gac cag aat gcg gag   1637
Pro Pro Leu Glu Asp Arg Met Thr Tyr Phe Gln Asp Gln Asn Ala Glu
    525                 530                 535 tcc tca gag tct agc cac gac gag aac acg ccc ttc acg gcc cac acg   1685
Ser Ser Glu Ser Ser His Asp Glu Asn Thr Pro Phe Thr Ala His Thr
540                 545                 550                 555 cgc tct ttt att tac ggc atg cag cct cgc gcc gtc cag gga atg ctt   1733
Arg Ser Phe Ile Tyr Gly Met Gln Pro Arg Ala Val Gln Gly Met Leu
                560                 565                 570 gat ttt gat ttc att tgc aag cgc gag gtg ccc tca gtt gct gcc atg   1781
Asp Phe Asp Phe Ile Cys Lys Arg Glu Val Pro Ser Val Ala Ala Met
            575                 580                 585 gtc tac ccc ttt gga ggt gcc cat gtc caa aag ttc tac tgg ggc act   1829
Val Tyr Pro Phe Gly Gly Ala His Val Gln Lys Phe Tyr Trp Gly Thr
        590                 595                 600 aag gag acc ctc ctg cct gtc ttc acg tcc ttg gat gag gct gtt gcc   1877
Lys Glu Thr Leu Leu Pro Val Phe Thr Ser Leu Asp Glu Ala Val Ala
    605                 610                 615 aaa tac ccc gag gtt gac acc gtg gtg aac ttt gcc tct tgc cgt tcc   1925
Lys Tyr Pro Glu Val Asp Thr Val Val Asn Phe Ala Ser Cys Arg Ser
620                 625                 630                 635 gtt tat gac tcg acc cgc gag att ttc aag cac tcg aag caa atc cgc   1973
Val Tyr Asp Ser Thr Arg Glu Ile Phe Lys His Ser Lys Gln Ile Arg
                640                 645                 650
```

| | | |
|---|---|---|
| acc atc tcc atc atc gcc gag ggt gtg cca gag cgc gct cgt caa<br>Thr Ile Ser Ile Ile Ala Glu Gly Val Pro Glu Arg Arg Ala Arg Gln<br>655                      660                   665 | | 2021 |
| att ttg tgg gag gcc aaa gag cgt aat gtc ttg gtc att gga cct gcc<br>Ile Leu Trp Glu Ala Lys Glu Arg Asn Val Leu Val Ile Gly Pro Ala<br>670                      675                   680 | | 2069 |
| act gtc gga ggc atc aag ccc ggc tgc ttc aag att gga aac act gga<br>Thr Val Gly Gly Ile Lys Pro Gly Cys Phe Lys Ile Gly Asn Thr Gly<br>685                      690                   695 | | 2117 |
| gga atg atg gat aat att gta tcc tca aag ctc tac cgc gca gga tcc<br>Gly Met Met Asp Asn Ile Val Ser Ser Lys Leu Tyr Arg Ala Gly Ser<br>700                   705                 710                715 | | 2165 |
| gtg gct tat gtg tcc aag tct gga ggc atg tcc aac gag ttg aac aac<br>Val Ala Tyr Val Ser Lys Ser Gly Gly Met Ser Asn Glu Leu Asn Asn<br>720                      725                   730 | | 2213 |
| att atc tct cgc acc acc gat ggt gtc tac gag gga gtt gcc att gga<br>Ile Ile Ser Arg Thr Thr Asp Gly Val Tyr Glu Gly Val Ala Ile Gly<br>735                      740                   745 | | 2261 |
| ggg gac cgc tac cct ggt tcg act ttt att gac cac ttg ctt cgc tac<br>Gly Asp Arg Tyr Pro Gly Ser Thr Phe Ile Asp His Leu Leu Arg Tyr<br>750                      755                   760 | | 2309 |
| gag aag gat ccc ggg tgc aag atg ctt gtc ttg ttg ggc gag gtc gga<br>Glu Lys Asp Pro Gly Cys Lys Met Leu Val Leu Leu Gly Glu Val Gly<br>765                      770                   775 | | 2357 |
| ggt gtt gaa gaa tac aaa gtc tgt gag gcg atc aag aac gga gcc atc<br>Gly Val Glu Glu Tyr Lys Val Cys Glu Ala Ile Lys Asn Gly Ala Ile<br>780                      785                   790                795 | | 2405 |
| cgc aag ccc gtg att gcc tgg tgc att ggt acc tgc gcc aag atg ttt<br>Arg Lys Pro Val Ile Ala Trp Cys Ile Gly Thr Cys Ala Lys Met Phe<br>                         800                   805                   810 | | 2453 |
| gcc acc gag gtc cag ttt gga cat gct ggt gcc ctt gcc cag tca gat<br>Ala Thr Glu Val Gln Phe Gly His Ala Gly Ala Leu Ala Gln Ser Asp<br>                       815                   820                   825 | | 2501 |
| ctt gag aca gct gat gcc aag aac cgt gcc ctt cgt gcc gct ggc gtg<br>Leu Glu Thr Ala Asp Ala Lys Asn Arg Ala Leu Arg Ala Ala Gly Val<br>830                      835                   840 | | 2549 |
| atc gtc cca gag acg ttt gaa atg ctc ccc ttg gtt ttg agt cag acc<br>Ile Val Pro Glu Thr Phe Glu Met Leu Pro Leu Val Leu Ser Gln Thr<br>845                      850                   855 | | 2597 |
| tac cag gct ctc gtc aag aag ggc gtc gtc att gtc cgc tct gag ccc<br>Tyr Gln Ala Leu Val Lys Lys Gly Val Val Ile Val Arg Ser Glu Pro<br>860                      865                   870                875 | | 2645 |
| gag aca ccc aag atc cct att gac tac tcc tgg gcc cag gag ttg ggt<br>Glu Thr Pro Lys Ile Pro Ile Asp Tyr Ser Trp Ala Gln Glu Leu Gly<br>                       880                   885                   890 | | 2693 |
| ctt gtc cgc aag cca gcc tcg ttt gtg tcg act att tgt gat gac cgt<br>Leu Val Arg Lys Pro Ala Ser Phe Val Ser Thr Ile Cys Asp Asp Arg<br>                       895                   900                   905 | | 2741 |
| ggc cag gaa ctg ctc tat gct ggc atg cgc atc tcg gat gtg ttc aag<br>Gly Gln Glu Leu Leu Tyr Ala Gly Met Arg Ile Ser Asp Val Phe Lys<br>910                      915                   920 | | 2789 |
| gag gac atc ggt atc ggt ggt gtt ctc tcc ctg ctc tgg ttc aag cgc<br>Glu Asp Ile Gly Ile Gly Gly Val Leu Ser Leu Leu Trp Phe Lys Arg<br>925                      930                   935 | | 2837 |
| cgt ctc ccc gac tat gcc tgc aag ttt atc gag atg gtc ctc atg ctc<br>Arg Leu Pro Asp Tyr Ala Cys Lys Phe Ile Glu Met Val Leu Met Leu<br>940                      945                   950                955 | | 2885 |
| aca gct gat cat ggt cct gct gtt tcg ggt gct cat aac acg att gtg<br>Thr Ala Asp His Gly Pro Ala Val Ser Gly Ala His Asn Thr Ile Val<br>                       960                   965                   970 | | 2933 |

| | | | | | | | | | | | | | | | |
|---|---|---|---|---|---|---|---|---|---|---|---|---|---|---|---|
| acc | gct | cgt | gca | ggc | aag | gat | ctt | gtt | tcg | tct | ctg | tgc | gcg | ggt ctg | 2981 |
| Thr | Ala | Arg | Ala | Gly | Lys | Asp | Leu | Val | Ser | Ser | Leu | Cys | Ala | Gly Leu | |
| | | 975 | | | | | 980 | | | | | 985 | | | |

```
ttg acg att gga gac cgt ttt gga ggc gca ttg gac gga  gcc gct gag     3029
Leu Thr Ile Gly Asp Arg Phe Gly Gly Ala Leu Asp Gly  Ala Ala Glu
        990             995                 1000 cag ttc tcg tct gca tac gac  aag tcg ctc tcg ccc  cgc gag ttt        3074
Gln Phe Ser Ser Ala Tyr Asp  Lys Ser Leu Ser Pro  Arg Glu Phe
    1005                1010                 1015 gtg tcg tcg atg aga aag cag  aac aag ctg att ttg  ggt att ggc        3119
Val Ser Ser Met Arg Lys Gln  Asn Lys Leu Ile Leu  Gly Ile Gly
    1020                1025                 1030 cac aag atc aag tcg cgc acg  aac cct gat ttg cgt  gtg gag att        3164
His Lys Ile Lys Ser Arg Thr  Asn Pro Asp Leu Arg  Val Glu Ile
    1035                1040                 1045 att aag aac tac gcc aag gcg  cac ttc cct gcc acg  cct gtg ctg        3209
Ile Lys Asn Tyr Ala Lys Ala  His Phe Pro Ala Thr  Pro Val Leu
    1050                1055                 1060 gat tat gcc ctg gct gtg gag  acc atc acc acc tcc  aag aag gat        3254
Asp Tyr Ala Leu Ala Val Glu  Thr Ile Thr Thr Ser  Lys Lys Asp
    1065                1070                 1075 aac ttg atc ctg aac gtg gat  gga gcc att ggt atc  ttg ttt gtg        3299
Asn Leu Ile Leu Asn Val Asp  Gly Ala Ile Gly Ile  Leu Phe Val
    1080                1085                 1090 gac ttg ctg aga aac tcg gga  gcg ttc acg cgc gag  gag gca gag        3344
Asp Leu Leu Arg Asn Ser Gly  Ala Phe Thr Arg Glu  Glu Ala Glu
    1095                1100                 1105 gaa tac atc aag att gga act  ttg aat ggt ctc ttt  gtc ctg ggc        3389
Glu Tyr Ile Lys Ile Gly Thr  Leu Asn Gly Leu Phe  Val Leu Gly
    1110                1115                 1120 cgg acg att gga ttc att gga  cac ttc ttg gac cag  aag agg ctg        3434
Arg Thr Ile Gly Phe Ile Gly  His Phe Leu Asp Gln  Lys Arg Leu
    1125                1130                 1135 aag cag gga ttg tac aga cac  cct tgg gac gat atc  tcg tac ctg        3479
Lys Gln Gly Leu Tyr Arg His  Pro Trp Asp Asp Ile  Ser Tyr Leu
    1140                1145                 1150 act cct ggt aac gag ctc gga  cgg aca gtt gcg tcg  ctg gac tcc        3524
Thr Pro Gly Asn Glu Leu Gly  Arg Thr Val Ala Ser  Leu Asp Ser
    1155                1160                 1165 atc aac aag aag gct gcg taagcagtcg ttatacatag catcatcttt             3572
Ile Asn Lys Lys Ala Ala
    1170 ttgtttttct cgtgtgtgct cgtgtcttat aaagacagat gtccatccta ttttctttga    3632 acaaaaaaaa aaaaaaaaaa aaaaaaaaaa aaaaaaaaaa aaaaaaaama aaaa          3686
```

<210> SEQ ID NO 7
<211> LENGTH: 3540
<212> TYPE: DNA
<213> ORGANISM: Mortierella alpina

<400> SEQUENCE: 7

```
atgtctgcta aagccgttcg cgaatacgat ggaaagctgc tcttggccca ctggcttcac     60
cgtgttgccg tgcccgaatc agagaccgca ggatcagcaa caacgggatc caagttcgtc    120
cagcccacca cccgccttgc ccacatctcc atcgacacct cgctcttgca ggacaagacc    180
cagttcgatc agcacgtccg ctcgaccttg atcagctcg aggtctcgca cccttggctg     240
ttgaccaaca agctggtcgc caagcctgac cagttgatca agcgtcgtgg aaagagcggc    300
ttgctgctct tgaacgccga atgggctgag gctagagcct ggatcgagaa gcacgcggcc    360
```

```
aaggacgtcc ttgtggactc ggttcccggt gttctcaaga ccttcctcgt cgagcccttc    420
attccccacc cttctaacac tgagtactac atctgcatca actcagatcg tgatggtgac    480
aacatcctct tcacgcacga gggaggtatc gaggtcggag atgttgatgc caaggcattg    540
aagctccagg tgaaggttca ggacgccttc cccaccgcag aggccattcg ctcggctctc    600
ctggtccatg tccctgaggc caagcacgat gttcttgttg actttatcac tcgcctctat    660
gctgtttaca tcgacctcca cttcacctac cttgagatca ccccttggt cgtcttggat     720 cccacagagg acgagcctgc tcgtgtctac tacctcgacc tggctgctaa gctcgatcag    780
actgcagagt tcgaggctgg tcccaagtgg gccatcgcca gagctcctca gaacattgga    840
attgctggcg tcatccccac cactgttggc gctgatgctg gccctggcat ggatttcccc    900
gcacctttcg gtcgtgaatt gaccaaggag gaggcctatg ttcaggagct ggactctaag    960
accggtgctt cgctcaagct caccatcctg aacaaggatg gacgcatctg gaccatggtt   1020
gctggaggcg gtgcctctgt cgtttacagt gatgccatcg ctgcccttgg ccaggctgac   1080
gagctcgcca actacggaga gtactctggt gcccccaccg agacccagac ctatgaatac   1140
gccaagacca tccttgacct tatgacccgc tctgccaccc ctcaccccga gggcaaggtc   1200
ctgatcattg gaggaggtat cgccaacttc actaacgtcg cctcgacctt caagggaatt   1260
gtccgcgctc ttaccgagtt taaacagccc ttgatcgccc acaaggtccg catctttgtc   1320
cgtcgtggtg gtcccaacta ccaggagggt cttcgctcca tgcgtcaact cggcgagtcc   1380
ttgggagttg agatccaggt cttttggaccc gagacccaca tcaccgagat tgttcctctg   1440
gccttgactg gacgctcttc cgacaacttg gctgccacca cgccaacaa cggcagcgcc    1500 tcgtccggaa acctccttca ggatcagctc ttgggcacca cagcaaccct caacacccct   1560
gttcccactg cccccgtctc ccgtgctggc actcctcccg ccagcgagag gatgacttac   1620
ttcacggacg cagacgcaaa gaaggtcggc cacgattcca acgttccctt cactgcccag   1680
actcgctcgt tcatctacgg aatgcagccc cgtgctgttc agggaatgct cgactttgat   1740
ttcatctgca gcgtgaggt ccctcggtc gcagccatga tctaccccctt tggcggtgct   1800 cacgttcaga agttctactg gggcaccaag gagactctct tgcccgttta cactactctg   1860
gaggaggcca ctgccaagtt ccccgaggtt gataccgtcg tcaactttgc ctcgtgccgc   1920
tctgtttacc agtccacggt tgatatcctc agtcactctg accagatcaa gacgatctcg   1980
atcattgccg agggtgtccc cgagcgtcgt gctcgccaga tcctctggga ggccaaggcc   2040
aagaacgtgc tcgtgatcgg accagccact gtcggaggca tcaagcccgg ctgcttcaag   2100
atcggaaaca ctggaggtat gatgacaac attgtctcgt ccaagttgta ccgcgccggt    2160
tctgttgcct acgtctccaa gtctggcggt atgtccaacg agctgaacaa catcatctcg   2220
cgcaccactg acggtgtcta cgagggagtc gccatcggag agaccgtta ccctggatcg    2280 accttcatcg accacttgct tcgctatgag cgggaccca actgcaagat gttggtcttg   2340
ctcggagagg tcgaggtgt cgaggagtac aaggtctgtg aggcgatcaa gaacgggacc    2400
atccgcaagc ccgtgattgc ctggtgcatc ggtacctgcg ccaagatgtt tgccaccgag   2460
gtccagttcg acacgccgg tgccttggcc cagtccgatc tcgagactgc cgatgccaag   2520
aacaaggctc tccgcgccgc tggtgtggtc gttcccgaga cctttgagaa gttgcccttg   2580
gtcttgagcc agaccttcca gaccttggtc aagaacggaa ccatccagct caagcccgag   2640
cccgagactc ccaagatccc catcgattac tcctgggccc aggagctcgg acttgtccgt   2700
aagcctgcct cgttcgtgtc gaccatttgc gatgaccgtg gtcaggagtt gctctatgcc   2760
```

```
ggtatgcgta tctcggacgt cttcaaggag gacattggta tcggaggtgt tctgtccttg    2820
ctctggttca agcgccgtct gcccgactac gcctgcaagt ttatcgagat ggttctcatg    2880
ctcactgctg atcacggtcc cgccgtctca ggtgcacaca acaccatcgt cactgcccgt    2940
gccggcaagg atttggtttc gtcgttgtgc gcaggtcttt tgacgattgg tgaccgcttc    3000
ggaggtgcct tggatggtgc cgccgagcag ttctcgtctg catacgacaa gtcgctcacg    3060
ccccgtgagt ttgtctctgt gatgcgtaag cagaacaagt tgattctcgg tatcggccac    3120
aagatcaagt cgcgcacgaa ccccgatctg cgtgtcgaga tcatcaagga gtacgccaag    3180
aagcacttcc cctcgacccc tgttctggac tatgcccttc aggtggagaa catcacgacg    3240
tccaagaagg acaacttgat cttgaacgtc gatggagcga tcggaatctt gtttgtggat    3300
ctgttgagaa actcgggcgc gttcacgcgt gaggaggctg aggagtacat caagattgga    3360
acgttgaacg gtctgtttgt attgggtcgc tcgatcggat tcattggaca ttacttggac    3420
cagaagaggc tgaagcaggg cttgtacaga catccttggg atgatatctc gtacctgacc    3480
cccggcaatg agctcggacg gacggttgcc tcgctggatt cgatcaacaa gaaggcctaa    3540
```

<210> SEQ ID NO 8
<211> LENGTH: 3525
<212> TYPE: DNA
<213> ORGANISM: Mortierella alpina

<400> SEQUENCE: 8

```
atgtctgcca aagctgttcg tgagtatgat ggaaagctgc tgttggcaca ctggctcctg      60
cgcacgccta tccctgccac cagcatctct gccacagggt ccaagtttgt ccagccagca     120
acgcgcctgg ctcacatcgg cattgacact gcagtgttga acggacaa gaccgtcttc       180 aaccagcatg tccagacctt gcttgataac ctggagcaga cccatccctg gctcttgacc     240
tccaagcttg tggccaaacc agatcaattg atcaagcgcc gtggcaagag tggcctgctg     300
ctcttgaacg cggactgggc agaggtcagg acctggatca cagcgcatgc gggcaaggat     360
gttgttgttg actctgtcgc gggtgtgctc aagacgttct tggtcgagcc cttcattccc     420
cacccagcca acacggaata ctacatctgc atcaactcgg accgcgatgg cgacaacatt     480
ctcttcacac atgagggagg cattgaggtt ggcgacgtcg atgccaaggc tttgaagctc     540
caggtcaagg tcggcgacac tttccccacc actgccgcca tacagtcggc actgctcaca     600
cacgtccctg ccacgaagca cgacgtcctc atcgatttca tcacccgtct ctacgccgtt     660
tacgtcgatc tccacttcac ctacctcgag atcaatccct tggtcgtcct cgaccctacc     720
cccgaacacc cagcccaggt ctactacttg gatctcgccg ccaaggtcga tcagactgca     780
gagttcgagg ctggccccaa gtgggccttt gccagggctc tcagaacat ggactggtt      840 gctgccggtt ccaaggcgt tgatgctgga ccacctatgg atttccctgc tccttcggt      900 cgtgagttga ccaaggagga agcgtatgtt caggaactgg attccaagac cggcgcctcg     960
ctcaagctga cgattctgaa caaggacggt cgcatctgga ctatggtcgc tggcggtgga    1020
gcttccgtcg tgtacagtga tgccattgct gccttgggac aggcgaacga gcttgctaac    1080
tatggagagt actctggagc acccaccgag acccagactt atgaatatgc caagacgatc    1140
ctcgacttga tgactcgatc agccatcccc caccctcttg caaggttct gattattgga    1200 ggtggtatcg ccaactttac aaatgtggcc tcgaccttca agggtatcgt ccgtgccctg    1260
actgagttca agcagccttt gattgcccac aaggttcgca ttttcgtccg ccgcggtggc    1320
cccaactatc aggagggtct tcgctcgatg cgccagctgg gtgagacgtt gggggttgag    1380
```

```
atccaggtct ttggtcctga gacccacatt acagagatcg tgcccttggc cttgactgga    1440
aaactttctg gactaaacca gtctgggact gccacgccca gcgcccattt gtcctctgga    1500
aatcttctgc aggatcagct cctgggcaac aacactcccc tgaacgctgg atcgcgcgct    1560
tcgtcaccac caccattgga ggacaggatg acttacttcc aggaccagaa tgcggagtcc    1620
tcagagtcta gccacgacga gaacacgccc ttcacggccc acacgcgctc ttttatttac    1680
ggcatgcagc ctcgcgccgt ccagggaatg cttgattttg atttcatttg caagcgcgag    1740
gtgccctcag ttgctgccat ggtctacccc tttggaggtg cccatgtcca aaagttctac    1800
tggggcacta aggagaccct cctgcctgtc ttcacgtcct tggatgaggc tgttgccaaa    1860
taccccgagg ttgacaccgt ggtgaacttt gcctcttgcc gttccgttta tgactcgacc    1920
cgcgagattt tcaagcactc gaagcaaatc cgcaccatct ccatcatcgc cgagggtgtg    1980
ccagagcgcc gcgctcgtca aattttgtgg gaggccaaag agcgtaatgt cttggtcatt    2040
ggacctgcca ctgtcggagg catcaagccc ggctgcttca agattggaaa cactggagga    2100
atgatggata atattgtatc ctcaaagctc taccgcgcag gatccgtggc ttatgtgtcc    2160
aagtctggag gcatgtccaa cgagttgaac aacattatct ctcgcaccac cgatggtgtc    2220
tacgagggag ttgccattgg aggggaccgc taccctggtt cgactttat tgaccacttg    2280 cttcgctacg agaaggatcc cggtgcaag atgcttgtct tgttgggcga ggtcggaggt    2340
gttgaagaat acaaagtctg tgaggcgatc aagaacggag ccatccgcaa gcccgtgatt    2400
gcctggtgca ttggtacctg cgccaagatg tttgccaccg aggtccagtt tggacatgct    2460
ggtgcccttg cccagtcaga tcttgagaca gctgatgcca agaaccgtgc ccttcgtgcc    2520
gctggcgtga tcgtcccaga gacgtttgaa atgctcccct tggttttgag tcagacctac    2580
caggctctcg tcaagaaggg cgtcgtcatt gtccgctctg agcccgagac acccaagatc    2640
cctattgact actcctgggc ccaggagttg ggtcttgtcc gcaagccagc ctcgtttgtg    2700
tcgactattt gtgatgaccg tggccaggaa ctgctctatg ctggcatgcg catctcggat    2760
gtgttcaagg aggacatcgg tatcggtggt gttctctccc tgctctggtt caagcgccgt    2820
ctccccgact atgcctgcaa gtttatcgag atggtcctca tgctcacagc tgatcatggt    2880
cctgctgttt cgggtgctca taacacgatt gtgaccgctc gtgcaggcaa ggatcttgtt    2940
tcgtctctgt gcgcgggtct gttgacgatt ggagaccgtt ttggaggcgc attggacgga    3000
gccgctgagc agttctcgtc tgcatacgac aagtcgctct cgccccgcga gtttgtgtcg    3060
tcgatgagaa agcagaacaa gctgattttg ggtattggcc acaagatcaa gtcgcgcacg    3120
aaccctgatt tgcgtgtgga gattattaag aactacgcca aggcgcactt ccctgccacg    3180
cctgtgctgg attatgccct ggctgtggag accatcacca cctccaagaa ggataacttg    3240
atcctgaacg tggatggagc cattggtatc ttgttgtgg acttgctgag aaactcggga    3300
gcgttcacgc gcgaggaggc agaggaatac atcaagattg aactttgaa tggtctcttt    3360 gtcctgggcc ggacgattgg attcattgga cacttcttgg accagaagag gctgaagcag    3420
ggattgtaca gacacccttg gacgatatc tcgtacctga ctcctggtaa cgagctcgga    3480
cggacagttg cgtcgctgga ctccatcaac aagaaggctg cgtaa               3525
```

<210> SEQ ID NO 9
<211> LENGTH: 3537
<212> TYPE: DNA
<213> ORGANISM: Mortierella alpina

<400> SEQUENCE: 9

```
atgtctgcta aagccgttcg cgaatacgat ggaaagctgc tcttggccca ctggcttcac    60
cgtgttgccg tgcccgaatc agagaccgca ggatcagcaa caacgggatc caagttcgtc   120
cagcccacca cccgccttgc ccacatctcc atcgacacct cgctcttgca ggacaagacc   180
cagttcgatc agcacgtccg ctcgaccttg gatcagctcg aggtctcgca cccttggctg   240
ttgaccaaca agctggtcgc caagcctgac cagttgatca agcgtcgtgg aaagagcggc   300
ttgctgctct tgaacgccga atgggctgag gctagagcct ggatcgagaa gcacgcggcc   360
aaggacgtcc ttgtggactc ggttccggt gttctcaaga ccttcctcgt cgagcccttc    420
attccccacc cttctaacac tgagtactac atctgcatca actcagatcg tgatggtgac   480
aacatcctct tcacgcacga gggaggtatc gaggtcggag atgttgatgc caaggcattg   540
aagctccagg tgaaggttca ggacgccttc cccaccgcag aggccattcg ctcggctctc   600
ctggtccatg tccctgaggc caagcacgat gttcttgttg actttatcac tcgcctctat   660
gctgtttaca tcgacctcca cttcacctac cttgagatca ccccttggt cgtcttggat    720 cccacagagg acgagcctgc tcgtgtctac tacctcgacc tggctgctaa gctcgatcag   780
actgcagagt tcgaggctgg tcccaagtgg gccatcgcca gagctcctca gaacattgga   840
attgctggcg tcatccccac cactgttggc gctgatgctg ccctggcat ggatttcccc    900 gcacctttcg gtcgtgaatt gaccaaggag gaggcctatg ttcaggagct ggactctaag   960
accggtgctt cgctcaagct caccatcctg aacaaggatg gacgcatctg gaccatggtt  1020 gctgaggcg tgcctctgt cgtttacagt gatgccatcg ctgcccttgg ccaggctgac    1080
gagctcgcca actacggaga gtactctggt gcccccaccg agacccagac ctatgaatac  1140
gccaagacca tccttgacct tatgacccgc tctgccaccc ctcaccccga ggcaaggtc   1200 ctgatcattg gaggaggtat cgccaacttc actaacgtcg cctcgacctt caagggaatt  1260
gtccgcgctc ttaccgagtt taaacagccc ttgatcgccc acaaggtccg catctttgtc  1320
cgtcgtggtg gtcccaacta ccaggagggt cttcgctcca tgcgtcaact cggcgagtcc  1380
ttgggagttg agatccaggt cttggaccc gagacccaca tcaccgagat tgttcctctg   1440
gccttgactg gacgctcttc cgacaacttg gctgccacca acgccaacaa cggcagcgcc  1500
tcgtccggaa acctccttca ggatcagctc ttgggcacca acagcaacct caacaccccc  1560
gttcccactg cccccgtctc ccgtgctggc actcctcccg ccagcgagag gatgacttac  1620
ttcacggacg cagacgcaaa gaaggtcggc cacgattcca acgttccctt cactgcccag  1680
actcgctcgt tcatctacgg aatgcagccc cgtgctgttc agggaatgct cgactttgat  1740
ttcatctgca agcgtgaggt cccctcggtc gcagccatga tctaccccct tggcggtgct  1800
cacgttcaga agttctactg gggcaccaag gagactctct gcccgtttta cactactctg  1860
gaggaggcca ctgccaagtt ccccgaggtt gataccgtcg tcaactttgc ctcgtgccgc  1920
tctgtttacc agtccacggt tgatatcctc agtcactctg accagatcaa gacgatctcg  1980
atcattgccg agggtgtccc cgagcgtcgt gctcgccaga tcctctggga ggccaaggcc  2040
aagaacgtgc tcgtgatcgg accagccact gtcgaggca tcaagcccgg ctgcttcaag   2100
atcggaaaca ctggaggtat gatgacaac attgtctcgt ccaagttgta ccgcgccggt   2160
tctgttgcct acgtctccaa gtctggcggt atgtccaacg agctgaacaa catcatctcg  2220
cgcaccactg acggtgtcta cgagggagtc gccatcggag agaccgttta ccctggatcg  2280
accttcatcg accacttgct tcgctatgag cgggacccca actgcaagat gttggtcttg  2340
ctcggagagg tcggaggtgt cgaggagtac aaggtctgtg aggcgatcaa gaacgggacc  2400
```

```
atccgcaagc cgtgattgc ctggtgcatc ggtacctgcg ccaagatgtt tgccaccgag    2460
gtccagttcg gacacgccgg tgccttggcc cagtccgatc tcgagactgc cgatgccaag    2520
aacaaggctc tccgcgccgc tggtgtggtc gttcccgaga cctttgagaa gttgcccttg    2580
gtcttgagcc agaccttcca gaccttggtc aagaacggaa ccatccagct caagcccgag    2640
cccgagactc ccaagatccc catcgattac tcctgggccc aggagctcgg acttgtccgt    2700
aagcctgcct cgttcgtgtc gaccatttgc gatgaccgtg gtcaggagtt gctctatgcc    2760
ggtatgcgta tctcggacgt cttcaaggag acattggta tcggaggtgt tctgtccttg    2820
ctctggttca agcgccgtct gcccgactac gcctgcaagt ttatcgagat ggttctcatg    2880
ctcactgctg atcacggtcc cgccgtctca ggtgcacaca acaccatcgt cactgcccgt    2940
gccggcaagg atttggtttc gtcgttgtgc gcaggtcttt tgacgattgg tgaccgcttc    3000
ggaggtgcct tggatggtgc cgccgagcag ttctcgtctg catacgacaa gtcgctcacg    3060
ccccgtgagt ttgtctctgt gatgcgtaag cagaacaagt tgattctcgg tatcggccac    3120
aagatcaagt cgcgcacgaa ccccgatctg cgtgtcgaga tcatcaagga gtacgccaag    3180
aagcacttcc cctcgacccc tgttctggac tatgcccttc aggtggagaa catcacgacg    3240
tccaagaagg acaacttgat cttgaacgtc gatggagcga tcggaatctt gtttgtggat    3300
ctgttgagaa actcgggcgc gttcacgcgt gaggaggctg aggagtacat caagattgga    3360
acgttgaacg gtctgtttgt attgggtcgc tcgatcggat tcattggaca ttacttggac    3420
cagaagaggc tgaagcaggg cttgtacaga catccttggg atgatatctc gtacctgacc    3480
cccggcaatg agctcggacg gacggttgcc tcgctggatt cgatcaacaa gaaggcc      3537

<210> SEQ ID NO 10
<211> LENGTH: 3522
<212> TYPE: DNA
<213> ORGANISM: Mortierella alpina

<400> SEQUENCE: 10
atgtctgcca aagctgttcg tgagtatgat ggaaagctgc tgttggcaca ctggctcctg      60
cgcacgccta tccctgccac cagcatctct gccacagggt ccaagtttgt ccagccagca     120
acgcgcctgg ctcacatcgg cattgacact gcagtgttga acacggacaa gaccgtcttc     180
aaccagcatg tccagacctt gcttgataac ctggagcaga cccatccctg gctcttgacc     240
tccaagcttg tggccaaacc agatcaattg atcaagcgcc gtggcaagag tggcctgctg     300
ctcttgaacg cggactgggc agaggtcagg acctggatca cagcgcatgc gggcaaggat     360
gttgttgttg actctgtcgc gggtgtgctc aagacgttct tggtcgagcc cttcattccc     420
cacccagcca acacggaata ctacatctgc atcaactcgg accgcgatgg cgacaacatt     480
ctcttcacac atgagggagg cattgaggtt ggcgacgtcg atgccaaggc tttgaagctc     540
caggtcaagg tcgcgacac tttccccacc actgccgcca tacagtcggc actgctcaca     600
cacgtccctg ccacgaagca cgacgtcctc atcgatttca tcacccgtct ctacgccgtt     660
tacgtcgatc tccacttcac ctacctcgag atcaatccct tggtcgtcct cgaccctacc     720
cccgaacacc cagcccaggt ctactacttg gatctcgccg ccaaggtcga tcagactgca     780
gagttcgagg ctggccccaa gtgggccttt gccaggctgc tcagaacat ggactggtt      840 gctgccggtt cccaaggcgt tgatgctgga ccacctatgg atttccctgc tcctttcggt     900
cgtgagttga ccaaggagga agcgtatgtt caggaactgg attccaagac cggcgcctcg     960
ctcaagctga cgattctgaa caaggacggt cgcatctgga ctatggtcgc tggcggtgga    1020
```

```
gcttccgtcg tgtacagtga tgccattgct gccttgggac aggcgaacga gcttgctaac    1080
tatggagagt actctggagc acccaccgag acccagactt atgaatatgc caagacgatc    1140
ctcgacttga tgactcgatc agccatcccc caccctcttg gcaaggttct gattattgga    1200
ggtggtatcg ccaactttac aaatgtggcc tcgaccttca agggtatcgt ccgtgccctg    1260
actgagttca agcagccttt gattgcccac aaggttcgca ttttcgtccg ccgcggtggc    1320
cccaactatc aggagggtct cgctcgatg cgccagctgg gtgagacgtt gggggttgag    1380
atccaggtct ttggtcctga gacccacatt acagagatcg tgcccttggc cttgactgga    1440
aaactttctg gactaaacca gtctgggact gccacgccca gcgcccattt gtcctctgga    1500
aatcttctgc aggatcagct cctgggcaac aacactcccc tgaacgctgg atcgcgcgct    1560
tcgtcaccac caccattgga ggacaggatg acttacttcc aggaccagaa tgcggagtcc    1620
tcagagtcta gccacgacga gaacacgccc ttcacggccc acgcgcgctc ttttatttac    1680
ggcatgcagc ctcgcgccgt ccagggaatg cttgattttg atttcatttg caagcgcgag    1740
gtgccctcag ttgctgccat ggtctacccc tttggaggtg cccatgtcca aaagttctac    1800
tggggcacta aggagaccct cctgcctgtc ttcacgtcct tggatgaggc tgttgccaaa    1860
taccccgagg ttgacaccgt ggtgaacttt gcctcttgcc gttccgttta tgactcgacc    1920
cgcgagattt tcaagcactc gaagcaaatc cgcaccatct ccatcatcgc cgagggtgtg    1980
ccagagcgcc gcgctcgtca aattttgtgg gaggccaaag agcgtaatgt cttggtcatt    2040
ggacctgcca ctgtcggagg catcaagccc ggctgcttca agattggaaa cactggagga    2100
atgatggata atattgtatc ctcaaagctc taccgcgcag gatccgtggc ttatgtgtcc    2160
aagtctggag gcatgtccaa cgagttgaac aacattatct ctcgcaccac cgatggtgtc    2220
tacgagggag ttgccattgg agggaccgc taccctggtt cgacttttat tgaccacttg    2280
cttcgctacg agaaggatcc cggtgcaag atgcttgtct tgttgggcga ggtcggaggt    2340
gttgaagaat acaaagtctg tgaggcgatc aagaacggag ccatccgcaa gcccgtgatt    2400
gcctggtgca ttggtacctg cgccaagatg tttgccaccg aggtccagtt tggacatgct    2460
ggtgcccttg cccagtcaga tcttgagaca gctgatgcca agaaccgtgc ccttcgtgcc    2520
gctggcgtga tcgtcccaga gacgtttgaa atgctcccct tggttttgag tcagacctac    2580
caggctctcg tcaagaaggg cgtcgtcatt gtccgctctg agcccgagac acccaagatc    2640
cctattgact actcctgggc ccaggagttg ggtcttgtcc gcaagccagc ctcgtttgtg    2700
tcgactattt gtgatgaccg tggccaggaa ctgctctatg ctggcatgcg catctcggat    2760
gtgttcaagg aggacatcgg tatcggtggt gttctctccc tgctctggtt caagcgccgt    2820
ctccccgact atgcctgcaa gtttatcgag atggtcctca tgctcacagc tgatcatggt    2880
cctgctgttt cgggtgctca taacacgatt gtgaccgctc gtgcaggcaa ggatcttgtt    2940
tcgtctctgt gcgcgggtct gttgacgatt ggagaccgtt ttggaggcgc attggacgga    3000
gccgctgagc agttctcgtc tgcatacgac aagtcgctct cgccccgcga gtttgtgtcg    3060
tcgatgagaa agcagaacaa gctgattttg ggtattggcc acaagatcaa gtcgcgcacg    3120
aaccctgatt tgcgtgtgga gattattaag aactacgcca aggcgcactt ccctgccacg    3180
cctgtgctgg attatgccct ggctgtggag accatcacca cctccaagaa ggataacttg    3240
atcctgaacg tggatggagc cattggtatc ttgtttgtgg acttgctgag aaactcggga    3300
gcgttcacgc gcgaggaggc agaggaatac atcaagattg aactttgaa tggtctcttt    3360 gtcctgggcc ggacgattgg attcattgga cacttcttgg accagaagag gctgaagcag    3420
```

```
ggattgtaca gacacccttg ggacgatatc tcgtacctga ctcctggtaa cgagctcgga    3480
cggacagttg cgtcgctgga ctccatcaac aagaaggctg cg                      3522
```

<210> SEQ ID NO 11
<211> LENGTH: 1179
<212> TYPE: PRT
<213> ORGANISM: Mortierella alpina

<400> SEQUENCE: 11

| | | | | | | | | | | | | | | |
|---|---|---|---|---|---|---|---|---|---|---|---|---|---|---|
| Met | Ser | Ala | Lys | Ala | Val | Arg | Glu | Tyr | Asp | Gly | Lys | Leu | Leu | Ala |
| 1 | | | | 5 | | | | | 10 | | | | | 15 |
| His | Trp | Leu | His | Arg | Val | Ala | Val | Pro | Glu | Ser | Glu | Thr | Ala | Gly | Ser |
| | | | 20 | | | | | 25 | | | | | 30 | | |
| Ala | Thr | Thr | Gly | Ser | Lys | Phe | Val | Gln | Pro | Thr | Thr | Arg | Leu | Ala | His |
| | | 35 | | | | | 40 | | | | | 45 | | | |
| Ile | Ser | Ile | Asp | Thr | Ser | Leu | Leu | Gln | Asp | Lys | Thr | Gln | Phe | Asp | Gln |
| 50 | | | | | 55 | | | | | 60 | | | | | |
| His | Val | Arg | Ser | Thr | Leu | Asp | Gln | Leu | Glu | Val | Ser | His | Pro | Trp | Leu |
| 65 | | | | | 70 | | | | | 75 | | | | | 80 |
| Leu | Thr | Asn | Lys | Leu | Val | Ala | Lys | Pro | Asp | Gln | Leu | Ile | Lys | Arg | Arg |
| | | | | 85 | | | | | 90 | | | | | 95 | |
| Gly | Lys | Ser | Gly | Leu | Leu | Leu | Asn | Ala | Glu | Trp | Ala | Glu | Ala | Arg | |
| | | | 100 | | | | | 105 | | | | | 110 | | |
| Ala | Trp | Ile | Glu | Lys | His | Ala | Ala | Lys | Asp | Val | Leu | Val | Asp | Ser | Val |
| | | | 115 | | | | | 120 | | | | | 125 | | |
| Pro | Gly | Val | Leu | Lys | Thr | Phe | Leu | Val | Glu | Pro | Phe | Ile | Pro | His | Pro |
| | 130 | | | | | 135 | | | | | 140 | | | | |
| Ser | Asn | Thr | Glu | Tyr | Tyr | Ile | Cys | Ile | Asn | Ser | Asp | Arg | Asp | Gly | Asp |
| 145 | | | | | 150 | | | | | 155 | | | | | 160 |
| Asn | Ile | Leu | Phe | Thr | His | Glu | Gly | Gly | Ile | Glu | Val | Gly | Asp | Val | Asp |
| | | | | 165 | | | | | 170 | | | | | 175 | |
| Ala | Lys | Ala | Leu | Lys | Leu | Gln | Val | Lys | Val | Gln | Asp | Ala | Phe | Pro | Thr |
| | | | 180 | | | | | 185 | | | | | 190 | | |
| Ala | Glu | Ala | Ile | Arg | Ser | Ala | Leu | Leu | Val | His | Val | Pro | Glu | Ala | Lys |
| | | | 195 | | | | | 200 | | | | | 205 | | |
| His | Asp | Val | Leu | Val | Asp | Phe | Ile | Thr | Arg | Leu | Tyr | Ala | Val | Tyr | Ile |
| | 210 | | | | | 215 | | | | | 220 | | | | |
| Asp | Leu | His | Phe | Thr | Tyr | Leu | Glu | Ile | Asn | Pro | Leu | Val | Val | Leu | Asp |
| 225 | | | | | 230 | | | | | 235 | | | | | 240 |
| Pro | Thr | Glu | Asp | Glu | Pro | Ala | Arg | Val | Tyr | Tyr | Leu | Asp | Leu | Ala | Ala |
| | | | | 245 | | | | | 250 | | | | | 255 | |
| Lys | Leu | Asp | Gln | Thr | Ala | Glu | Phe | Glu | Ala | Gly | Pro | Lys | Trp | Ala | Ile |
| | | | 260 | | | | | 265 | | | | | 270 | | |
| Ala | Arg | Ala | Pro | Gln | Asn | Ile | Gly | Ile | Ala | Gly | Val | Ile | Pro | Thr | Thr |
| | | | 275 | | | | | 280 | | | | | 285 | | |
| Val | Gly | Ala | Asp | Ala | Gly | Pro | Gly | Met | Asp | Phe | Pro | Ala | Pro | Phe | Gly |
| | 290 | | | | | 295 | | | | | 300 | | | | |
| Arg | Glu | Leu | Thr | Lys | Glu | Glu | Ala | Tyr | Val | Gln | Glu | Leu | Asp | Ser | Lys |
| 305 | | | | | 310 | | | | | 315 | | | | | 320 |
| Thr | Gly | Ala | Ser | Leu | Lys | Leu | Thr | Ile | Leu | Asn | Lys | Asp | Gly | Arg | Ile |
| | | | | 325 | | | | | 330 | | | | | 335 | |
| Trp | Thr | Met | Val | Ala | Gly | Gly | Ala | Ser | Val | Val | Tyr | Ser | Asp | Ala | |
| | | | 340 | | | | | 345 | | | | | 350 | | |
| Ile | Ala | Ala | Leu | Gly | Gln | Ala | Asp | Glu | Leu | Ala | Asn | Tyr | Gly | Glu | Tyr |

```
                355                 360                 365
Ser Gly Ala Pro Thr Glu Thr Gln Thr Tyr Glu Tyr Ala Lys Thr Ile
    370                 375                 380
Leu Asp Leu Met Thr Arg Ser Ala Thr Pro His Pro Glu Gly Lys Val
385                 390                 395                 400
Leu Ile Ile Gly Gly Ile Ala Asn Phe Thr Asn Val Ala Ser Thr
                405                 410                 415
Phe Lys Gly Ile Val Arg Ala Leu Thr Glu Phe Lys Gln Pro Leu Ile
                420                 425                 430
Ala His Lys Val Arg Ile Phe Val Arg Arg Gly Gly Pro Asn Tyr Gln
                435                 440                 445
Glu Gly Leu Arg Ser Met Arg Gln Leu Gly Glu Ser Leu Gly Val Glu
    450                 455                 460
Ile Gln Val Phe Gly Pro Glu Thr His Ile Thr Glu Ile Val Pro Leu
465                 470                 475                 480
Ala Leu Thr Gly Arg Ser Ser Asp Asn Leu Ala Ala Thr Asn Ala Asn
                485                 490                 495
Asn Gly Ser Ala Ser Ser Gly Asn Leu Leu Gln Asp Gln Leu Leu Gly
                500                 505                 510
Thr Asn Ser Asn Leu Asn Thr Pro Val Pro Thr Ala Pro Val Ser Arg
                515                 520                 525
Ala Gly Thr Pro Pro Ala Ser Glu Arg Met Thr Tyr Phe Thr Asp Ala
                530                 535                 540
Asp Ala Lys Lys Val Gly His Asp Ser Asn Val Pro Phe Thr Ala Gln
545                 550                 555                 560
Thr Arg Ser Phe Ile Tyr Gly Met Gln Pro Arg Ala Val Gln Gly Met
                565                 570                 575
Leu Asp Phe Asp Phe Ile Cys Lys Arg Glu Val Pro Ser Val Ala Ala
                580                 585                 590
Met Ile Tyr Pro Phe Gly Gly Ala His Val Gln Lys Phe Tyr Trp Gly
                595                 600                 605
Thr Lys Glu Thr Leu Leu Pro Val Tyr Thr Thr Leu Glu Glu Ala Thr
    610                 615                 620
Ala Lys Phe Pro Glu Val Asp Thr Val Val Asn Phe Ala Ser Cys Arg
625                 630                 635                 640
Ser Val Tyr Gln Ser Thr Val Asp Ile Leu Ser His Ser Asp Gln Ile
                645                 650                 655
Lys Thr Ile Ser Ile Ala Glu Gly Val Pro Glu Arg Arg Ala Arg
                660                 665                 670
Gln Ile Leu Trp Glu Ala Lys Ala Lys Asn Val Leu Val Ile Gly Pro
                675                 680                 685
Ala Thr Val Gly Gly Ile Lys Pro Gly Cys Phe Lys Ile Gly Asn Thr
    690                 695                 700
Gly Gly Met Met Asp Asn Ile Val Ser Ser Lys Leu Tyr Arg Ala Gly
705                 710                 715                 720
Ser Val Ala Tyr Val Ser Lys Ser Gly Gly Met Ser Asn Glu Leu Asn
                725                 730                 735
Asn Ile Ile Ser Arg Thr Thr Asp Gly Val Tyr Glu Gly Val Ala Ile
                740                 745                 750
Gly Gly Asp Arg Tyr Pro Gly Ser Thr Phe Ile Asp His Leu Leu Arg
                755                 760                 765
Tyr Glu Arg Asp Pro Asn Cys Lys Met Leu Val Leu Leu Gly Glu Val
    770                 775                 780
```

```
Gly Gly Val Glu Glu Tyr Lys Val Cys Glu Ala Ile Lys Asn Gly Thr
785                 790                 795                 800

Ile Arg Lys Pro Val Ile Ala Trp Cys Ile Gly Thr Cys Ala Lys Met
            805                 810                 815

Phe Ala Thr Glu Val Gln Phe Gly His Ala Gly Ala Leu Ala Gln Ser
        820                 825                 830

Asp Leu Glu Thr Ala Asp Ala Lys Asn Lys Ala Leu Arg Ala Ala Gly
    835                 840                 845

Val Val Val Pro Glu Thr Phe Glu Lys Leu Pro Leu Val Leu Ser Gln
850                 855                 860

Thr Phe Gln Thr Leu Val Lys Asn Gly Thr Ile Gln Leu Lys Pro Glu
865                 870                 875                 880

Pro Glu Thr Pro Lys Ile Pro Ile Asp Tyr Ser Trp Ala Gln Glu Leu
            885                 890                 895

Gly Leu Val Arg Lys Pro Ala Ser Phe Val Ser Thr Ile Cys Asp Asp
        900                 905                 910

Arg Gly Gln Glu Leu Leu Tyr Ala Gly Met Arg Ile Ser Asp Val Phe
    915                 920                 925

Lys Glu Asp Ile Gly Ile Gly Gly Val Leu Ser Leu Trp Phe Lys
930                 935                 940

Arg Arg Leu Pro Asp Tyr Ala Cys Lys Phe Ile Glu Met Val Leu Met
945                 950                 955                 960

Leu Thr Ala Asp His Gly Pro Ala Val Ser Gly Ala His Asn Thr Ile
            965                 970                 975

Val Thr Ala Arg Ala Gly Lys Asp Leu Val Ser Ser Leu Cys Ala Gly
        980                 985                 990

Leu Leu Thr Ile Gly Asp Arg Phe  Gly Gly Ala Leu Asp  Gly Ala Ala
    995                 1000                1005

Glu Gln  Phe Ser Ser Ala Tyr  Asp Lys Ser Leu Thr  Pro Arg Glu
    1010                1015                1020

Phe Val  Ser Val Met Arg Lys  Gln Asn Lys Leu Ile  Leu Gly Ile
    1025                1030                1035

Gly His  Lys Ile Lys Ser Arg  Thr Asn Pro Asp Leu  Arg Val Glu
    1040                1045                1050

Ile Ile  Lys Glu Tyr Ala Lys  Lys His Phe Pro Ser  Thr Pro Val
    1055                1060                1065

Leu Asp  Tyr Ala Leu Gln Val  Glu Asn Ile Thr Thr  Ser Lys Lys
    1070                1075                1080

Asp Asn  Leu Ile Leu Asn Val  Asp Gly Ala Ile Gly  Ile Leu Phe
    1085                1090                1095

Val Asp  Leu Leu Arg Asn Ser  Gly Ala Phe Thr Arg  Glu Glu Ala
    1100                1105                1110

Glu Glu  Tyr Ile Lys Ile Gly  Thr Leu Asn Gly Leu  Phe Val Leu
    1115                1120                1125

Gly Arg  Ser Ile Gly Phe Ile  Gly His Tyr Leu Asp  Gln Lys Arg
    1130                1135                1140

Leu Lys  Gln Gly Leu Tyr Arg  His Pro Trp Asp Asp  Ile Ser Tyr
    1145                1150                1155

Leu Thr  Pro Gly Asn Glu Leu  Gly Arg Thr Val Ala  Ser Leu Asp
    1160                1165                1170

Ser Ile  Asn Lys Lys Ala
    1175

<210> SEQ ID NO 12
```

```
<211> LENGTH: 1174
<212> TYPE: PRT
<213> ORGANISM: Mortierella alpina

<400> SEQUENCE: 12

Met Ser Ala Lys Ala Val Arg Glu Tyr Asp Gly Lys Leu Leu Leu Ala
1               5                   10                  15

His Trp Leu Leu Arg Thr Pro Ile Pro Ala Thr Ser Ile Ser Ala Thr
            20                  25                  30

Gly Ser Lys Phe Val Gln Pro Ala Thr Arg Leu Ala His Ile Gly Ile
        35                  40                  45

Asp Thr Ala Val Leu Asn Thr Asp Lys Thr Val Phe Asn Gln His Val
    50                  55                  60

Gln Thr Leu Leu Asp Asn Leu Glu Gln Thr His Pro Trp Leu Leu Thr
65                  70                  75                  80

Ser Lys Leu Val Ala Lys Pro Asp Gln Leu Ile Lys Arg Arg Gly Lys
                85                  90                  95

Ser Gly Leu Leu Leu Asn Ala Asp Trp Ala Glu Val Arg Thr Trp
            100                 105                 110

Ile Thr Ala His Ala Gly Lys Asp Val Val Asp Ser Val Ala Gly
        115                 120                 125

Val Leu Lys Thr Phe Leu Val Glu Pro Phe Ile Pro His Pro Ala Asn
    130                 135                 140

Thr Glu Tyr Tyr Ile Cys Ile Asn Ser Asp Arg Asp Gly Asp Asn Ile
145                 150                 155                 160

Leu Phe Thr His Glu Gly Gly Ile Glu Val Gly Asp Val Asp Ala Lys
                165                 170                 175

Ala Leu Lys Leu Gln Val Lys Val Gly Asp Thr Phe Pro Thr Thr Ala
            180                 185                 190

Ala Ile Gln Ser Ala Leu Leu Thr His Val Pro Ala Thr Lys His Asp
        195                 200                 205

Val Leu Ile Asp Phe Ile Thr Arg Leu Tyr Ala Val Tyr Val Asp Leu
    210                 215                 220

His Phe Thr Tyr Leu Glu Ile Asn Pro Leu Val Val Leu Asp Pro Thr
225                 230                 235                 240

Pro Glu His Pro Ala Gln Val Tyr Tyr Leu Asp Leu Ala Ala Lys Val
                245                 250                 255

Asp Gln Thr Ala Glu Phe Glu Ala Gly Pro Lys Trp Ala Phe Ala Arg
            260                 265                 270

Ala Pro Gln Asn Ile Gly Leu Val Ala Ala Gly Ser Gln Gly Val Asp
        275                 280                 285

Ala Gly Pro Pro Met Asp Phe Pro Ala Pro Phe Gly Arg Glu Leu Thr
    290                 295                 300

Lys Glu Glu Ala Tyr Val Gln Glu Leu Asp Ser Lys Thr Gly Ala Ser
305                 310                 315                 320

Leu Lys Leu Thr Ile Leu Asn Lys Asp Gly Arg Ile Trp Thr Met Val
                325                 330                 335

Ala Gly Gly Gly Ala Ser Val Val Tyr Ser Asp Ala Ile Ala Ala Leu
            340                 345                 350

Gly Gln Ala Asn Glu Leu Ala Asn Tyr Gly Glu Tyr Ser Gly Ala Pro
        355                 360                 365

Thr Glu Thr Gln Thr Tyr Glu Tyr Ala Lys Thr Ile Leu Asp Leu Met
    370                 375                 380

Thr Arg Ser Ala Ile Pro His Pro Leu Gly Lys Val Leu Ile Ile Gly
385                 390                 395                 400
```

```
Gly Gly Ile Ala Asn Phe Thr Asn Val Ala Ser Thr Phe Lys Gly Ile
            405                 410                 415

Val Arg Ala Leu Thr Glu Phe Lys Gln Pro Leu Ile Ala His Lys Val
            420                 425                 430

Arg Ile Phe Val Arg Arg Gly Gly Pro Asn Tyr Gln Glu Gly Leu Arg
            435                 440                 445

Ser Met Arg Gln Leu Gly Glu Thr Leu Gly Val Glu Ile Gln Val Phe
            450                 455                 460

Gly Pro Glu Thr His Ile Thr Glu Ile Val Pro Leu Ala Leu Thr Gly
465                 470                 475                 480

Lys Leu Ser Gly Leu Asn Gln Ser Gly Thr Ala Thr Pro Ser Ala His
                485                 490                 495

Leu Ser Ser Gly Asn Leu Leu Gln Asp Gln Leu Leu Gly Asn Asn Thr
                500                 505                 510

Pro Leu Asn Ala Gly Ser Arg Ala Ser Ser Pro Pro Leu Glu Asp
                515                 520                 525

Arg Met Thr Tyr Phe Gln Asp Gln Asn Ala Glu Ser Ser Glu Ser Ser
            530                 535                 540

His Asp Glu Asn Thr Pro Phe Thr Ala His Thr Arg Ser Phe Ile Tyr
545                 550                 555                 560

Gly Met Gln Pro Arg Ala Val Gln Gly Met Leu Asp Phe Asp Phe Ile
                565                 570                 575

Cys Lys Arg Glu Val Pro Ser Val Ala Ala Met Val Tyr Pro Phe Gly
                580                 585                 590

Gly Ala His Val Gln Lys Phe Tyr Trp Gly Thr Lys Glu Thr Leu Leu
                595                 600                 605

Pro Val Phe Thr Ser Leu Asp Glu Ala Val Ala Lys Tyr Pro Glu Val
                610                 615                 620

Asp Thr Val Val Asn Phe Ala Ser Cys Arg Ser Val Tyr Asp Ser Thr
625                 630                 635                 640

Arg Glu Ile Phe Lys His Ser Lys Gln Ile Arg Thr Ile Ser Ile Ile
                645                 650                 655

Ala Glu Gly Val Pro Glu Arg Arg Ala Arg Gln Ile Leu Trp Glu Ala
                660                 665                 670

Lys Glu Arg Asn Val Leu Val Ile Gly Pro Ala Thr Val Gly Gly Ile
                675                 680                 685

Lys Pro Gly Cys Phe Lys Ile Gly Asn Thr Gly Gly Met Met Asp Asn
            690                 695                 700

Ile Val Ser Ser Lys Leu Tyr Arg Ala Gly Ser Val Ala Tyr Val Ser
705                 710                 715                 720

Lys Ser Gly Gly Met Ser Asn Glu Leu Asn Asn Ile Ile Ser Arg Thr
                725                 730                 735

Thr Asp Gly Val Tyr Glu Gly Val Ala Ile Gly Gly Asp Arg Tyr Pro
            740                 745                 750

Gly Ser Thr Phe Ile Asp His Leu Leu Arg Tyr Glu Lys Asp Pro Gly
            755                 760                 765

Cys Lys Met Leu Val Leu Leu Gly Glu Val Gly Gly Val Glu Glu Tyr
            770                 775                 780

Lys Val Cys Glu Ala Ile Lys Asn Gly Ala Ile Arg Lys Pro Val Ile
785                 790                 795                 800

Ala Trp Cys Ile Gly Thr Cys Ala Lys Met Phe Ala Thr Glu Val Gln
                805                 810                 815

Phe Gly His Ala Gly Ala Leu Ala Gln Ser Asp Leu Glu Thr Ala Asp
```

```
            820                 825                 830
Ala Lys Asn Arg Ala Leu Arg Ala Ala Gly Val Ile Val Pro Glu Thr
        835                 840                 845

Phe Glu Met Leu Pro Leu Val Leu Ser Gln Thr Tyr Gln Ala Leu Val
850                 855                 860

Lys Lys Gly Val Val Ile Val Arg Ser Glu Pro Glu Thr Pro Lys Ile
865                 870                 875                 880

Pro Ile Asp Tyr Ser Trp Ala Gln Glu Leu Gly Leu Val Arg Lys Pro
                885                 890                 895

Ala Ser Phe Val Ser Thr Ile Cys Asp Asp Arg Gly Gln Glu Leu Leu
            900                 905                 910

Tyr Ala Gly Met Arg Ile Ser Asp Val Phe Lys Glu Asp Ile Gly Ile
        915                 920                 925

Gly Gly Val Leu Ser Leu Leu Trp Phe Lys Arg Arg Leu Pro Asp Tyr
    930                 935                 940

Ala Cys Lys Phe Ile Glu Met Val Leu Met Leu Thr Ala Asp His Gly
945                 950                 955                 960

Pro Ala Val Ser Gly Ala His Asn Thr Ile Val Thr Ala Arg Ala Gly
                965                 970                 975

Lys Asp Leu Val Ser Ser Leu Cys Ala Gly Leu Leu Thr Ile Gly Asp
            980                 985                 990

Arg Phe Gly Gly Ala Leu Asp Gly Ala Ala Glu Gln Phe Ser Ser Ala
        995                1000                1005

Tyr Asp Lys Ser Leu Ser Pro Arg Glu Phe Val Ser Ser Met Arg
    1010                1015                1020

Lys Gln Asn Lys Leu Ile Leu Gly Ile Gly His Lys Ile Lys Ser
    1025                1030                1035

Arg Thr Asn Pro Asp Leu Arg Val Glu Ile Ile Lys Asn Tyr Ala
    1040                1045                1050

Lys Ala His Phe Pro Ala Thr Pro Val Leu Asp Tyr Ala Leu Ala
    1055                1060                1065

Val Glu Thr Ile Thr Thr Ser Lys Lys Asp Asn Leu Ile Leu Asn
    1070                1075                1080

Val Asp Gly Ala Ile Gly Ile Leu Phe Val Asp Leu Leu Arg Asn
    1085                1090                1095

Ser Gly Ala Phe Thr Arg Glu Glu Ala Glu Glu Tyr Ile Lys Ile
    1100                1105                1110

Gly Thr Leu Asn Gly Leu Phe Val Leu Gly Arg Thr Ile Gly Phe
    1115                1120                1125

Ile Gly His Phe Leu Asp Gln Lys Arg Leu Lys Gln Gly Leu Tyr
    1130                1135                1140

Arg His Pro Trp Asp Asp Ile Ser Tyr Leu Thr Pro Gly Asn Glu
    1145                1150                1155

Leu Gly Arg Thr Val Ala Ser Leu Asp Ser Ile Asn Lys Lys Ala
    1160                1165                1170

Ala

<210> SEQ ID NO 13
<211> LENGTH: 2057
<212> TYPE: DNA
<213> ORGANISM: Mortierella alpina

<400> SEQUENCE: 13
gtcgaccatg acaagtttgc caagatgcgc gcggagcact acaagatgaa ggaggcgctt      60
```

```
caactagggc atgagctggc ggaggaagag ttgagtgcgc tggacagccc tgatcccaac     120
gatatgccag tgccgccatt accttccttt gctcaacagt cgaacgcggc taggctgtca     180
ggagaagcga atcgaacaa gctgaaggat gatcttgaaa acatggagct ttagagcttg     240
gacttggctc ttggccatgg ctatggttac tggatgtatc gagacagaca taaagggacc     300 ctgattttc accgtgtggt acctctggag cggacatttt gatgtgagag tgtatcggac     360
tgcttgttaa gttgctgcgc gtgcgatttt gtttatgttt tttcgccagc ttggacaggg     420
gtatttcaag accccgccgt tggctgtagt tgatcctctt tctcttctct tctctttttt     480
cttttccttt tttctgatgt gtctcccacc ccacaacctt ctcctcagcc cccagccgca     540
tcggtcccac cgccgcaacc catcagcaca caatggccat caaggattac cagcgcgagt     600
tcattgagtt tgccatcaag aacgaggtct tgaagtttgg agagttcacc ctcaagtccg     660
gccgtatctc cccctacttc ctgaacgcgg gtctcttcaa cactggcgct tcgctctcca     720
agatcggaaa gttctacgcc gctgccgtca acgactcggg cattgagcac gacatcatct     780
ttggccccgc ttacaagggt gtccctcttg cctgcaccac cgtcattgcc ttggccgagg     840 cccctacaa caaggacacg ccttactgct caaccgcaa ggaaaagaag gaccatggcg     900
agggtggcac gattgtcgga tcggcgttgg agggcaaggt cctggtcatt gacgatgtta     960
tcaccgccgg taccgccatc cgcgagtctg ttcaaatcat cgaggactgc aaggcccaat     1020
tggccggtgt tttggtggcg gtggatcgtc aggagactgg caagaacggc gacatgtctg     1080
ctatccagga ggtcgagagg gatttcggtg tccctgtcaa ggccattgtg accatgaccc     1140
acatcatgca gtacatggag gagaagggta cctatggcga gcacttgact cagatgcgca     1200
cctaccgcga gaagtacggt gtttaaggca aatctaaatg gataaggtc cggtataatg     1260 cggcgaggga aggttctgtt ggaaaatctc ataatgcggg gagattgaca tcggggaacg     1320
atgtgctgct catcagcagt tttcgtggac tctcgggaca ggccttcctg ggaatccaga     1380
caataatcat taataaatac caataacaat caaatcatga cttattcag tacgatagtt     1440 ggtgcatacg ctacgatcca ttaccgagcg tgatcaaggc ctcaatggcg tttgaggaca     1500
aaggaaagtc gtgggaaaga ggcgtaaaat tgagtcgtca cgaaaaaaag cacagcgccg     1560
tgtcgtcaaa ttgcgtattc atacggaata ttcggtaagg cagtctatcc tccgatgcgg     1620
gatacagact aggcgccatg agctcatcct tgccgatcgc ccgactgtac gatgatttgg     1680
tccggggaca tcgttgctga ggttcgtggc agcaaagagg aagcggtgtt tctgaggtca     1740
ccggaaattt ggagctcagc ccaaaaaaaa aaaaaaaaa aaaaaaataa tatgtttggc     1800
agcggtgagt cgggttgtct tcacatttct cttttctct ctcctttttt tcatttccac     1860 ccaccttct tccacatcca tccaccaccg cacattcacc tcacaatggc agagactctt     1920
actcaccccc ttgttcagga cggctggttc aaggagactg gcaccctctg gcccggccag     1980
gccatgaccc ttgaggtcaa ggagattctc acgttgaaa agtcgctgtt ccaggacgtg     2040
ctcgtcttcc agtcgac                                                   2057

<210> SEQ ID NO 14
<211> LENGTH: 1011
<212> TYPE: DNA
<213> ORGANISM: Mortierella alpina

<400> SEQUENCE: 14
atgaccatca agatcggcat caacggtttc ggacgcatcg tcgtctcgt gctccgtgcg     60 gctctcgcca acaagaaggt tgaggttgtg gccgtcaacg atcccttcat tgatctggcc     120
```

| | |
|---|---|
| tacatggttt acatgttcaa gtacgactcg acccacggac gctacaaggg caaggtcgag | 180 |
| gccaaggatg gacacttggt tgtcgatggc cacaagattg ctgtttacga caagagaaac | 240 |
| cctgacgaga ttccctgggg caccaatggc gctgaatacg tcgttgagtc gactggtgtc | 300 |
| ttcactacga tcgaaaaggc gtccctgcat ttgaagggtg gagccaagaa ggttgtcatc | 360 |
| tctgccccct ctgcagatgc acccatgttt gtgtgcggag tcaacctgga ctcttacaag | 420 |
| cccgaataca aggtggtttc gaacgcctca tgcacaacca actgcttggc tcctctggcc | 480 |
| aagatcatcc acgacaactt tggcatcacc gaagccctca tgaccaccgt ccacgccacc | 540 |
| acggccaccc agaagaccgt tgacggaccc tcggccaagg actggcgcgg tggacgtggt | 600 |
| gctgccgcca acatcatccc ctcctcgacc ggcgcagcca aggctgtggg caaggtgatc | 660 |
| ccgtccttga acggcaagct gactggtatg cattccgtg tgcctactcc cgacgtgtcg | 720 |
| gttgtggatc tgacggcacg cttgtccaag cccgcgacct atgaccagat caaggctgtg | 780 |
| atcaagaagg cagccgaggg cgagatgaag ggcattatgg gctacactga ggatgatgtc | 840 |
| gtgtcgactg acttcattgg agacacgcac tcgtccatct tgatgccaa ggccggtatc | 900 |
| gcgctttcgg atacgtttgt caagttggtg tcctggtacg acaatgagtt tggatacagc | 960 |
| acccgctgtg tcgagttgat cgagttcatg gccaagaagg atcatgctta a | 1011 |

<210> SEQ ID NO 15
<211> LENGTH: 3005
<212> TYPE: DNA
<213> ORGANISM: Mortierella alpina

<400> SEQUENCE: 15

| | |
|---|---|
| gatcacgtcg ggtgatgagt tgctgttgac cgagatgatt ttcaatggcg ccttcaacga | 60 |
| cctgaaggtg gagcagacag tggccttgct aagctgtttt gtgtttcagg aaaagtcgga | 120 |
| cactgtcccg tcccttaagg aagagttggc gacaccactg agactgatgc aggaggcagc | 180 |
| ccgcaggatt gccaaggttt cgcaagactg caagctcacg gtggacgagg aagagtacgt | 240 |
| ccagtcgttc cgctctgagc tcatggatgt tgtctacgct tgggctaatg taagttgcaa | 300 |
| agtgtgatca gggtacgatg taagaggaag gaaaaaggag tggtggatga ctcatttatt | 360 |
| tcacgacatg ttctgcgccg caaaaatagg gtgcaaggtt ctcacagatc tgcaagatga | 420 |
| cggatgtgtt tgagggatcc attatccgtg cattccgtcg gttggaggag ttgttgcggc | 480 |
| agatggcttc ggccgccaag agcatcggta acaccgagtt ggagtccaag ttcgcagcgg | 540 |
| gcattgtttg catcaagcgc gacattatct ttgcatcgtc gctgtacctt taagtggaca | 600 |
| atctgccacc cttgcatacg ttcttatatc ataaaataaa agtttacacg gcccagtgtc | 660 |
| cgatctagca ttgcattcag cagttatcag tttctcggtg agatgtcgta tttaggacct | 720 |
| ctcctcagaa tgggtgaagc cgaatgttca ctctaacgta cgccgaaccc acgtacgcag | 780 |
| ccgccttgag acatgctgcg ttgcgcatat atttattagg gtcgtcgttt gctccttctc | 840 |
| ttttctttct tcatccacac cactgcaccc tcacaaacac ccacacacac accacacatt | 900 |
| caacatcatg accatcaaga tcggcatcaa cgggtaagca cttccaccct tcctctgcac | 960 |
| cctctccctc tcttggtcaa gccgcgcctg cagctgcagc tctcgccctt tcgacgctc | 1020 |
| gagccaaaag acgggcgttg agggagcaaa aatacacaca aaatcaccat ccgcactccc | 1080 |
| tccttttat cccacgcctc tctttgccga cagcctcgtt ctctcgcagt acatctaact | 1140 |
| gtcgttgtgc ccactctgtc ttccatgcca tgaacttagt ttcggacgca tcggtcgtct | 1200 |
| cgtgctccgt gcggctctcg ccaacaagaa ggttgaggtt gtggccgtca acgatccctt | 1260 |

```
cattgatctg gcctacatgg taagaaagga cagtatccaa cgccgccgcg ttctcatctc    1320
tctcatcact atgatgacat cgaaaggctg gttttgtggc agctctgtgc accagggatg    1380
catgggcccg ataagaaaca caattctcac gtcacgaaaa tccttttatt gttttcccga    1440
ctcccatgtt aggtttacat gttcaagtac gactcgaccc acggacgcta caagggcaag    1500
gtcgaggcca aggatggaca cttggttgtc gatggccaca agattgctgt ttacgacaag    1560
taagtgttga aatcctctcc tcgaaaaact gttgaagttt cttttttggc cgagctcagc    1620
atgaactgtc attctaggtc cagttgagac gacttgaaaa ctatatttgc aattcttgca    1680
ctgaccccct aaccctcttt ttttttttgcg cgatgtagga gaaaccctga cgagattccc    1740
tggggcacca atggcgctga atacgtcgtt gagtcgactg gtgtcttcac tacgatcgaa    1800
aaggcgtccc tgcatttgaa gggtggagcc aagaaggttg tcatctctgc ccctctgca    1860 gatgcaccca tgtttgtgtg cggagtcaac ctggactctt acaagcccga atacaaggtg    1920
gtttcgaacg cctcatgcac aaccaactgc ttggctcctc tggccaagat catccacgac    1980
aactttggca tcaccgaagc cctcatgacc accgtccacg ccaccacggc cacccagaag    2040
accgttgacg gaccctcggc caaggactgg cgcggtggac gtggtgctgc cgccaacatc    2100
atcccctcct cgaccggcgc agccaaggct gtgggcaagg tgatcccgtc cttgaacggc    2160
aagctgactg gtatggcatt ccgtgtgcct actcccgacg tgtcggttgt ggatctgacg    2220
gcacgcttgt ccaagcccgc gacctatgac cagatcaagg ctgtgatcaa gaaggcagcc    2280
gagggcgaga tgaagggcat tatgggctac actgaggatg atgtcgtgtc gactgacttc    2340
attggagaca cgcactcgtc catctttgat gccaaggccg gtatcgcgct ttcggatacg    2400
tttgtcaagt tggtgtcctg gtacgacaat gagtttggat acagcacccg ctgtgtcgag    2460
ttgatcgagt tcatggccaa gaaggatcat gcttaagaaa agggagtgaa tcgcataggg    2520
gagatcgaac ccatctttct ttgtcaaaaa tcaccaccgt tatttgcatg caagcagaac    2580
ttgaaatcat cctcgcgcaa agtcattctc ttgagaaggg tcaatgggaa aaaacaatca    2640
aacagataag agtctttgat tgttgttgta aataaaaaaa ccaggttttt tgcttttagt    2700
tcttttgaga aaatgagatg gggagtgtgt aacgatggga cgatgatgat ggtgatggta    2760
tgcgagtgaa gagaggtgta tgtgatgtct atatatataa aaaaagccag gtttgattta    2820
aaccaaggcg atggtgatgt ctccactgct gttcttggcc atgaccagac cattgccttg    2880
gccgatcgtg ccaatgacct ccttggtgac agccacgtcc ttgtcgtcgt ccttcttccg    2940
ccgctccttc tcggagcggg tcgtgtgcac ggaccgcgac tctgagaagg acccgtgcat    3000
ggatc                                                                3005

<210> SEQ ID NO 16
<211> LENGTH: 907
<212> TYPE: DNA
<213> ORGANISM: Mortierella alpina

<400> SEQUENCE: 16
gatcacgtcg ggtgatgagt tgctgttgac cgagatgatt ttcaatggcg ccttcaacga      60
cctgaaggtg gagcagacag tggccttgct aagctgtttt gtgtttcagg aaaagtcgga    120
cactgtcccg tcccttaagg aagagttggc gacaccactg agactgatgc aggaggcagc    180
ccgcaggatt gccaaggttt cgcaagactg caagctcacg gtggacgagg aagagtacgt    240
ccagtcgttc cgctctgagc tcatggatgt tgtctacgct tgggctaatg taagttgcaa    300
agtgtgatca gggtacgatg taagaggaag gaaaaaggag tggtggatga ctcatttatt    360
```

```
tcacgacatg ttctgcgccg caaaaatagg gtgcaaggtt ctcacagatc tgcaagatga      420
cggatgtgtt tgagggatcc attatccgtg cattccgtcg gttggaggag ttgttgcggc      480
agatggcttc ggccgccaag agcatcggta acaccgagtt ggagtccaag ttcgcagcgg      540
gcattgtttg catcaagcgc gacattatct ttgcatcgtc gctgtacctt aagtggaca       600 atctgccacc cttgcatacg ttcttatatc ataaaataaa agtttacacg gcccagtgtc      660
cgatctagca ttgcattcag cagttatcag tttctcggtg agatgtcgta tttaggacct      720
ctcctcagaa tgggtgaagc cgaatgttca ctctaacgta cgccgaaccc acgtacgcag      780
ccgccttgag acatgctgcg ttgcgcatat atttattagg gtcgtcgttt gctccttctc      840
ttttctttct tcatccacac cactgcaccc tcacaaacac ccacacacac accacacatt      900
caacatc                                                               907

<210> SEQ ID NO 17
<211> LENGTH: 512
<212> TYPE: DNA
<213> ORGANISM: Mortierella alpina

<400> SEQUENCE: 17
taagaaaagg gagtgaatcg catagggag atcgaaccca tctttctttg tcaaaaatca       60
ccaccgttat ttgcatgcaa gcagaacttg aaatcatcct cgcgcaaagt cattctcttg      120
agaagggtca atgggaaaaa acaatcaaac agataagagt ctttgattgt tgttgtaaat     180
aaaaaaacca ggtttttgc ttttagttct tttgagaaaa tgagatgggg agtgtgtaac      240
gatgggacga tgatgatggt gatggtatgc gagtgaagag aggtgtatgt gatgtctata     300
tatataaaaa aagccaggtt tgatttaaac caaggcgatg gtgatgtctc cactgctgtt     360
cttggccatg accagaccat tgccttggcc gatcgtgcca atgacctcct tggtgacagc     420
cacgtccttg tcgtcgtcct tcttccgccg ctccttctcg gagcgggtcg tgtgcacgga      480
ccgcgactct gagaaggacc cgtgcatgga tc                                   512

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gataccgtcg tcaactttgc ctc                                             23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
catcttgcag ttggggtccc gct                                             23

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 20
gttgacaccg tggtgaactt tgcc                                          24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcatcttgca cccggatcct tctc                                          24

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gaattctcta gaatgtctgc taaagccgtt cgcg                               34

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aagcttgtcg acttaggcct tcttgttgat cg                                 32

<210> SEQ ID NO 24
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atgaccatca agatcggcat ca                                            22

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ttaagcatga tccttcttgg cc                                            22

<210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
```

```
aagcttgatc acgtcgggtg atgagttgct gttgac                              36

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaattcgatg ttgaatgtgt ggtgtg                                         26

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tctagataag aaagggagt gaatcg                                          26

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcggccgcga tccatgcacg ggtccttc                                       28

<210> SEQ ID NO 30
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ctagcgcggc cgcctcgaga agcttcccgg ggcatgcctg cagtctagag                50

<210> SEQ ID NO 31
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
aattctctag actgcaggca tgccccggga agcttctcga ggcggccgcg                50

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcgtcatccc caccactgtt                                                20
```

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 33
gctggcggga ggagtgccag cacg                                            24

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 34
cacaccacac attcaacatc                                                 20

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 35
cgaagccggc aaaggcggca gtcg                                            24

<210> SEQ ID NO 36
<211> LENGTH: 1152
<212> TYPE: PRT
<213> ORGANISM: Ustilago maydis

<400> SEQUENCE: 36

Met Ser Ser Lys Ala Ile Arg Glu Phe Asp Ala Lys Leu Leu Val Asn
1               5                   10                  15

Tyr Trp Leu Pro Arg Ser Pro Leu Ala His Ala Asp Leu Lys Val Asn
            20                  25                  30

Ala Asp Phe Val Ala Pro Ala Pro Lys Val Ala Gln Ile Ala Trp Asp
        35                  40                  45

Pro Val Thr Asn Ser Ile Thr Asp Ala Ser Gln Leu Pro Ala Trp Val
    50                  55                  60

Gln Ser Ser Lys Leu Val Ala Lys Pro Asp Gln Leu Ile Lys Arg Arg
65                  70                  75                  80

Gly Lys Ala Gly Leu Leu Lys Leu Asn Cys Asp Trp Ala Asp Ala Lys
                85                  90                  95

Thr Trp Ile Gln Glu Arg Ala Gly Lys Ala Gln Lys Val Glu Thr Val
            100                 105                 110

Thr Gly Thr Leu Asn Asn Phe Ile Val Glu Pro Phe Cys Pro His Pro
        115                 120                 125

Ala Asp Thr Glu Phe Tyr Val Cys Ile Asn Ser Ala Arg Glu Gly Asp
    130                 135                 140

Trp Ile Leu Phe Thr His Glu Gly Gly Val Asp Val Gly Asp Val Asp
145                 150                 155                 160

Ala Lys Ala Leu Lys Leu Leu Ile Pro Ala Asp Pro Ala Ala Pro Phe
                165                 170                 175

```
Pro Lys Arg Glu Glu Trp Thr Ser Thr Leu Leu Gly Val Pro Ala
            180                 185                 190
Ala Lys Arg Glu Val Leu Thr Asp Phe Leu Ile Arg Leu Tyr Ser Val
        195                 200                 205
Tyr Val Asp Leu His Phe Ala Tyr Leu Glu Ile Asn Pro Leu Val Ala
210                 215                 220
Thr Asp Asp Gly Gln Ile Ala Tyr Leu Asp Met Ala Ala Lys Leu Asp
225                 230                 235                 240
Gln Thr Ala Asp Phe Ile Cys Gly Pro Lys Trp Ala Ile Ala Arg Asp
                245                 250                 255
Pro Ser Ile Tyr Leu Gly Ala Ser Ala Gly Ala Ser Gly Asn Lys Gly
            260                 265                 270
Glu Asp Arg Gly Pro Pro Met Tyr Trp Pro Ala Pro Phe Gly Arg Asp
        275                 280                 285
Leu Thr Lys Glu Glu Ala Tyr Ile Ala Lys Leu Asp Ala Gly Thr Gly
    290                 295                 300
Ala Ser Leu Lys Leu Thr Val Leu Asn Pro Thr Gly Arg Ile Trp Thr
305                 310                 315                 320
Met Val Ala Gly Gly Ala Ser Val Val Tyr Ser Asp Ala Ile Ala
                325                 330                 335
Ala His Gly Tyr Ala His Glu Leu Ala Asn Tyr Gly Glu Tyr Ser Gly
            340                 345                 350
Ala Pro Ser Glu Gly Gln Thr Phe Glu Tyr Ala Lys Thr Leu Leu Asp
        355                 360                 365
Leu Met Thr Arg Gly Glu Val Asn Pro Gln Gly Lys Leu Leu Ile Ile
    370                 375                 380
Gly Gly Gly Ile Ala Asn Phe Thr Asn Val Ala Ser Thr Phe Lys Gly
385                 390                 395                 400
Ile Ile Arg Ala Leu Lys Glu Tyr Lys Leu Ser Leu Ala Lys His Gly
                405                 410                 415
Val Arg Ile Phe Val Arg Arg Gly Gly Pro Asn Tyr Gln Glu Gly Leu
            420                 425                 430
Lys Ala Met Arg Leu Leu Gly Glu Asp Leu Gly Val Glu Ile Gln Val
        435                 440                 445
Phe Gly Pro Glu Thr His Ile Thr Asp Ile Val Pro Leu Ala Leu Gly
    450                 455                 460
Val Lys Thr Phe Glu Glu Val Thr Leu Ala Ser Gln Gln Asn Thr
465                 470                 475                 480
Leu Pro Ser Gly Ala Ala Thr Pro Ala His Gly Ala Ala Asn Gly Thr
                485                 490                 495
Lys Ala Glu Asn Lys Ala Ile Gly Thr Val Asp His Asn Thr Gly Glu
            500                 505                 510
Arg Val Gln Pro Gln Asp Gln Ile Val His Phe Gly Ala Gly Ser Thr
        515                 520                 525
Thr Gly Glu Arg Pro Ala Tyr Arg Pro Phe Asp Ala Asn Thr Arg Ser
    530                 535                 540
Leu Val Phe Gly Leu Gln Pro Arg Ala Ile Gln Gly Met Leu Asp Phe
545                 550                 555                 560
Asp Phe Ser Cys Gly Arg Lys Thr Pro Ser Val Ala Ala Met Ile Tyr
                565                 570                 575
Pro Phe Gly Gly His His Ile Gln Lys Phe Tyr Trp Gly Thr Lys Glu
            580                 585                 590
Thr Leu Leu Pro Val Tyr Thr Ser Ile Lys Glu Ala Val Ala Lys His
```

```
                595                 600                 605
    Pro Asp Ala Asp Val Val Asn Phe Ala Ser Ser Arg Ser Val Tyr
        610                 615                 620

Ser Ser Thr Leu Glu Val Leu Asp Cys Pro Gln Ile Arg Ala Leu Ala
    625                 630                 635                 640

Leu Ile Ala Glu Gly Val Pro Glu Arg His Ala Arg Glu Ile Leu His
                    645                 650                 655

Arg Ala Glu Lys Ala Gly Val Leu Ile Ile Gly Pro Ala Thr Val Gly
                660                 665                 670

Gly Ile Lys Pro Gly Cys Phe Arg Ile Gly Asn Ser Gly Gly Met Met
            675                 680                 685

Asp Asn Ile Leu Ala Ser Lys Leu Tyr Arg Pro Gly Ser Val Gly Tyr
        690                 695                 700

Val Ser Lys Ser Gly Gly Met Ser Asn Glu Leu Asn Asn Ile Leu Ser
    705                 710                 715                 720

Ile Thr Thr Asn Gly Thr Tyr Glu Gly Ile Ala Ile Gly Gly Asp Arg
                    725                 730                 735

Tyr Pro Gly Thr Thr Phe Ile Asp His Leu Leu Arg Tyr Glu Gln Asp
                740                 745                 750

Pro Glu Cys Lys Met Leu Val Leu Leu Gly Glu Val Gly Gly Ile Glu
            755                 760                 765

Glu Tyr Arg Val Ile Glu Ala Val Lys Lys Gly Thr Ile Lys Lys Pro
        770                 775                 780

Ile Ile Ala Trp Ala Ile Gly Thr Cys Ala Lys Met Phe Thr Thr Glu
    785                 790                 795                 800

Val Gln Phe Gly His Ala Gly Ser Met Ala Asn Ser Asp Met Glu Thr
                    805                 810                 815

Ala Ser Ala Lys Asn Ala Ala Met Lys Ala Ala Gly Phe Ile Val Pro
                820                 825                 830

Asp Thr Phe Glu Asp Leu Pro Ala Val Ile Arg Glu Val Tyr Asn Lys
            835                 840                 845

Leu Val Ala Ser Gly Thr Ile Gln Pro Lys Pro Glu Arg Pro Ala Pro
    850                 855                 860

Ala Ile Pro Val Asp Tyr Lys Trp Ala Gln Glu Leu Gly Met Val Arg
    865                 870                 875                 880

Lys Pro Ala Ala Phe Ile Ser Thr Ile Ser Asp Glu Arg Gly Ser Glu
                    885                 890                 895

Leu Met Tyr Ser Gly Val Lys Ile Ser Glu Val Phe Glu Ser Gly Met
                900                 905                 910

Gly Ile Gly Gly Val Ile Ser Leu Leu Trp Phe Lys Arg Arg Leu Pro
            915                 920                 925

Asp Tyr Cys Thr Lys Phe Ile Glu Met Ala Leu Met Leu Thr Ala Asp
        930                 935                 940

His Gly Pro Ala Val Ser Gly Ala Met Asn Thr Ile Ile Thr Ser Arg
    945                 950                 955                 960

Ala Gly Lys Asp Leu Ile Ser Ser Leu Val Ser Gly Leu Leu Thr Ile
                    965                 970                 975

Gly Asp Arg Phe Gly Gly Ala Leu Asp Asp Ala Ala Thr Glu Phe Ser
                980                 985                 990

Ser Ala Tyr Asp Arg Gly Met Thr Ala Arg Glu Phe Val Asp Ser Met
            995                 1000                1005

Arg Lys Ala Asn Lys Leu Ile Pro Gly Ile Gly His Lys Ile Lys
        1010                1015                1020
```

-continued

Ser Val Ser Asn Pro Asp Tyr Arg Val Gln Val Lys Glu Phe
    1025            1030            1035

Val Leu Thr Asn Phe Pro Ser His Lys Met Leu Asp Tyr Ala Leu
    1040            1045            1050

Ala Val Glu Lys Val Thr Ala Lys Lys Asp Thr Leu Ile Leu
    1055            1060            1065

Asn Val Asp Gly Cys Leu Ala Val Cys Phe Val Asp Leu Leu Arg
    1070            1075            1080

Asp Ser Gly Ala Phe Thr Ile Glu Glu Ala Arg Asp Tyr Leu Ser
    1085            1090            1095

Tyr Gly Phe Leu Asn Gly Ile Phe Thr Leu Gly Arg Ser Ile Gly
    1100            1105            1110

Phe Ile Gly His His Ile Asp Gln Lys Arg Leu Lys Ala Gly Leu
    1115            1120            1125

Tyr Arg His Pro Ala Asp Asp Phe His Ile Glu Met Ala Thr Pro
    1130            1135            1140

Ala Arg Val Met Gly Thr Leu Lys Lys
    1145            1150

<210> SEQ ID NO 37
<211> LENGTH: 1091
<212> TYPE: PRT
<213> ORGANISM: Mus musculus

<400> SEQUENCE: 37

Met Ser Ala Lys Ala Ile Ser Glu Gln Thr Gly Lys Glu Leu Leu Tyr
1               5                   10                  15

Lys Tyr Ile Cys Thr Thr Ser Ala Ile Gln Asn Arg Phe Lys Tyr Ala
            20                  25                  30

Arg Val Thr Pro Asp Thr Asp Trp Ala His Leu Leu Gln Asp His Pro
        35                  40                  45

Trp Leu Leu Ser Gln Ser Leu Val Val Lys Pro Asp Gln Leu Ile Lys
    50                  55                  60

Arg Arg Gly Lys Leu Gly Leu Val Gly Val Asn Leu Ser Leu Asp Gly
65                  70                  75                  80

Val Lys Ser Trp Leu Lys Pro Arg Leu Gly His Glu Ala Thr Val Gly
                85                  90                  95

Lys Ala Lys Gly Phe Leu Lys Asn Phe Leu Ile Glu Pro Phe Val Pro
            100                 105                 110

His Ser Gln Ala Glu Glu Phe Tyr Val Cys Ile Tyr Ala Thr Arg Glu
        115                 120                 125

Gly Asp Tyr Val Leu Phe His His Glu Gly Gly Val Asp Val Gly Asp
    130                 135                 140

Val Asp Ala Lys Ala Gln Lys Leu Leu Val Gly Val Asp Glu Lys Leu
145                 150                 155                 160

Asn Thr Glu Asp Ile Lys Arg His Leu Leu Val His Ala Pro Glu Asp
                165                 170                 175

Lys Lys Glu Val Leu Ala Ser Phe Ile Ser Gly Leu Phe Asn Phe Tyr
            180                 185                 190

Glu Asp Leu Tyr Phe Thr Tyr Leu Glu Ile Asn Pro Leu Val Val Thr
        195                 200                 205

Lys Asp Gly Val Tyr Ile Leu Asp Leu Ala Ala Lys Val Asp Ala Thr
    210                 215                 220

Ala Asp Tyr Ile Cys Lys Val Lys Trp Gly Asp Ile Glu Phe Pro Pro
225                 230                 235                 240

-continued

```
Pro Phe Gly Arg Glu Ala Tyr Pro Glu Glu Ala Tyr Ile Ala Asp Leu
            245                 250                 255

Asp Ala Lys Ser Gly Ala Ser Leu Lys Leu Thr Leu Leu Asn Pro Lys
        260                 265                 270

Gly Arg Ile Trp Thr Met Val Ala Gly Gly Ala Ser Val Val Tyr
    275                 280                 285

Ser Asp Thr Ile Cys Asp Leu Gly Val Asn Glu Leu Ala Asn Tyr
290                 295                 300

Gly Glu Tyr Ser Gly Ala Pro Ser Glu Gln Gln Thr Tyr Asp Tyr Ala
305                 310                 315                 320

Lys Thr Ile Leu Ser Leu Met Thr Arg Glu Lys His Pro Glu Gly Lys
            325                 330                 335

Ile Leu Ile Ile Gly Gly Ser Ile Ala Asn Phe Thr Asn Val Ala Ala
            340                 345                 350

Thr Phe Lys Gly Ile Val Arg Ala Ile Arg Asp Tyr Gln Gly Pro Leu
            355                 360                 365

Lys Glu His Glu Val Thr Ile Phe Val Arg Arg Gly Gly Pro Asn Tyr
    370                 375                 380

Gln Glu Gly Leu Arg Val Met Gly Glu Val Gly Lys Thr Thr Gly Ile
385                 390                 395                 400

Pro Ile His Val Phe Gly Thr Glu Thr His Met Thr Ala Ile Val Gly
                405                 410                 415

Met Ala Leu Gly His Arg Pro Ile Pro Asn Gln Pro Pro Thr Ala Ala
                420                 425                 430

His Thr Ala Asn Phe Leu Leu Asn Ala Ser Gly Ser Thr Ser Thr Pro
            435                 440                 445

Ala Pro Ser Arg Thr Ala Ser Phe Ser Glu Ser Arg Ala Asp Glu Val
        450                 455                 460

Ala Pro Ala Lys Lys Ala Lys Pro Ala Met Pro Gln Gly Lys Ser Ala
465                 470                 475                 480

Thr Leu Phe Ser Arg His Thr Lys Ala Ile Val Trp Gly Met Gln Thr
                485                 490                 495

Arg Ala Val Gln Gly Met Leu Asp Phe Asp Tyr Val Cys Ser Arg Asp
            500                 505                 510

Glu Pro Ser Val Ala Ala Met Val Tyr Pro Phe Thr Gly Asp His Lys
        515                 520                 525

Gln Lys Phe Tyr Trp Gly His Lys Glu Ile Leu Ile Pro Val Phe Lys
    530                 535                 540

Asn Met Ala Asp Ala Met Lys Lys His Pro Glu Val Asp Val Leu Ile
545                 550                 555                 560

Asn Phe Ala Ser Leu Arg Ser Ala Tyr Asp Ser Thr Met Glu Thr Met
                565                 570                 575

Asn Tyr Ala Gln Ile Arg Thr Ile Ala Ile Ala Glu Gly Ile Pro
            580                 585                 590

Glu Ala Leu Thr Arg Lys Leu Ile Lys Lys Ala Asp Gln Lys Gly Val
        595                 600                 605

Thr Ile Ile Gly Pro Ala Thr Val Gly Gly Ile Lys Pro Gly Cys Phe
    610                 615                 620

Lys Ile Gly Asn Thr Gly Gly Met Leu Asp Asn Ile Leu Ala Ser Lys
625                 630                 635                 640

Leu Tyr Arg Pro Gly Ser Val Ala Tyr Val Ser Arg Ser Gly Gly Met
                645                 650                 655

Ser Asn Glu Leu Asn Asn Ile Ile Ser Arg Thr Thr Asp Gly Val Tyr
            660                 665                 670
```

```
Glu Gly Val Ala Ile Gly Gly Asp Arg Tyr Pro Gly Ser Thr Phe Met
            675                 680                 685
Asp His Val Leu Arg Tyr Gln Asp Thr Pro Gly Val Lys Met Ile Val
        690                 695                 700
Val Leu Gly Glu Ile Gly Gly Thr Glu Glu Tyr Lys Ile Cys Arg Gly
705                 710                 715                 720
Ile Lys Glu Gly Arg Leu Thr Lys Pro Val Val Cys Trp Cys Ile Gly
                725                 730                 735
Thr Cys Ala Thr Met Phe Ser Ser Glu Val Gln Phe Gly His Ala Gly
            740                 745                 750
Ala Cys Ala Asn Gln Ala Ser Glu Thr Ala Val Ala Lys Asn Gln Ala
        755                 760                 765
Leu Lys Glu Ala Gly Val Phe Val Pro Arg Ser Phe Asp Glu Leu Gly
    770                 775                 780
Glu Ile Ile Gln Ser Val Tyr Glu Asp Leu Val Ala Lys Gly Ala Ile
785                 790                 795                 800
Val Pro Ala Gln Glu Val Pro Pro Thr Val Pro Met Asp Tyr Ser
                805                 810                 815
Trp Ala Arg Glu Leu Gly Leu Ile Arg Lys Pro Ala Ser Phe Met Thr
            820                 825                 830
Ser Ile Cys Asp Glu Arg Gly Gln Glu Leu Ile Tyr Ala Gly Met Pro
        835                 840                 845
Ile Thr Glu Val Phe Lys Glu Glu Met Gly Ile Gly Gly Val Leu Gly
    850                 855                 860
Leu Leu Trp Phe Gln Arg Arg Leu Pro Lys Tyr Ser Cys Gln Phe Ile
865                 870                 875                 880
Glu Met Cys Leu Met Val Thr Ala Asp His Gly Pro Ala Val Ser Gly
                885                 890                 895
Ala His Asn Thr Ile Ile Cys Ala Arg Ala Gly Lys Asp Leu Val Ser
            900                 905                 910
Ser Leu Thr Ser Gly Leu Leu Thr Ile Gly Asp Arg Phe Gly Gly Ala
        915                 920                 925
Leu Asp Ala Ala Ala Lys Met Phe Ser Lys Ala Phe Asp Ser Gly Ile
    930                 935                 940
Ile Pro Met Glu Phe Val Asn Lys Met Lys Lys Glu Gly Lys Leu Ile
945                 950                 955                 960
Met Gly Ile Gly His Arg Val Lys Ser Ile Asn Asn Pro Asp Met Arg
                965                 970                 975
Val Gln Ile Leu Lys Asp Phe Val Lys Gln His Phe Pro Ala Thr Pro
            980                 985                 990
Leu Leu Asp Tyr Ala Leu Glu Val Glu Lys Ile Thr Thr Ser Lys Lys
        995                 1000                1005
Pro Asn Leu Ile Leu Asn Val Asp Gly Phe Ile Gly Val Ala Phe
    1010                1015                1020
Val Asp Met Leu Arg Asn Cys Gly Ser Phe Thr Arg Glu Glu Ala
    1025                1030                1035
Asp Glu Tyr Val Asp Ile Gly Ala Leu Asn Gly Ile Phe Val Leu
    1040                1045                1050
Gly Arg Ser Met Gly Phe Ile Gly His Tyr Leu Asp Gln Lys Arg
    1055                1060                1065
Leu Lys Gln Gly Leu Tyr Arg His Pro Trp Asp Asp Ile Ser Tyr
    1070                1075                1080
Val Leu Pro Glu His Met Ser Met
```

```
                       1085                1090

<210> SEQ ID NO 38
<211> LENGTH: 1101
<212> TYPE: PRT
<213> ORGANISM: Homo sapiens

<400> SEQUENCE: 38

Met Ser Ala Lys Ala Ile Ser Glu Gln Thr Gly Lys Glu Leu Leu Tyr
1               5                   10                  15

Lys Phe Ile Cys Thr Thr Ser Ala Ile Gln Asn Arg Phe Lys Tyr Ala
            20                  25                  30

Arg Val Thr Pro Asp Thr Asp Trp Ala Arg Leu Leu Gln Asp His Pro
        35                  40                  45

Trp Leu Leu Ser Gln Asn Leu Val Val Lys Pro Asp Gln Leu Ile Lys
    50                  55                  60

Arg Arg Gly Lys Leu Gly Leu Val Gly Val Asn Leu Thr Leu Asp Gly
65                  70                  75                  80

Val Lys Ser Trp Leu Lys Pro Arg Leu Gly Gln Glu Ala Thr Val Gly
                85                  90                  95

Lys Ala Thr Gly Phe Leu Lys Asn Phe Leu Ile Glu Pro Phe Val Pro
            100                 105                 110

His Ser Gln Ala Glu Glu Phe Tyr Val Cys Ile Tyr Ala Thr Arg Glu
        115                 120                 125

Gly Asp Tyr Val Leu Phe His His Glu Gly Gly Val Asp Val Gly Asp
130                 135                 140

Val Asp Ala Lys Ala Gln Lys Leu Leu Val Gly Val Asp Glu Lys Leu
145                 150                 155                 160

Asn Pro Glu Asp Ile Lys Lys His Leu Leu Val His Ala Pro Glu Asp
                165                 170                 175

Lys Lys Glu Ile Leu Ala Ser Phe Ile Ser Gly Leu Phe Asn Phe Tyr
            180                 185                 190

Glu Asp Leu Tyr Phe Thr Tyr Leu Glu Ile Asn Pro Leu Val Val Thr
        195                 200                 205

Lys Asp Gly Val Tyr Val Leu Asp Leu Ala Ala Lys Val Asp Ala Thr
    210                 215                 220

Ala Asp Tyr Ile Cys Lys Val Lys Trp Gly Asp Ile Glu Phe Pro Pro
225                 230                 235                 240

Pro Phe Gly Arg Glu Ala Tyr Pro Glu Glu Ala Tyr Ile Ala Asp Leu
                245                 250                 255

Asp Ala Lys Ser Gly Ala Ser Leu Lys Leu Thr Leu Leu Asn Pro Lys
            260                 265                 270

Gly Arg Ile Trp Thr Met Val Ala Gly Gly Ala Ser Val Val Tyr
            275                 280                 285

Ser Asp Thr Ile Cys Asp Leu Gly Gly Val Asn Glu Leu Ala Asn Tyr
290                 295                 300

Gly Glu Tyr Ser Gly Ala Pro Ser Glu Gln Gln Thr Tyr Asp Tyr Ala
305                 310                 315                 320

Lys Thr Ile Leu Ser Leu Met Thr Arg Glu Lys His Pro Asp Gly Lys
            325                 330                 335

Ile Leu Ile Ile Gly Gly Ser Ile Ala Asn Phe Thr Asn Val Ala Ala
        340                 345                 350

Thr Phe Lys Gly Ile Val Arg Ala Ile Arg Asp Tyr Gln Gly Pro Leu
    355                 360                 365

Lys Glu His Glu Val Thr Ile Phe Val Arg Arg Gly Gly Pro Asn Tyr
```

```
            370                 375                 380
Gln Glu Gly Leu Arg Val Met Gly Glu Val Gly Lys Thr Thr Gly Ile
385                 390                 395                 400

Pro Ile His Val Phe Gly Thr Glu Thr His Met Thr Ala Ile Val Gly
                405                 410                 415

Met Ala Leu Gly His Arg Pro Ile Pro Asn Gln Pro Pro Thr Ala Ala
                420                 425                 430

His Thr Ala Asn Phe Leu Leu Asn Ala Ser Gly Ser Thr Ser Thr Pro
                435                 440                 445

Ala Pro Ser Arg Thr Ala Ser Phe Ser Glu Ser Arg Ala Asp Glu Val
450                 455                 460

Ala Pro Ala Lys Lys Ala Lys Pro Ala Met Pro Gln Asp Ser Val Pro
465                 470                 475                 480

Ser Pro Arg Ser Leu Gln Gly Lys Ser Thr Thr Leu Phe Ser Arg His
                485                 490                 495

Thr Lys Ala Ile Val Trp Gly Met Gln Thr Arg Ala Val Gln Gly Met
                500                 505                 510

Leu Asp Phe Asp Tyr Val Cys Ser Arg Asp Glu Pro Ser Val Ala Ala
                515                 520                 525

Met Val Tyr Pro Phe Thr Gly Asp His Lys Gln Lys Phe Tyr Trp Gly
530                 535                 540

His Lys Glu Ile Leu Ile Pro Val Phe Lys Asn Met Ala Asp Ala Met
545                 550                 555                 560

Arg Lys His Pro Glu Val Asp Val Leu Ile Asn Phe Ala Ser Leu Arg
                565                 570                 575

Ser Ala Tyr Asp Ser Thr Met Glu Thr Met Asn Tyr Ala Gln Ile Arg
                580                 585                 590

Thr Ile Ala Ile Ile Ala Glu Gly Ile Pro Glu Ala Leu Thr Arg Lys
                595                 600                 605

Leu Ile Lys Lys Ala Asp Gln Lys Gly Val Thr Ile Ile Gly Pro Ala
610                 615                 620

Thr Val Gly Gly Ile Lys Pro Gly Cys Phe Lys Ile Gly Asn Thr Gly
625                 630                 635                 640

Gly Met Leu Asp Asn Ile Leu Ala Ser Lys Leu Tyr Arg Pro Gly Ser
                645                 650                 655

Val Ala Tyr Val Ser Arg Ser Gly Gly Met Ser Asn Glu Leu Asn Asn
                660                 665                 670

Ile Ile Ser Arg Thr Thr Asp Gly Val Tyr Glu Gly Val Ala Ile Gly
                675                 680                 685

Gly Asp Arg Tyr Pro Gly Ser Thr Phe Met Asp His Val Leu Arg Tyr
                690                 695                 700

Gln Asp Thr Pro Gly Val Lys Met Ile Val Val Leu Gly Glu Ile Gly
705                 710                 715                 720

Gly Thr Glu Glu Tyr Lys Ile Cys Arg Gly Ile Lys Glu Gly Arg Leu
                725                 730                 735

Thr Lys Pro Ile Val Cys Trp Cys Ile Gly Thr Cys Ala Thr Met Phe
                740                 745                 750

Ser Ser Glu Val Gln Phe Gly His Ala Gly Ala Cys Ala Asn Gln Ala
                755                 760                 765

Ser Glu Thr Ala Val Ala Lys Asn Gln Ala Leu Lys Glu Ala Gly Val
                770                 775                 780

Phe Val Pro Arg Ser Phe Asp Glu Leu Gly Glu Ile Ile Gln Ser Val
785                 790                 795                 800
```

```
Tyr Glu Asp Leu Val Ala Asn Gly Val Ile Val Pro Ala Gln Glu Val
                805                 810                 815

Pro Pro Pro Thr Val Pro Met Asp Tyr Ser Trp Ala Arg Glu Leu Gly
            820                 825                 830

Leu Ile Arg Lys Pro Ala Ser Phe Met Thr Ser Ile Cys Asp Glu Arg
            835                 840                 845

Gly Gln Glu Leu Ile Tyr Ala Gly Met Pro Ile Thr Glu Val Phe Lys
            850                 855                 860

Glu Glu Met Gly Ile Gly Gly Val Leu Gly Leu Leu Trp Phe Gln Lys
865                 870                 875                 880

Arg Leu Pro Lys Tyr Ser Cys Gln Phe Ile Glu Met Cys Leu Met Val
            885                 890                 895

Thr Ala Asp His Gly Pro Ala Val Ser Gly Ala His Asn Thr Ile Ile
            900                 905                 910

Cys Ala Arg Ala Gly Lys Asp Leu Val Ser Ser Leu Thr Ser Gly Leu
            915                 920                 925

Leu Thr Ile Gly Asp Arg Phe Gly Gly Ala Leu Asp Ala Ala Ala Lys
            930                 935                 940

Met Phe Ser Lys Ala Phe Asp Ser Gly Ile Ile Pro Met Glu Phe Val
945                 950                 955                 960

Asn Lys Met Lys Lys Glu Gly Lys Leu Ile Met Gly Ile Gly His Arg
            965                 970                 975

Val Lys Ser Ile Asn Asn Pro Asp Met Arg Val Gln Ile Leu Lys Asp
            980                 985                 990

Tyr Val Arg Gln His Phe Pro Ala Thr Pro Leu Leu Asp Tyr Ala Leu
            995                 1000                1005

Glu Val Glu Lys Ile Thr Thr Ser Lys Lys Pro Asn Leu Ile Leu
    1010                1015                1020

Asn Val Asp Gly Leu Ile Gly Val Ala Phe Val Asp Met Leu Arg
    1025                1030                1035

Asn Cys Gly Ser Phe Thr Arg Glu Glu Ala Asp Glu Tyr Ile Asp
    1040                1045                1050

Ile Gly Ala Leu Asn Gly Ile Phe Val Leu Gly Arg Ser Met Gly
    1055                1060                1065

Phe Ile Gly His Tyr Leu Asp Gln Lys Arg Leu Lys Gln Gly Leu
    1070                1075                1080

Tyr Arg His Pro Trp Asp Asp Ile Ser Tyr Val Leu Pro Glu His
    1085                1090                1095

Met Ser Met
    1100

<210> SEQ ID NO 39
<211> LENGTH: 1112
<212> TYPE: PRT
<213> ORGANISM: Drosophila melanogaster

<400> SEQUENCE: 39

Met Ser Ala Lys Ala Ile Thr Glu Ala Ser Gly Lys Asp Ile Leu Asn
1               5                   10                  15

Arg His Leu Asn Thr His Gly Ala Gly Ala Ala Thr Cys Arg Phe Ser
            20                  25                  30

Thr Val Asn Ser Thr Thr Asp Trp Ser Lys Leu Ala Val Asp His Pro
        35                  40                  45

Trp Leu Leu Thr Thr Pro Leu Val Cys Lys Pro Asp Gln Leu Ile Lys
    50                  55                  60
```

```
Arg Arg Gly Lys Leu Gly Leu Ile Gly Val Lys Lys Asn Phe Glu Gln
 65                  70                  75                  80

Val Lys Gln Trp Ile Gly Glu Arg Leu Asn Lys Asp Gln Lys Ile Gly
                 85                  90                  95

Asn Ala Val Gly Lys Leu Arg Asn Phe Ile Ile Glu Pro Phe Val Pro
            100                 105                 110

His Thr Asp Ala Glu Glu Met Tyr Val Cys Ile Tyr Ser His Arg Ala
        115                 120                 125

Ala Asp Thr Ile Leu Phe Tyr His Gln Gly Gly Val Asp Ile Gly Asp
    130                 135                 140

Val Asp Ala Lys Ala Val Lys Leu Asp Val Pro Val Asn Ser Ser Leu
145                 150                 155                 160

Ser Leu Ala Asp Val Lys Ser Lys Leu Leu Lys Glu Val Lys Asp Ala
                165                 170                 175

Gly Thr Lys Glu Arg Ile Ala Lys Phe Val Ser Ala Leu Tyr Thr Thr
            180                 185                 190

Tyr Val Asp Leu Tyr Phe Thr Tyr Leu Glu Ile Asn Pro Leu Val Val
        195                 200                 205

Thr Ala Asp Asn Leu Tyr Ile Leu Asp Leu Ala Ala Lys Leu Asp Ser
210                 215                 220

Thr Ala Asp Phe Ile Cys Arg Pro Lys Trp Gly Glu Ile Asp Tyr Pro
225                 230                 235                 240

Pro Pro Phe Gly Arg Asp Ala Tyr Pro Glu Glu Ala Tyr Ile Ala Asp
            245                 250                 255

Leu Asp Ala Lys Ser Gly Ala Ser Leu Lys Leu Thr Ile Leu Asn Arg
            260                 265                 270

Asn Gly Arg Ile Trp Thr Met Val Ala Gly Gly Ala Ser Val Ile
            275                 280                 285

Tyr Ser Asp Thr Ile Cys Asp Leu Gly Gly Ala Ser Glu Leu Ala Asn
        290                 295                 300

Tyr Gly Glu Tyr Ser Gly Ala Pro Ser Glu Gln Gln Thr Tyr Glu Tyr
305                 310                 315                 320

Ala Lys Thr Ile Leu Asn Leu Met Thr Ser Ser Pro Lys His Pro Asp
                325                 330                 335

Gly Lys Val Leu Ile Thr Gly Gly Ile Ala Asn Phe Thr Asn Val
            340                 345                 350

Ala Ala Thr Phe Gln Gly Ile Ile Thr Ala Leu Arg Glu Phe Gln Pro
        355                 360                 365

Lys Leu Val Glu His Asn Val Ser Ile Phe Val Arg Arg Ala Gly Pro
        370                 375                 380

Asn Tyr Gln Glu Gly Leu Arg Lys Met Arg Asp Phe Gly Ser Thr Leu
385                 390                 395                 400

Gly Ile Pro Leu His Val Phe Gly Pro Glu Thr His Met Thr Ala Ile
            405                 410                 415

Cys Gly Met Ala Leu Gly Lys Arg Pro Ile Pro Gln Thr Ala Ser Val
            420                 425                 430

Glu Phe Ser Thr Ala Asn Phe Leu Leu Pro Gly Gly Gln Gln Ala Gln
        435                 440                 445

Ala Asp Leu Lys Ala Ala Ser Asp Ala Ser Glu Ala Leu Gly Ser Gly
450                 455                 460

Ser Ala Leu Ser Pro Thr Ala Ala Lys Pro Ile Lys Leu Pro Pro Ile
465                 470                 475                 480

Ser Ala Asp Glu Ala Asp Ser Ala Gly Ile Ser Gly Ala Gln Arg Asn
            485                 490                 495
```

```
Gly Ser Ser Leu Asn Arg Lys Phe Phe Ser Asn Thr Thr Lys Ala Ile
            500                 505                 510

Val Trp Gly Met Gln Gln Arg Ala Val Gln Ser Met Leu Asp Phe Asp
            515                 520                 525

Phe Ile Cys Arg Arg Asp Glu Pro Ser Val Val Ala Met Val Tyr Pro
530                 535                 540

Phe Thr Gly Asp His Lys Gln Lys Tyr Tyr Trp Gly His Lys Glu Ile
545                 550                 555                 560

Leu Ile Pro Val Tyr Lys Lys Met Ser Asp Ala Ile His Lys His Lys
                565                 570                 575

Glu Val Asp Val Met Val Asn Phe Ala Ser Met Arg Ser Ala Tyr Glu
                580                 585                 590

Ser Thr Leu Glu Val Leu Glu Phe Pro Gln Ile Arg Thr Val Ala Ile
            595                 600                 605

Ile Ala Glu Gly Ile Pro Glu Asn Met Thr Arg Lys Leu Ile Ile Glu
            610                 615                 620

Ala Asp Lys Lys Gly Val Ala Ile Ile Gly Pro Ala Thr Val Gly Gly
625                 630                 635                 640

Val Lys Pro Gly Cys Phe Lys Ile Gly Asn Thr Gly Gly Met Leu Asp
                645                 650                 655

Asn Ile Leu His Ser Lys Leu Tyr Arg Pro Gly Ser Val Ala Tyr Val
                660                 665                 670

Ser Arg Ser Gly Gly Met Ser Asn Glu Leu Asn Asn Ile Ile Ser Lys
            675                 680                 685

Ala Thr Asp Gly Val Ile Glu Gly Ile Ala Ile Gly Gly Asp Arg Tyr
            690                 695                 700

Pro Gly Ser Thr Phe Met Asp His Ile Leu Arg Tyr Gln Ala Asp Pro
705                 710                 715                 720

Glu Thr Lys Leu Ile Val Leu Leu Gly Glu Val Gly Gly Thr Glu Glu
                725                 730                 735

Tyr Asp Val Cys Ala Ala Leu Lys Asp Gly Arg Ile Thr Lys Pro Leu
                740                 745                 750

Val Ala Trp Cys Ile Gly Thr Cys Ala Ser Met Phe Thr Ser Glu Val
            755                 760                 765

Gln Phe Gly His Ala Gly Ser Cys Ala Asn Ser Asp Arg Glu Thr Ala
            770                 775                 780

Thr Ala Lys Asn Lys Gly Leu Arg Asp Ala Gly Ala Tyr Val Pro Asp
785                 790                 795                 800

Ser Phe Asp Thr Leu Gly Glu Leu Ile His His Val Tyr Gly Glu Leu
                805                 810                 815

Val Lys Thr Gly Arg Val Val Pro Lys Glu Val Pro Pro Thr
                820                 825                 830

Val Pro Met Asp Tyr Ser Trp Ala Arg Glu Leu Gly Leu Ile Arg Lys
            835                 840                 845

Pro Ala Ser Phe Met Thr Ser Ile Cys Asp Glu Arg Gly Gln Glu Leu
850                 855                 860

Ile Tyr Ala Gly Met Pro Ile Ser Glu Val Leu Ser Lys Asp Val Gly
865                 870                 875                 880

Ile Gly Gly Val Ile Ser Leu Leu Trp Phe Gln Arg Cys Leu Pro Ser
                885                 890                 895

Tyr Val Cys Lys Phe Phe Glu Met Cys Leu Met Val Thr Ala Asp His
                900                 905                 910

Gly Pro Ala Val Ser Gly Ala His Asn Thr Ile Val Cys Ala Arg Ala
```

```
                    915                 920                 925
Gly Lys Asp Leu Val Ser Val Ser Gly Leu Leu Thr Ile Gly
        930                 935                 940

Asp Arg Phe Gly Gly Ala Leu Asp Gly Ser Ala Arg Gln Phe Ser Glu
945                 950                 955                 960

Ala Tyr Asp Thr Asn Leu His Pro Met Glu Phe Val Asn Lys Met Arg
                965                 970                 975

Lys Glu Gly Lys Leu Ile Leu Gly Ile Gly His Arg Val Lys Ser Ile
                980                 985                 990

Asn Asn Pro Asp Val Arg Val Lys Ile Ile Lys Glu Phe Val Leu Glu
                995                 1000                1005

Asn Phe Pro Ala Cys Pro Leu Leu Lys Tyr Ala Leu Glu Val Glu
    1010                1015                1020

Lys Ile Thr Thr Asn Lys Lys Pro Asn Leu Ile Leu Asn Val Asp
    1025                1030                1035

Gly Val Ile Ala Thr Ala Phe Val Asp Met Leu Arg Asn Ser Gly
    1040                1045                1050

Ser Phe Thr Ser Glu Glu Ala Gln Glu Tyr Ile Asn Val Gly Ala
    1055                1060                1065

Ile Asn Ser Leu Phe Val Leu Gly Arg Ser Ile Gly Phe Ile Gly
    1070                1075                1080

His Tyr Met Asp Gln Lys Arg Leu Lys Gln Gly Leu Tyr Arg His
    1085                1090                1095

Pro Trp Asp Asp Ile Ser Tyr Val Ile Pro Glu Gln Tyr Asn
    1100                1105                1110

<210> SEQ ID NO 40
<211> LENGTH: 1099
<212> TYPE: PRT
<213> ORGANISM: Caenorhabditis elegans

<400> SEQUENCE: 40

Met Ser Ala Lys Ala Val Ser Glu Leu Ser Gly Lys Glu Val Leu Tyr
1               5                   10                  15

Lys Tyr Phe Glu Ser Thr Gly Ile Val Ser Ala Pro His Ala Phe His
                20                  25                  30

Val Lys Ala Gly Asp Lys Phe Ser Asp Val Ala Ala Lys Tyr Glu Trp
            35                  40                  45

Leu Ala Gln Asp Asn Lys Gly Val Ile Lys Pro Asp Gln Leu Ile Lys
        50                  55                  60

Arg Arg Gly Lys Leu Gly Leu Val Lys Ile Gly Ser Pro Lys Glu Leu
65                  70                  75                  80

Glu Ala Trp Phe Gly Lys Thr Ala Asn Ser Tyr Val Lys Val Gly Gln
                85                  90                  95

Thr Glu Gly Arg Leu His Thr Phe Ile Val Glu Pro Phe Cys Ala His
                100                 105                 110

Thr Glu Asn Glu Glu Met Tyr Ile Ala Ile Tyr Ser Glu Arg Cys Arg
            115                 120                 125

Asp Val Ile Met Phe Tyr Glu Gln Gly Gly Val Asp Ile Gly Asp Val
        130                 135                 140

Glu Glu Lys Ala Arg Ser Val His Val Pro Val Gln Leu Asp Asp Asn
145                 150                 155                 160

Ala Met Ser Ile Ser Glu Arg Glu Leu Gly Val Leu Leu Gly Pro Cys
                165                 170                 175

Ser Asp Lys Asp Asp Ile Arg Lys Phe Val Arg Ser Leu Tyr Glu Ala
```

-continued

```
                180                 185                 190
Tyr Lys Ala Leu His Phe Thr Tyr Leu Glu Ile Asn Pro Phe Val Leu
            195                 200                 205
Thr Asn Gly Lys Ile His Ile Leu Asp Leu Ala Ala Lys Leu Asp Glu
            210                 215                 220
Thr Ala Ser Phe Leu Cys Ser Asp Lys Trp Ser Gly Arg Asn Ala Ser
225                 230                 235                 240
Ala Arg Ile Ala Pro Thr Leu Glu Phe Pro Ala Pro Phe Gly Arg Asp
            245                 250                 255
Leu Thr Ser Glu Glu Gln Tyr Ile Ser Asp Met Asp Ala Lys Thr Gly
            260                 265                 270
Ala Ser Leu Lys Leu Thr Ile Leu Asn Arg Lys Gly Arg Val Trp Thr
            275                 280                 285
Met Val Ala Gly Gly Ala Ser Val Val Phe Thr Asp Thr Val Cys
            290                 295                 300
Asp Leu Gly Gly Ser Ser Glu Leu Ala Asn Tyr Gly Glu Tyr Ser Gly
305                 310                 315                 320
Asp Pro Ser Glu Ala Gln Thr Tyr Glu Tyr Ala Lys Thr Ile Leu Ser
            325                 330                 335
Val Met Thr Glu Gly Ala Pro Arg Pro Asp Gly Lys Val Leu Ile Ile
            340                 345                 350
Gly Gly Ser Ile Ala Asn Phe Thr Asn Val Ala Lys Thr Phe Gly Gly
            355                 360                 365
Ile Val Arg Ala Phe Glu Thr Phe Ile Asp Lys Leu Lys Glu His Asn
            370                 375                 380
Val Ser Ile Tyr Val Arg Arg Gly Gly Pro Asn Tyr Gln Glu Gly Leu
385                 390                 395                 400
Arg Arg Val Lys Asp Ala Ala Thr Lys Leu Glu Ile Pro Ile Tyr Val
            405                 410                 415
Phe Gly Pro Glu Thr His Met Thr Ala Ile Val Gly Ala Ala Leu Gly
            420                 425                 430
Leu Lys Pro Met Pro Thr Val Pro Thr Ala Pro Gln Thr Thr Gly Gln
            435                 440                 445
Phe Leu Leu Ser Pro Glu Arg Asn Thr Ala Gly Thr Glu Arg Pro Pro
            450                 455                 460
Ala Ser Pro Ala Pro Asn Thr Ser Thr Ile Glu His Pro Leu Ala Lys
465                 470                 475                 480
Arg His Pro Leu His Gln Ser Leu Phe Glu Asn Asp Thr Lys Ala Ile
            485                 490                 495
Ile Trp Gly Gln Gln His Lys Ala Ile Gln Gly Met Leu Asp Phe Asp
            500                 505                 510
Phe Val Cys Arg Arg His Ser Pro Ser Val Val Ala Ser Thr Tyr Pro
            515                 520                 525
Phe Thr Gly Asp Asn Lys Gln Lys Tyr Tyr Phe Gly Asn Lys Glu Ile
            530                 535                 540
Leu Ile Pro Ala Tyr Lys Ser Met Ala Lys Ala Phe Ala Ser His Pro
545                 550                 555                 560
Asp Ala Thr Val Met Val Thr Phe Ala Ser Met Arg Ser Val Phe Glu
            565                 570                 575
Thr Val Leu Glu Ala Leu Gln Phe Thr Gln Ile Lys Val Ile Ala Ile
            580                 585                 590
Ile Ala Glu Gly Val Pro Glu Asn Gln Thr Arg Lys Leu Leu Lys Ile
            595                 600                 605
```

-continued

```
Ala Glu Asp Lys Gly Val Thr Leu Ile Gly Pro Ala Thr Val Gly Gly
        610                 615                 620
Ile Lys Pro Gly Cys Phe Lys Ile Gly Asn Thr Gly Gly Met Met Asp
625                 630                 635                 640
Asn Ile Leu Ala Ser Lys Leu Tyr Arg Pro Gly Ser Val Ala Tyr Val
                645                 650                 655
Ser Arg Ser Gly Gly Met Ser Asn Glu Leu Asn Asn Ile Ile Ser Gln
                660                 665                 670
Asn Thr Asn Gly Val Tyr Glu Gly Ile Ala Ile Gly Gly Asp Arg Tyr
            675                 680                 685
Pro Gly Ser Thr Tyr Thr Asp His Val Met Arg Tyr Gln His Asp Asp
        690                 695                 700
Arg Val Lys Met Ile Val Leu Leu Gly Glu Val Gly Gly Ile Glu Glu
705                 710                 715                 720
Tyr Arg Ile Val Glu Leu Leu Lys Glu Lys Lys Ile Thr Lys Pro Leu
                725                 730                 735
Ile Ala Trp Cys Ile Gly Thr Cys Ala Asp His Ile Thr Ser Glu Val
                740                 745                 750
Gln Phe Gly His Ala Gly Ala Ser Ala Asn Gly Gln Gly Glu Thr Ala
            755                 760                 765
Ala Cys Lys Asn Thr Ala Leu Arg Thr Ala Gly Ala Leu Val Pro Asp
        770                 775                 780
Ser Phe Asp Asp Leu Gly Asn Lys Ile Arg Gln Thr Tyr Glu Glu Leu
785                 790                 795                 800
Leu Arg Leu Glu Ile Ile Val Pro Gln Pro Glu Val Pro Pro Ala
                805                 810                 815
Val Pro Met Asp Tyr Ala Trp Ala Arg Glu Leu Gly Leu Ile Arg Lys
            820                 825                 830
Pro Ala Ser Phe Met Thr Ser Ile Cys Asp Glu Arg Gly Glu Glu Leu
        835                 840                 845
Asn Tyr Ala Gly Val Pro Ile Thr Lys Val Leu Glu Ser Asp Met Gly
        850                 855                 860
Ile Gly Gly Val Leu Gly Leu Leu Trp Phe Gln Lys Arg Leu Pro Pro
865                 870                 875                 880
His Ala Asn Lys Phe Ile Glu Ile Cys Leu Met Leu Thr Ala Asp His
                885                 890                 895
Gly Pro Ala Val Ser Gly Ala His Asn Thr Ile Val Cys Ala Arg Ala
            900                 905                 910
Gly Lys Asp Leu Ile Ser Ser Leu Thr Ser Gly Leu Leu Thr Ile Gly
        915                 920                 925
Asp Arg Phe Gly Gly Ala Leu Asp Gly Ala Ala Arg Gln Phe Ser Glu
        930                 935                 940
Ala Phe Asp Gln Gly Trp Ser Pro Asn Gln Phe Val Gly Glu Met Arg
945                 950                 955                 960
Lys Arg Gly Thr His Ile Met Gly Ile Gly His Arg Val Lys Ser Ile
                965                 970                 975
Asn Asn Pro Asp Lys Arg Val Gln Ile Leu Lys Arg Phe Ala Leu Asn
            980                 985                 990
Lys Lys Glu Phe Ala Gln Glu Thr Pro Leu Leu Asp Tyr Ala Leu Glu
        995                 1000                1005
Val Glu Lys Ile Thr Thr Ala Lys Lys Pro Asn Leu Ile Leu Asn
    1010                1015                1020
Val Asp Gly Ala Ile Ala Ile Ile Phe Val Asp Ile Leu Arg Asn
    1025                1030                1035
```

```
Ser Gly Met Phe Thr Thr Ala Glu Ala Gln Glu Val Ile Glu Ile
    1040            1045                1050

Gly Ala Leu Asn Gly Met Phe Val Leu Gly Arg Ser Ile Gly Phe
    1055            1060                1065

Ile Gly His Tyr Leu Asp Gln Ser Arg Leu Lys Gln Gly Leu Tyr
    1070            1075                1080

Arg His Pro Trp Asp Asp Ile Ser Tyr Ile Met Pro Glu Arg Asn
    1085            1090                1095

Leu

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
tttttttttt tttttttttt tttttttttt                                           30
```